(12) United States Patent
Reeves et al.

(10) Patent No.: US 9,790,522 B2
(45) Date of Patent: Oct. 17, 2017

(54) COMPOSITIONS AND METHODS FOR THE CONVERSION OF SHORT-CHAINED CARBOXYLIC ACIDS TO ALCOHOLS USING CLOSTRIDIAL ENZYMES

(71) Applicant: Coskata, Inc., Warrenville, IL (US)

(72) Inventors: Andrew Reeves, Chicago, IL (US); Richard Tobey, St. Charles, IL (US); Mike Enzien, Lisle, IL (US)

(73) Assignee: Synata Bio, Warrenville, IL (US)

( * ) Notice: Subject to any disclaimer, the term of this patent is extended or adjusted under 35 U.S.C. 154(b) by 0 days.

(21) Appl. No.: 14/680,195

(22) Filed: Apr. 7, 2015

(65) Prior Publication Data
US 2016/0298143 A1 Oct. 13, 2016

(51) Int. Cl.
| | |
|---|---|
| *C12N 1/02* | (2006.01) |
| *C12P 7/16* | (2006.01) |
| *C12P 1/04* | (2006.01) |
| *C12P 7/06* | (2006.01) |
| *C12P 7/08* | (2006.01) |
| *C12R 1/145* | (2006.01) |
| *C12P 39/00* | (2006.01) |
| *A61K 38/00* | (2006.01) |

(52) U.S. Cl.
CPC ............ *C12P 7/16* (2013.01); *C12P 7/065* (2013.01); *C12P 7/08* (2013.01); *C12P 39/00* (2013.01); *C12R 1/145* (2013.01); *C12Y 102/07005* (2013.01); Y02E 50/10 (2013.01); Y02E 50/17 (2013.01)

(58) Field of Classification Search
CPC ................ C12N 1/02; C12P 1/04; C12P 7/16
See application file for complete search history.

(56) References Cited

U.S. PATENT DOCUMENTS

| | | | |
|---|---|---|---|
| 4,539,293 A * | 9/1985 | Bergstrom | C12P 7/16 435/160 |
| 8,039,239 B2 | 10/2011 | Reeves | |
| 8,148,579 B2 * | 4/2012 | Bradin | C07C 29/143 435/148 |
| 2007/0275447 A1 | 11/2007 | Lewis et al. | |
| 2011/0008860 A1 | 1/2011 | Reeves et al. | |
| 2011/0229947 A1 | 9/2011 | Zahn et al. | |
| 2011/0236941 A1 * | 9/2011 | Koepke | C12N 9/0006 435/160 |
| 2013/0102044 A1 | 4/2013 | Reeves et al. | |
| 2014/0206052 A1 | 7/2014 | Enzien et al. | |
| 2014/0220649 A1 * | 8/2014 | Tobey | C12P 7/40 435/160 |

FOREIGN PATENT DOCUMENTS

| | | |
|---|---|---|
| WO | WO2008028055 | 6/2008 |
| WO | WO 2014/113209 | * 7/2014 |

OTHER PUBLICATIONS

Kopke et al. (2010) Clostridium ljungdahlii represents a microbial production platform based on syngas, Proced. Natl. Acad. Sci. USA, vol. 107, No. 29, pp. 13087-13092.*
Green, et al., "Genetic manipulation of acid formation pathways", Microbiology, 142:2079-2086 (1996).
Liu, et al., "Constructon and Characterization of an ack Deleted Mutant of Clostridium tyrobutyricum", Biotechnology Progress, 22:1265-1275 (2006).
White, et al, Euro. J. Biochem, 184:89-96 (1989).
White, et al., Biol. Chem. Hoppe-seyler, 372:999-1005 (1991).
Sonnhammer, et al, Nucl. Acids Res., 26:320-322 (1998).
Sonnhammer, et al, Proteins, 28:405-420 (1997).
Bateman, et al., Nucl. Acids Res., 27:260-262 (1999).
Balch and Wolfe, Appl. Environ. Microbiol., 32:781-791 (1976).
Balch, et al., Microbiol. Rev., 43:260-296 (1979).
Abrini, et al., Arch. Microbiol, 4:345-351 (1994).
Tanner, et al., Int. J. Syst Bacteriol, 43:232-236 (1993).
Baba, et al., Mo. Syst. Biol., 2:1-11 (2006).
Parke, Gene, 93:135-137 (1990).
Wang, et al., J. Bacteriol., 195:4373-4386 (2013).
Wang, et al., J. Bacteriol., 192:5115-5123 (2010).
Partridge, et al., Microbiology 154:608-618 (2008).
Leang, et al., Applied and Environmental Microgiology, 29:1102-1109 (2013).
Perez, et al., "Biocatalytic reduction of short-chain carboxylic acids into their corresponding alcohols with syngas fermentation", Biotechnology and Bioengineering, 110:1066-1077 (2013).
Isom, et al., "Improved conversion efficiencies fom-fatty acid reduction to primary alcohols by the solventogenic acetogen Clostridium ragsdale", Journal of Industrial microgiology and Biotechnology, 42:29-38 (2014).
Weimer, et al., "Production of medium-chain volatile fatty acids by mixed ruminal microorganisms is enhanced by ethanol in co-culture with Clostridium kluyveri", Bioresource Technology, 175:97-101 (2014).
International Search Report and Written Opinion for PCT/US2016/025991, mailed Nov. 16, 2016, pp. 1-15.

* cited by examiner

*Primary Examiner* — Anand Desai
*Assistant Examiner* — Samuel Liu
(74) *Attorney, Agent, or Firm* — McDonnell Boehnen Hulbert & Berghoff LLP

(57) ABSTRACT

The invention relates to the fields of bacterial metabolism and the utilization or consumption of short-chain carboxylic acids to reduced products. Specifically, it relates to syngas fermentations using monocultures of syngas-utilizing homoacetogenic bacteria for the production of alcohols using native alcohol dehydrogenase.

4 Claims, 17 Drawing Sheets

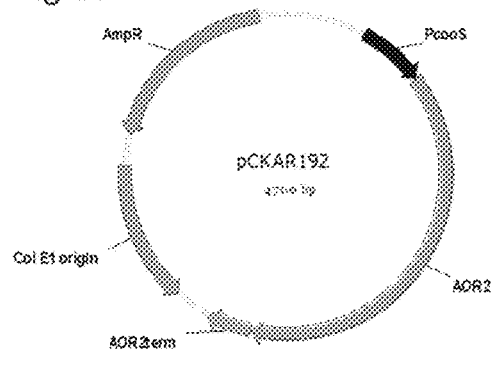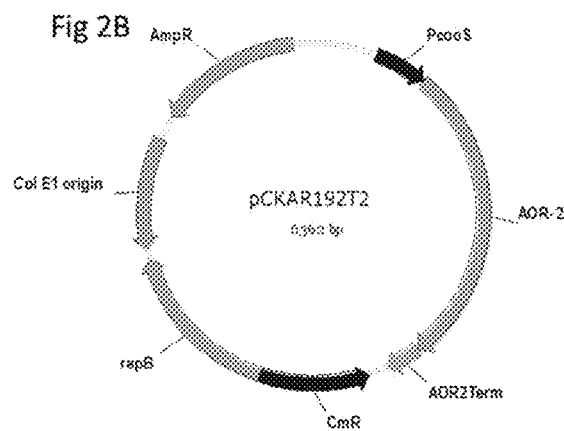

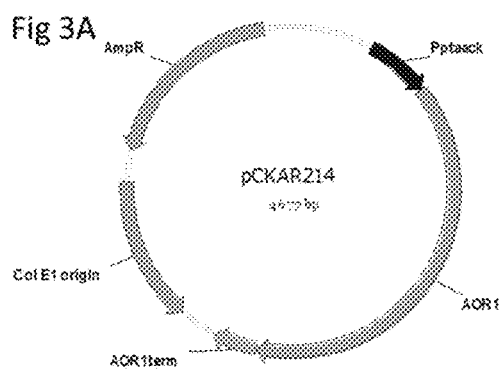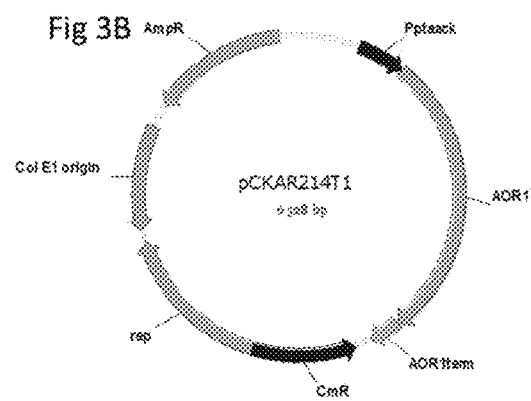

Fig.4a DNA sequence alignment of *C. autoethanogenum* AOR1 and AOR2.

```
AOR1    ATGTACGGATATAAGGGTAAGGTATTAAGAATTAATCTAAGTAGTAAAACTTATATAGTGGAAGAATTGAAAATTGACAA
AOR2    ATGTATGGTTATGATGGTAAAGTATTAAGAATTAATTTAAAAGAAAGAACTTGCAAATCAGAAAATTTAGATTTAGATA
        *****  **  ***  * ***** ****************  ***       *  *****  *  *   ***  * **  *   * **  **

AOR1    AGCTAAAAAATTTATAGGTGCAAGAGGGTTAGGCGTAAAAACCTTATTTGACGAAGTAGATCCAAAGGTAGATCCATTAT
AOR2    AGCTAAAAAGTTTATAGGTTGTAGGGGACTAGGTGTTAAAACTTTATTTGATGAAATAGATCCTAAAATAGATGCATTAT
        *********  ********  **   **   ****  **  *****  ********    ***  *******    **   *****  ******

AOR1    CACCTGATAACAAATTTATTATAGCAGCGGGACCACTTACAGGTGCACCTGTTCCAACAAGCGGAAGATTCATGGTAGTT
AOR2    CACCAGAAAATAAATTTATAATTGTAACAGGTCCTTTAACTGGAGCTCCGGTTCCAACTAGTGGAAGGTTTATGGTAGTT
        ****  **  **  ********   **   *  * *  *   **   **    *   **   **   ** ********  **  *****   ** *********

AOR1    ACTAAATCACCTTTAACAGGAACTATTGCTATTGCAAATTCAGGTGGAAAATGGGGAGCAGAATTCAAAGCAGCTGGATA
AOR2    ACTAAAGCACCGCTTACAGGAACTATAGGAATTTCAAATTCGGGTGGAAAATGGGGAGTAGACTTAAAAAAAGCTGGTTG
        ******  ****   *  ***********   *    ***  *  *** *******  **************  *** **  ***    ****** *

AOR1    CGATATGATAATCGTTGAAGGTAAATCTGATAAAGAAGTTTATGTAAATATAGTAGATGATAAAGTAGAATTTAGGGATG
AOR2    GGATATGATAATAGTAGAGGATAAGGCTGATTCACCAGTTTACATTGAAATAGTAGATGATAAGGTAGAAATTAAAGACG
        ***********  ** **  *  ***      *****    * ******    *  ***************  ******  ***   ** *

AOR1    CTTCTCATGTTTGGGGAAAACTAACAGAAGAAACTACAAAAATGCTTCAACAGGAAACAGATTCGAGAGCTAAGGTTTTA
AOR2    CGTCACAGCTTTGGGGAAAAGTTACATCAGAAACTACAAAAGAGTTAGAAAAGATAACTGAGAATAAATCAAAGGTATTA
        *  **  **  **********  * ***    *************        *  **  **  ***  **           *  *  * *****  ***

AOR1    TGCATAGGACCAGCTGGGGAAAAGTTATCACTTATGGCAGCAGTTATGAATGATGTTGATAGAACAGCAGGACGTGGTGG
AOR2    TGTATAGGACCTGCTGGTGAACGATTGTCTCTTATGGCAGCAGTTATGAATGATGTAGATAGAACTGCAGCAAGAGGCGG
        **  ********  ****  ***   **  **  *****************************  ********  *****  ****   *   ** **

AOR1    TGTTGGAGCTGTTATGGGTTCAAAGAACTTAAAAGCTATTGTAGTTAAAGGAAGCGGAAAAGTAAAATTATTTGATGAAC
AOR2    CGTTGGTGCAGTTATGGGATCTAAAAACTTAAAAGCTATTACAGTTAAAGGAACTGGAAAAATAGCTTTAGCTGATAAAG
         *****  **  ********  ** ***  **************   ********     ******    **    ***  **** **

AOR1    AAAAAGTGAAGGAAGTAGCACTTGAGAAAACAAATATTTTAAGAAAAGATCCAGTAGCTGGTGGAGGACTTCCAACATAC
AOR2    AAAAAGTAAAAAAAAGTGTCCGTAGAAAAAATTACAACATTAAAAAATGATCCAGTAGCTGGTCAGGGAATGCCAACTTAT
        *******  **   ****  *  *  **   ****   *   *   ****  ***  **************     ***  *  *****  **

AOR1    GGAACAGCTGTACTTGTTAATATTATAAATGAAAATGGTGTACATCCAGTAAAGAATTTTCAAAAATCTTATACAGATCA
AOR2    GGTACAGCTATACTGGTTAATATAATAAATGAAATGGAGTTCATCCTGTAAAGAATTTTCAAGAGTCTTATACGAATCA
        **  ****** ****  ******* *********** *****  ** ***  **********************  *  *********   ****

AOR1    AGCAGATAAGATCAGTGGAGAAACTTTAACTAAAGATTGCTTAGTTAGAAAAAATCCTTGCTATAGGTGTCCAATTGCCT
AOR2    AGCAGATAAAATAAGTGGAGAGACTCTTACTGCTAACCAACTAGTAAGGAAAAATCCTTGTTACAGCTGTCCTATAGGTT
        *********  **  *******  *** *  ***   *  ***        *      ****  ** **********  **  ** *****  **  *

AOR1    GTGGAAGATGGGTAAAACTTGATGATGGAACTGAATGTGGAGGACCAGAATATGAAACATTATGGTCATTTGGATCTGAT
AOR2    GTGGAAGATGGGTTAGACTAAAAGATGGCACAGAGTGCGGAGGACCAGAATATGAAACACTGTGGTGTTTTGGATCTGAC
        *************   ***   *****  ** *** ** ***************  ****  *** **  ** ***********

AOR1    TGTGATGTATACGATATAAATGCTGTAAATACAGCAAATATGTTGTGTAATGAATATGGACTAGATACCATTACAGCAGG
AOR2    TGTGGTTCATATGATTTAGATGCTATAAATGAAGCTAATATGTTATGTAATGAATATGGTATTGATACTATTACTTGTGG
        ****  *   *** *** **  ******  ***   ***  ***********   ***********  *  ***** *****       **

AOR1    ATGTACTATTGCAGCAGCTATGGAACTTTATCAAAGAGGTTATATTAAGGATGAAGAAATAGCAGCAGATGGATTGTCAC
AOR2    TGCAACAATTGCTGCAGCTATGGAACTTTATCAAAGAGGATATATAAAAGACGAAGAAATAGCTGGAGATAACCTATCTC
         *  *****  ************************  *****  ** ** **  **  *********** *  ****      *  ** *
```

Fig.4a (continued)

```
AOR1   TTAATTGGGGAGATGCTAAGTCCATGGTTGAATGGGTAAAGAAAATGGGACTTAGAGAAGGATTTGGAGACAAGATGGCA
AOR2   TCAAGTGGGGTGATACGGAATCTATGATTGGCTGGATAAAGAGAATGGTATATAGTGAAGGCTTTGGAGCAAAGATGACA
       *  **  *****  ***  *    *  **  ***  ***    ***  ******  *****  *    ***  *****  ******         ******  **

AOR1   GATGGTTCATACAGACTTTGTGACTCATACGGTGTACCTGAGTATTCAATGACTGTAAAAAAACAGGAACTTCCAGCATA
AOR2   AATGGTTCATATAGGCTTTGTGAAGGTTATGGAGCACCGGAGTATTCTATGACAGTTAAAAAGCAGGAAATTCCAGCATA
        *********  **  ********       **  **  *  ***  ********  *****  **  *****  ******  *********

AOR1   TGACCCAAGAGGAATACAGGGACATGGCATTACTTATGCTGTTAACAATAGGGGAGGATGTCACATTAAGGGATATATGG
AOR2   TGATCCAAGGGGAATACAGGGACACGGTATTACCTATGCAGTTAATAATAGAGGAGGCTGTCATATTAAGGGATACATGA
       ***  *****  ************  ***  ******  *****   *****  *****  *****  *****      *****     **********    ***

AOR1   TAAGTCCTGAAATACTTGGCTATCCAGAAAAACTTGATAGACTTGCAGTGGAAGGAAAAGCAGGATATGCTAGAGTATTC
AOR2   TTAACCCTGAAATATTAGGTTATCCTGAAAAACTTGATAGATTTGCATTAGATGGTAAAGCAGCTTATGCCAAATTATTT
       *   *    *********   *   **  *****  ****************  *****   *  **  **  *******       *****  *  *  ****

AOR1   CATGATTTAACAGCTGTTATAGATTCACTTGGATTATGTATTTTTACAACATTTGGTCTTGGTGCACAGGATTATGTTGA
AOR2   CATGATTTAACTGCTGTAATTGATTCTTTAGGATTGTGCATATTCACTACATTTGGGCTTGGAATACAGGATTATGTAGA
       ***********  *****  **  *****     *  *****  **  **  **  **  *********  *****                 ************  **

AOR1   TATGTATAATGCAGTAGTTGGTGGAGAATTACATGATGTAAATTCTTTAATGTTAGCTGGAGATAGAATATGGACTTTAG
AOR2   TATGTATAATGCAGTAGTAGGAGAATCTACTTATGATGCAGATTCACTATTAGAGGCAGGAGATAGAATCTGGACTCTTG
       ******************  **  *  *       ******  *  ****   **  *        **  ***********  ******   *  *

AOR1   AAAAAATATTTAACTTAAAAGCAGGCATAGATAGTTCACAGGATACTCTTCCAAAGAGATTGCTTGAAGAACAAATTCCA
AOR2   AGAAATTATTTAATCTTGCAGCTGGAATAGACAGCAGCCAGGATACTCTACCAAAGAGATTGTTAGAAGAACCTATTCCA
       *  ***  *******     *    ***  **  *****  **         ***********   ************    *  *******     ******

AOR1   GAAGGACCATCAAAAGGAGAAGTTCATAAGTTAGATGTACTACTACCTGAATATTATTCAGTACGTGGATGGGATAAAAA
AOR2   GATGGCCCATCAAAGGGAGAAGTTCATAGGCTAGATGTTCTTCTGCCAGAATATTACTCAGTACGAGGATGGAGTAAAGA
       **  **  ********  **************  *  ******  **  **  **  *******  ********  ******  ****     *

AOR1   TGGTATTCCTACAGAGGAAACGTTAAAGAAATTAGGATTAGATGAATACGTAGGTAAGCTTTAG (SEQ ID NO: 1)
AOR2   GGGTATACCTACAGAAGAAACATTAAAGAAATTAGGATTAGATGAATATATAGGTAAGTTCTAG (SEQ ID NO: 3)
       *****  *******  *****    ****************************** *******  *  ***
```

Fig. 4b. Amino acid sequence alignment of AOR1 and AOR2.

```
CAUTOAOR1   MYGYDGKVLRINLKERTCKSENLDLDKAKKFIGCRGLGVKTLFDEIDPKIDALSPENKFIIVTGPLTGAPVPTSGRFMVV
CAUTOAOR2   MYGYKGKVLRINLSSKTYIVEELKIDKAKKFIGARGLGVKTLFDEVDPKVDPLSPDNKFIIAAGPLTGAPVPTSGRFMVV
            ****.********..:*   *:*.:********.*********.***:*.***:****.:******************

CAUTOAOR1   TKAPLTGTIGISNSGGKWGVDLKKAGWDMIIVEDKADSPVYIEIVDDKVEIKDASQLWGKVTSETTKELEKITENKSKVL
CAUTOAOR2   TKSPLTGTIAIANSGGKWGAEFKAAGYDMIIVEGKSDKEVYVNIVDDKVEFRDASHVWGKLTEETTKMLQQETDSRAKVL
            **:******.*.*******.::* **:******.*:*. **.:*******:.***::***:*:**** *::.*:..***

CAUTOAOR1   CIGPAGERLSLMAAVMNDVDRTAARGGVGAVMGSKNLKAITVKGTGKIALADKEKVKKVSVEKITTLKNDPVAGQGMPTY
CAUTOAOR2   CIGPAGEKLSLMAAVMNDVDRTAGRGGVGAVMGSKNLKAIVVKGSGKVKLFDEQKVKEVALEKTNILRKDPVAGGGLPTY
            *******:***************.***************.***.**:.*  * *::**:*:**    *  *::****  *:***

CAUTOAOR1   GTAILVNIINENGVHPVKNFQESYTNQADKISGETLTANQLVRKNPCYSCPIGCGRWVRLKDGTECGGPEYETLWCFGSD
CAUTOAOR2   GTAVLVNIINENGVHPVKNFQKSYTDQADKISGETLTKDCLVRKNPCYRCPIACGRWVKLDDGTECGGPEYETLWSFGSD
            ***:*****************:***.**********. : *******.***.****.*.********************.****

CAUTOAOR1   CGSYDLDAINEANMLCNEYGIDTITCGATIAAAMELYQRGYIKDEEIAGDNLSLKWGDTESMIGWIKRMVYSEGFGAKMT
CAUTOAOR2   CDVYDINAVNTANMLCNEYGLDTITAGCTIAAAMELYQRGYIKDEEIAADGLSLNWGDAKSMVEWVKKMGLREGFGDKMA
            *. **::*:* *********.****.*.********************.*.***.***::**.  *:*.*   **** **:

CAUTOAOR1   NGSYRLCEGYGAPEYSMTVKKQEIPAYDPRGIQGHGITYAVNNRGGCHIKGYMINPEILGYPEKLDRFALDGKAAYAKLF
CAUTOAOR2   DGSYRLCDSYGVPEYSMTVKKQELPAYDPRGIQGHGITYAVNNRGGCHIKGYMVSPEILGYPEKLDRLAVEGKAGYARVF
            :******.:**.**********:*******************************:.*********:*::***.**::*
```

Fig.4b (continued)

```
CAUTOAOR1    HDLTAVIDSLGLCIFTTFGLGIQDYVDMYNAVVGESTYDADSLLEAGDRIWTLEKLFNLAAGIDSSQDTLPKRLLEEPIP
CAUTOAOR2    HDLTAVIDSLGLCIFTTFGLGAQDYVDMYNAVVGGELHDVNSLMLAGDRIWTLEKIFNLKAGIDSSQDTLPKRLLEEQIP
             *******************.********** .:*.:**: *********:*** ****************** **

CAUTOAOR1    DGPSKGEVHRLDVLLPEYYSVRGWSKEGIPTEETLKKLGLDEYIGKF (SEQ ID NO: 4)
CAUTOAOR2    EGPSKGEVHKLDVLLPEYYSVRGWDKNGIPTEETLKKLGLDEYVGKL (SEQ ID NO: 2)
             :*******:*************.*:************:**:
```

Fig. 5A. Multiple amino acid sequence alignment of *C. autoethanogenum* AOR1 with two other AOR from homoacetogens.

```
CAUTOAOR1    MYGYKGKVLRINLSSKTYIVEELKIDKAKKFIGARGLGVKTLFDEVDPKVDPLSPDNKFIIAAGPLTGAPVPTSGRFMVV
CLUNGAOR1    MYGYKGKVLRINLSSKTYIVEELKIDKAKKFIGARGLGVKTLFDEVDPKVDPLSPDNKFIIAAGPLTGAPVPTSGRFMVV
CRAGSAOR1    MYGYSGKVLRINLSNKTYKAEELKIDEAKKFIGARGLGVKTLLDEIDPKIDPLSPDNKFIIATGPLTGAPVPTSGRFMVI
             ****.*********.*** .****:********:*******:.***:*:***************:*****************:

CAUTOAOR1    TKSPLTGTIAIANSGGKWGAEFKAAGYDMIIVEGKSDKEVYVNIVDDKVEFRDASHVWGKLTEETTKMLQQETDSRAKVL
CLUNGAOR1    TKSPLTGTIAIANSGGKWGAEFKAAGYDMIIVEGKSDKEVYVNIVDDKVEFRDASHVWGKLTEETTKMLQQETDSRAKVL
CRAGSAOR1    TKAPLTGTIGIANSGGKWGAELKTAGYDMVIVEGKSDKPVYVNIVDDKVEFKDASHVWGKLTEETTKMLQNEIDAKAKVL
             **.******.***********:*:*****:*******.************:****************:* *:.:****

CAUTOAOR1    CIGPAGEKLSLMAAVMNDVDRTAGRGGVGAVMGSKNLKAIVVKGSGKVKLFDEQKVKEVALEKTNILRKDPVAGGGLPTY
CLUNGAOR1    CIGPAGEKLSLMAAVMNDVDRTAGRGGVGAVMGSKNLKAIVVKGSGKVKLFDEQKVKEVALEKTNILRKDPVAGGGLPTY
CRAGSAOR1    CIGPAGENLSLMAAVMNDIDRTAGRGGVGAVMGSKNLKAIVVKGSGKVKLFDEEKVKAVSLQKSDILRKDPVAGGGLPTY
             *******:**********:*********************************:*** *:*:*::**************

CAUTOAOR1    GTAVLVNIINENGVHPVKNFQKSYTDQADKISGETLTKDCLVRKNPCYRCPIACGRWVKLDDGTECGGPEYETLWSFGSD
CLUNGAOR1    GTAVLVNIINENGVHPVKNFQKSYTDQADKISGETLTKDCLVRKNPCYRCPIACGRWVKLDDGTECGGPEYETLWSFGSD
CRAGSAOR1    GTAVLVNIINENGINPVRNFQESYTDEADKVSGETMTQECLVRKNPCYRCPIACGRWVRLDDGTECGGPEYETLWSFGSD
             *************::**:***:****:***:****:*:*****************:*********************

CAUTOAOR1    CDVYDINAVNTANMLCNEYGLDTITAGCTIAAAMELYQRGYIKDEEIAADGLSNWGDAKSMVEWVKKMGLREGFGDKMA
CLUNGAOR1    CDVYDINAVNTANMLCNEYGLDTITAGCTIAAAMELYQRGYIKDEEIAADGLSNWGDAKSMVEWVKKMGLREGFGDKMA
CRAGSAOR1    CDVYDLNAVNKANMLCNEYGLDTISAGATIASAMELYQRGYIKDEEIAADGLSLKWGDAKSMVEWVKKMGRREGFGGKMA
             *****:****.************:*** ***:*****************:***************** ***** ***

CAUTOAOR1    DGSYRLCDSYGVPEYSMTVKKQELPAYDPRGIQGHGITYAVNNRGGCHIKGYMVSPEILGYPEKLDRLAVEGKAGYARVF
CLUNGAOR1    DGSYRLCDSYGVPEYSMTVKKQELPAYDPRGIQGHGITYAVNNRGGCHIKGYMVSPEILGYPEKLDRLAVEGKAGYARVF
CRAGSAOR1    DGSYRLCESYGVPQYSMSVKKQELPAYDPRGAQGHGLTYAVNNRGGCHIKGYMISPEILGYPEKLDRFSIEGKPAYAKVF
             *******:*****:***.************.****:*****************:************::***..**:**

CAUTOAOR1    HDLTAVIDSLGLCIFTTFGLGAQDYVDMYNAVVGGELHDVNSLMLAGDRIWTLEKIFNLKAGIDSSQDTLPKRLLEEQIP
CLUNGAOR1    HDLTAVIDSLGLCIFTTFGLGAQDYVDMYNAVVGGELHDVNSLMLAGDRIWTLEKIFNLKAGIDSSQDTLPKRLLEEQIP
CRAGSAOR1    HDLTAVIDSLGLCIFTTFGLGAQDYVDMYNAVVGGELHDVDSLMLAGDRVWTLEKIFNLKAGVGSSQDTLPKRLLEEEVV
             ***************************************.*******:************.*************::

CAUTOAOR1    EGPSKGEVHKLDVLLPEYYSVRGWDKNGIPTEETLKKLGLDEYVGKL (SEQ ID NO: 2)
CLUNGAOR1    EGPSKGEVHKLDVLLPEYYSVRGWDKNGIPTEETLKKLGLDEYVGKL (SEQ ID NO: 15)
CRAGSAOR1    EGPSKGHVHRLDELVPEYYSVRGWDKNGVPTEETLKKLGLEEYIGKI (SEQ ID NO: 16)
             ******.**:** *:************.***********:**:**:
```

Fig. 5b. Multiple amino acid sequence alignment of *C. autoethanogenum* AOR 2 with two other AORs from homoacetogens.

```
CAUTOAOR2    MYGYDGKVLRINLKERTCKSENLDLDKAKKFIGCRGLGVKTLFDEIDPKIDALSPENKFIIVTGPLTGAPVPTSGRFMVV
CLJUNAOR2    MYGYDGKVLRINLKERTCKSENLDLDKAKKFIGCRGLGVKTLFDEIDPKIDALSPENKFIIVTGPLTGAPVPTSGRFMVV
CRAGSAOR2    MYGYNGKVLRINLKERTCKSENLDLDKAKKFIGCRGLGVKTLFDEIDPKIDALSPENKFIIVTGPLTGAPVPTSGRFMVV
             ****:***************************************************************************

CAUTOAOR2    TKAPLTGTIGISNSGGKWGVDLKKAGWDMIIVEDKADSPVYIEIVDDKVEIKDASQLWGKVTSETTKELEKITENKSKVL
CLJUNAOR2    TKAPLTGTIGISNSGGKWGVDLKKAGWDMIIVEDKADSPVYIEIVDDKVEIKDASQLWGKVTSETTKELEKITENKSKVL
CRAGSAOR2    TKAPLTGTIGISNSGGKWGVDLKKAGWDMIIVEDKADSPVYIEIVDDKVEIKDASQLWGKVTSETTKELEKITENRSKVL
             ***********************************************************************:****

CAUTOAOR2    CIGPAGERLSLMAAVMNDVDRTAARGGVGAVMGSKNLKAITVKGTGKIALADKEKVKKVSVEKITTLKNDPVAGQGMPTY
CLJUNAOR2    CIGPAGERLSLMAAVMNDVDRTAARGGVGAVMGSKNLKAITVKGTGKIALADKEKVKKVSVEKITTLKNDPVAGQGMPTY
CRAGSAOR2    CIGPAGERLSLMAAVMNDVDRTAARGGVGAVMGSKNLKAITVKGTGKIALADKEKVKKVSVEKITTLKNDPVAGQGMPTY
             ********************************************************************************

CAUTOAOR2    GTAILVNIINENGVHPVKNFQESYTNQADKISGETLTANQLVRKNPCYSCPIGCGRWVRLKDGTECGGPEYETLWCFGSD
CLJUNAOR2    GTAILVNIINENGVHPVKNFQESYTNQADKISGETLTANQLVRKNPCYSCPIGCGRWVRLKDGTECGGPEYETLWCFGSD
CRAGSAOR2    GTAILVNIINENGVHPVNNFQESYTDQADKISGETLTANQLVRKNPCYSCPIGCGRWVRLKDGTECGGPEYETLWCFGSD
             *****************:*******:******************************************************

CAUTOAOR2    CGSYDLDAINEANMLCNEYGIDTITCGATIAAAMELYQRGYIKDEEIAGDNLSLKWGDTESMIGWIKRMVYSEGFGAKMT
CLJUNAOR2    CGSYDLDAINEANMLCNEYGIDTITCGATIAAAMELYQRGYIKDEEIAGDNLSLKWGDTESMIGWIKRMVYSEGFGAKMT
CRAGSAOR2    CGSYDLDAINEANMLCNEYGIDTITCGATIAAAMELYQRGYVKDEEIAGDNLSLKWGDTESMIGWIKKMVYSEGFGAKMT
             ****************************************:**************************:***********

CAUTOAOR2    NGSYRLCEGYGAPEYSMTVKKQEIPAYDPRGIQGHGITYAVNNRGGCHIKGYMINPEILGYPEKLDRFALDGKAAYAKLF
CLJUNAOR2    NGSYRLCEGYGAPEYSMTVKKQEIPAYDPRGIQGHGITYAVNNRGGCHIKGYMINPEILGYPEKLDRFALDGKAAYAKLF
CRAGSAOR2    NGSYRLCEGYGVPEYSMTVKKQEIPAYDPRGIQGHGITYAVNNRGGCHIKGYMINPEILGYPEKLDRFALDGKAAYAKMM
             ***********.***************************************************************::

CAUTOAOR2    HDLTAVIDSLGLCIFTTFGLGIQDYVDMYNAVVGESTYDADSLLEAGDRIWTLEKLFNLAAGIDSSQDTLPKRLLEEPIP
CLJUNAOR2    HDLTAVIDSLGLCIFTTFGLGIQDYVDMYNAVVGESTYDADSLLEAGDRIWTLEKLFNLAAGIDSSQDTLPKRLLEEPIP
CRAGSAOR2    HDLTAVIDSLGLCIFTTFGLGIQDYVDMYNAVVGESTCDSDSLLEAGDRVWTLEKLFNLAAGIDSSQDTLPKRLLEEPIP
             ************************************ *:*******:********************************

CAUTOAOR2    DGPSKGEVHRLDVLLPEYYSVRGWSKEGIPTEETLKKLGLDEYIGKF
CLJUNAOR2    DGPSKGEVHRLDVLLPEYYSVRGWSKEGIPTEETLKKLGLDEYIGKF
CRAGSAOR2    DGPSKGHVHRLDVLLPEYYSVRGWSKEGIPTEETLKKLGLDEYIGKF
             ******.****************************************
```

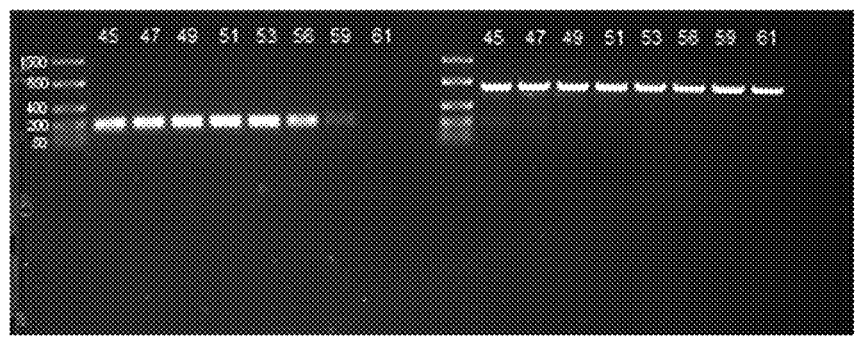
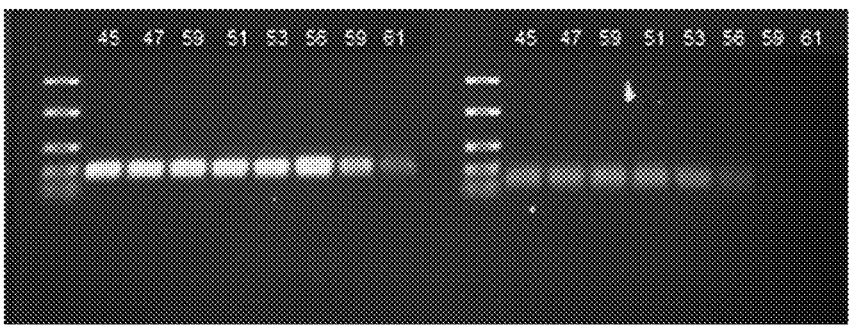
Fig 8A AOR1-A  Fig 8B BCoAAT
Fig 8C AOR2-A  Fig 8D Buk

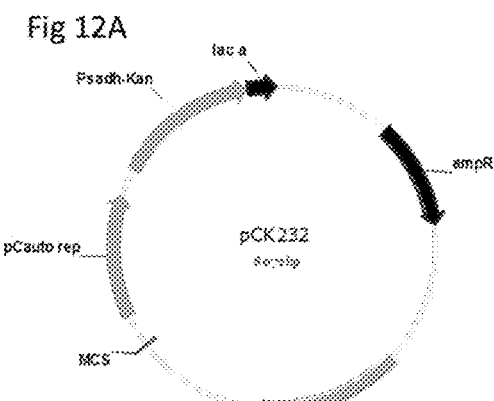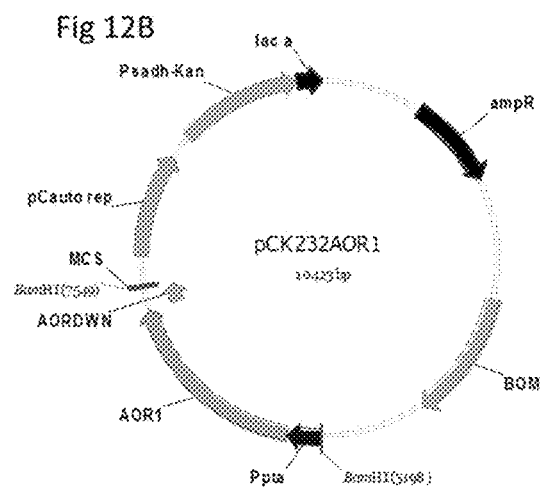

AOR Expression Syngas

AOR Expression Fructose

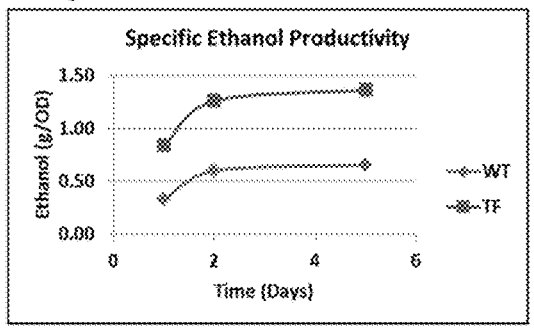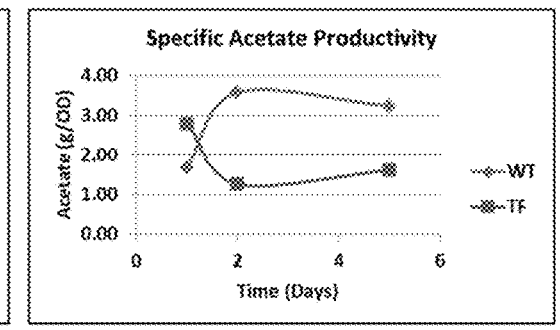

SEQUENCE LISTING

<160> NUMBER OF SEQ ID NOS: 34

<210> SEQ ID NO 1
<211> LENGTH: 1962
<212> TYPE: DNA
<213> ORGANISM: Clostridium autoethanogenum

<400> SEQUENCE: 1

```
tctgaaatgg aacaaaattg caccaagatg aacagtttg cttggcgcaa taccctcaaa      60
acacaatatt ttattattgg catggtttat gctatatata taattgtttg aataatcaat    120
ttttttagga gggtttttat gtacggatat aagggtaagg tattaagaat taatctaagt    180
agtaaaactt atatagtgga agaattgaaa attgacaaag ctaaaaaatt tataggtgca    240
agagggttag gcgtaaaaac cttatttgac gaagtagatc caaaggtaga tccattatca    300
```

```
cctgataaca aatttattat agcagcggga ccacttacag gtgcacctgt tccaacaagc    360
ggaagattca tggtagttac taaatcacct ttaacaggaa ctattgctat tgcaaattca    420
ggtggaaaat ggggagcaga attcaaagca gctggatacg atatgataat cgttgaaggt    480
aaatctgata agaagttta tgtaaatata gtagatgata agtagaatt tagggatgct      540 tctcatgttt ggggaaaact aacagaagaa actacaaaaa tgcttcaaca ggaaacagat    600
tcgagagcta aggttttatg cataggacca gctggggaaa agttatcact tatggcagca    660
gttatgaatg atgttgatag aacagcagga cgtggtggtg ttggagctgt tatgggttca    720
aagaacttaa aagctattgt agttaaagga agcggaaaag taaaattatt tgatgaacaa    780
aaagtgaagg aagtagcact tgagaaaaca aatattttaa gaaaagatcc agtagctggt    840
ggaggacttc caacatacgg aacagctgta cttgttaata ttataaatga aaatggtgta    900
catccagtaa agaattttca aaaatcttat acagatcaag cagataagat cagtggagaa    960
actttaacta aagattgctt agttagaaaa aatccttgct ataggtgtcc aattgcctgt    1020
ggaagatggg taaaacttga tgatggaact gaatgtggag gaccagaata tgaaacatta    1080
tggtcatttg gatctgattg tgatgtatac gatataaatg ctgtaaatac agcaaatatg    1140
ttgtgtaatg aatatggact agataccatt acagcaggat gtactattgc agcagctatg    1200
gaactttatc aaagaggtta tattaaggat gaagaaatag cagcagatgg attgtcactt    1260
aattggggag atgctaagtc catggttgaa tgggtaaaga aaatgggact tagagaagga    1320
tttggagaca agatggcaga tggttcatac agactttgtg actcatacgg tgtacctgag    1380
tattcaatga ctgtaaaaaa acaggaactt ccagcatatg acccaagagg aatacaggga    1440
catggcatta cttatgctgt taacaatagg ggaggatgtc acattaaggg atatatggta    1500
agtcctgaaa tacttggcta tccagaaaaa cttgatagac ttgcagtgga aggaaaagca    1560
ggatatgcta gagtattcca tgatttaaca gctgttatag attcacttgg attatgtatt    1620
tttacaacat ttggtcttgg tgcacaggat tatgttgata tgtataatgc agtagttggt    1680
ggagaattac atgatgtaaa ttctttaatg ttagctggag atagaatatg gactttagaa    1740
aaaatattta acttaaaagc aggcatagat agttcacagg atactcttcc aaagagattg    1800
cttgaagaac aaattccaga aggaccatca aaaggagaag ttcataagtt agatgtacta    1860
ctacctgaat attattcagt acgtggatgg gataaaaatg gtattcctac agaggaaacg    1920
ttaaagaaat taggattaga tgaatacgta ggtaagcttt ag                      1962

<210> SEQ ID NO 2
<211> LENGTH: 607
<212> TYPE: PRT
<213> ORGANISM: Clostridium autoethanogenum

<400> SEQUENCE: 2

Met Tyr Gly Tyr Lys Gly Lys Val Leu Arg Ile Asn Leu Ser Ser Lys
1               5                   10                  15

Thr Tyr Ile Val Glu Glu Leu Lys Ile Asp Lys Ala Lys Lys Phe Ile
                20                  25                  30

Gly Ala Arg Gly Leu Gly Val Lys Thr Leu Phe Asp Glu Val Asp Pro
            35                  40                  45

Lys Val Asp Pro Leu Ser Pro Asp Asn Lys Phe Ile Ile Ala Ala Gly
        50                  55                  60

Pro Leu Thr Gly Ala Pro Val Pro Thr Ser Gly Arg Phe Met Val Val
65                  70                  75                  80
```

-continued

Thr Lys Ser Pro Leu Thr Gly Thr Ile Ala Ile Ala Asn Ser Gly Gly
                85                  90                  95

Lys Trp Gly Ala Glu Phe Lys Ala Ala Gly Tyr Asp Met Ile Ile Val
            100                 105                 110

Glu Gly Lys Ser Asp Lys Glu Val Tyr Val Asn Ile Val Asp Asp Lys
        115                 120                 125

Val Glu Phe Arg Asp Ala Ser His Val Trp Gly Lys Leu Thr Glu Glu
    130                 135                 140

Thr Thr Lys Met Leu Gln Gln Glu Thr Asp Ser Arg Ala Lys Val Leu
145                 150                 155                 160

Cys Ile Gly Pro Ala Gly Glu Lys Leu Ser Leu Met Ala Ala Val Met
                165                 170                 175

Asn Asp Val Asp Arg Thr Ala Gly Arg Gly Val Gly Ala Val Met
            180                 185                 190

Gly Ser Lys Asn Leu Lys Ala Ile Val Val Lys Gly Ser Gly Lys Val
        195                 200                 205

Lys Leu Phe Asp Glu Gln Lys Val Lys Glu Val Ala Leu Glu Lys Thr
    210                 215                 220

Asn Ile Leu Arg Lys Asp Pro Val Ala Gly Gly Leu Pro Thr Tyr
225                 230                 235                 240

Gly Thr Ala Val Leu Val Asn Ile Ile Asn Glu Asn Gly Val His Pro
                245                 250                 255

Val Lys Asn Phe Gln Lys Ser Tyr Thr Asp Gln Ala Asp Lys Ile Ser
            260                 265                 270

Gly Glu Thr Leu Thr Lys Asp Cys Leu Val Arg Lys Asn Pro Cys Tyr
        275                 280                 285

Arg Cys Pro Ile Ala Cys Gly Arg Trp Val Lys Leu Asp Asp Gly Thr
    290                 295                 300

Glu Cys Gly Gly Pro Glu Tyr Glu Thr Leu Trp Ser Phe Gly Ser Asp
305                 310                 315                 320

Cys Asp Val Tyr Asp Ile Asn Ala Val Asn Thr Ala Asn Met Leu Cys
                325                 330                 335

Asn Glu Tyr Gly Leu Asp Thr Ile Thr Ala Gly Cys Thr Ile Ala Ala
            340                 345                 350

Ala Met Glu Leu Tyr Gln Arg Gly Tyr Ile Lys Asp Glu Glu Ile Ala
        355                 360                 365

Ala Asp Gly Leu Ser Leu Asn Trp Gly Asp Ala Lys Ser Met Val Glu
    370                 375                 380

Trp Val Lys Lys Met Gly Leu Arg Glu Gly Phe Gly Asp Lys Met Ala
385                 390                 395                 400

Asp Gly Ser Tyr Arg Leu Cys Asp Ser Tyr Gly Val Pro Glu Tyr Ser
                405                 410                 415

Met Thr Val Lys Lys Gln Glu Leu Pro Ala Tyr Asp Pro Arg Gly Ile
            420                 425                 430

Gln Gly His Gly Ile Thr Tyr Ala Val Asn Asn Arg Gly Gly Cys His
        435                 440                 445

Ile Lys Gly Tyr Met Val Ser Pro Glu Ile Leu Gly Tyr Pro Glu Lys
    450                 455                 460

Leu Asp Arg Leu Ala Val Glu Gly Lys Ala Gly Tyr Ala Arg Val Phe
465                 470                 475                 480

His Asp Leu Thr Ala Val Ile Asp Ser Leu Gly Leu Cys Ile Phe Thr
                485                 490                 495

Thr Phe Gly Leu Gly Ala Gln Asp Tyr Val Asp Met Tyr Asn Ala Val

```
                500              505              510
Val Gly Gly Glu Leu His Asp Val Asn Ser Leu Met Leu Ala Gly Asp
            515                  520              525

Arg Ile Trp Thr Leu Glu Lys Ile Phe Asn Leu Lys Ala Gly Ile Asp
        530                  535              540

Ser Ser Gln Asp Thr Leu Pro Lys Arg Leu Leu Glu Glu Gln Ile Pro
545                  550                  555                  560

Glu Gly Pro Ser Lys Gly Glu Val His Lys Leu Asp Val Leu Leu Pro
                565                  570                  575

Glu Tyr Tyr Ser Val Arg Gly Trp Asp Lys Asn Gly Ile Pro Thr Glu
            580                  585                  590

Glu Thr Leu Lys Lys Leu Gly Leu Asp Glu Tyr Val Gly Lys Leu
        595                  600                  605

<210> SEQ ID NO 3
<211> LENGTH: 2106
<212> TYPE: DNA
<213> ORGANISM: Clostridium autoethanogenum

<400> SEQUENCE: 3
aaatagtatt gtacgttatt tgatcacttt tttaaaaata aaatgataat attgtatttt     60
ttttgagcat tttggcaata caaagaactg tattgtttat tatttaagca ttttattata    120
aaacaaaaaa acgttattaa attatttgct atgaattcac ttgataatca atgcattgca    180
tgtgatgttg attattgagt gttttttttg taaccatatt tggcacaatt tatgctctat    240
aatatttctg aaataaatac atttatatga ggaggaattt caatgtatgg ttatgatggt    300
aaagtattaa gaattaattt aaaagaaaga acttgcaaat cagaaaattt agatttagat    360
aaagctaaaa agtttatagg ttgtagggga ctaggtgtta aaactttatt tgatgaaata    420
gatcctaaaa tagatgcatt atcaccagaa ataaattta taattgtaac aggtccttta    480
actggagctc cggttccaac tagtggaagg tttatggtag ttactaaagc accgcttaca    540
ggaactatag gaatttcaaa ttcgggtgga aaatggggag tagacttaaa aaaagctggt    600
tgggatatga taatagtaga ggataaggct gattcaccag tttacattga aatagtagat    660
gataaggtag aaattaaaga cgcgtcacag ctttgggaa aagttacatc agaaactaca    720
aaagagttag aaaagataac tgagaataaa tcaaaggtat tatgtatagg acctgctggt    780
gaacgattgt ctcttatggc agcagttatg aatgatgtag atagaactgc agcaagaggc    840
ggcgttggtg cagttatggg atctaaaaac ttaaagcta ttacagttaa ggaactgga    900 aaaatagctt tagctgataa agaaaagta aaaaagtgt ccgtagaaaa aattacaaca    960
ttaaaaaatg atccagtagc tggtcaggga atgccaactt atggtacagc tatactggtt   1020
aatataataa atgaaaatgg agttcatcct gtaaagaatt ttcaagagtc ttatacgaat   1080
caagcagata aaataagtgg agagactctt actgctaacc aactagtaag gaaaaatcct   1140
tgttacagct gtcctatagg ttgtggaaga tgggttagac taaaagatgg cacagagtgc   1200
ggaggaccag aatatgaaac actgtggtgt tttggatctg actgtggttc atatgattta   1260
gatgctataa atgaagctaa tatgttatgt aatgaatatg gtattgatac tattacttgt   1320
ggtgcaacaa ttgctgcagc tatggaactt tatcaaagag atatataaa agacgaagaa   1380 atagctggag ataacctatc tctcaagtgg ggtgatacgg aatctatgat tggctggata   1440
aagagaatgg tatatagtga aggctttgga gcaaagatga caaatggttc atataggctt   1500
tgtgaaggtt atgagcacc ggagtattct atgacagtta aaaagcagga aattccagca   1560
```

-continued

```
tatgatccaa ggggaataca gggacacggt attacctatg cagttaataa tagaggaggc    1620
tgtcatatta agggatacat gattaaccct gaaatattag gttatcctga aaaacttgat    1680
agatttgcat tagatggtaa agcagcttat gccaaattat ttcatgattt aactgctgta    1740
attgattctt taggattgtg catattcact acatttgggc ttggaataca ggattatgta    1800
gatatgtata atgcagtagt aggagaatct acttatgatg cagattcact attagaggca    1860
ggagatagaa tctggactct tgagaaatta tttaatcttg cagctggaat agacagcagc    1920
caggatactc taccaaagag attgttagaa gaacctattc cagatggccc atcaaaggga    1980
gaagttcata ggctagatgt tcttctgcca gaatattact cagtacgagg atggagtaaa    2040
gagggtatac ctacagaaga aacattaaag aaattaggat tagatgaata tataggtaag    2100
ttctag                                                              2106
```

<210> SEQ ID NO 4
<211> LENGTH: 607
<212> TYPE: PRT
<213> ORGANISM: Clostridium autoethanogenum

<400> SEQUENCE: 4

```
Met Tyr Gly Tyr Asp Gly Lys Val Leu Arg Ile Asn Leu Lys Glu Arg
1               5                   10                  15

Thr Cys Lys Ser Glu Asn Leu Asp Leu Asp Lys Ala Lys Lys Phe Ile
            20                  25                  30

Gly Cys Arg Gly Leu Gly Val Lys Thr Leu Phe Asp Glu Ile Asp Pro
        35                  40                  45

Lys Ile Asp Ala Leu Ser Pro Glu Asn Lys Phe Ile Ile Val Thr Gly
    50                  55                  60

Pro Leu Thr Gly Ala Pro Val Pro Thr Ser Gly Arg Phe Met Val Val
65                  70                  75                  80

Thr Lys Ala Pro Leu Thr Gly Thr Ile Gly Ile Ser Asn Ser Gly Gly
                85                  90                  95

Lys Trp Gly Val Asp Leu Lys Lys Ala Gly Trp Asp Met Ile Ile Val
            100                 105                 110

Glu Asp Lys Ala Asp Ser Pro Val Tyr Ile Glu Ile Asp Asp Lys
        115                 120                 125

Val Glu Ile Lys Asp Ala Ser Gln Leu Trp Gly Lys Val Thr Ser Glu
    130                 135                 140

Thr Thr Lys Glu Leu Glu Lys Ile Thr Glu Asn Lys Ser Lys Val Leu
145                 150                 155                 160

Cys Ile Gly Pro Ala Gly Glu Arg Leu Ser Leu Met Ala Ala Val Met
                165                 170                 175

Asn Asp Val Asp Arg Thr Ala Ala Arg Gly Gly Val Gly Ala Val Met
            180                 185                 190

Gly Ser Lys Asn Leu Lys Ala Ile Thr Val Lys Gly Thr Gly Lys Ile
        195                 200                 205

Ala Leu Ala Asp Lys Glu Lys Val Lys Val Ser Val Glu Lys Ile
    210                 215                 220

Thr Thr Leu Lys Asn Asp Pro Val Ala Gly Gln Gly Met Pro Thr Tyr
225                 230                 235                 240

Gly Thr Ala Ile Leu Val Asn Ile Ile Asn Glu Asn Gly Val His Pro
                245                 250                 255

Val Lys Asn Phe Gln Glu Ser Tyr Thr Asn Gln Ala Asp Lys Ile Ser
            260                 265                 270
```

Gly Glu Thr Leu Thr Ala Asn Gln Leu Val Arg Lys Asn Pro Cys Tyr
            275                 280                 285

Ser Cys Pro Ile Gly Cys Gly Arg Trp Val Arg Leu Lys Asp Gly Thr
290                 295                 300

Glu Cys Gly Gly Pro Glu Tyr Glu Thr Leu Trp Cys Phe Gly Ser Asp
305                 310                 315                 320

Cys Gly Ser Tyr Asp Leu Asp Ala Ile Asn Glu Ala Asn Met Leu Cys
            325                 330                 335

Asn Glu Tyr Gly Ile Asp Thr Ile Thr Cys Gly Ala Thr Ile Ala Ala
            340                 345                 350

Ala Met Glu Leu Tyr Gln Arg Gly Tyr Ile Lys Asp Glu Ile Ala
            355                 360                 365

Gly Asp Asn Leu Ser Leu Lys Trp Gly Asp Thr Glu Ser Met Ile Gly
370                 375                 380

Trp Ile Lys Arg Met Val Tyr Ser Glu Gly Phe Gly Ala Lys Met Thr
385                 390                 395                 400

Asn Gly Ser Tyr Arg Leu Cys Glu Gly Tyr Gly Ala Pro Glu Tyr Ser
            405                 410                 415

Met Thr Val Lys Lys Gln Glu Ile Pro Ala Tyr Asp Pro Arg Gly Ile
            420                 425                 430

Gln Gly His Gly Ile Thr Tyr Ala Val Asn Asn Arg Gly Gly Cys His
            435                 440                 445

Ile Lys Gly Tyr Met Ile Asn Pro Glu Ile Leu Gly Tyr Pro Glu Lys
            450                 455                 460

Leu Asp Arg Phe Ala Leu Asp Gly Lys Ala Ala Tyr Ala Lys Leu Phe
465                 470                 475                 480

His Asp Leu Thr Ala Val Ile Asp Ser Leu Gly Leu Cys Ile Phe Thr
            485                 490                 495

Thr Phe Gly Leu Gly Ile Gln Asp Tyr Val Asp Met Tyr Asn Ala Val
            500                 505                 510

Val Gly Glu Ser Thr Tyr Asp Ala Asp Ser Leu Leu Glu Ala Gly Asp
            515                 520                 525

Arg Ile Trp Thr Leu Glu Lys Leu Phe Asn Leu Ala Ala Gly Ile Asp
530                 535                 540

Ser Ser Gln Asp Thr Leu Pro Lys Arg Leu Leu Glu Glu Pro Ile Pro
545                 550                 555                 560

Asp Gly Pro Ser Lys Gly Glu Val His Arg Leu Asp Val Leu Leu Pro
            565                 570                 575

Glu Tyr Tyr Ser Val Arg Gly Trp Ser Lys Gly Ile Pro Thr Glu
            580                 585                 590

Glu Thr Leu Lys Lys Leu Gly Leu Asp Glu Tyr Ile Gly Lys Phe
            595                 600                 605

<210> SEQ ID NO 5
<211> LENGTH: 2329
<212> TYPE: DNA
<213> ORGANISM: Clostridium autoethanogenum

<400> SEQUENCE: 5
gaattctgat tgattattta ttttaaaatg cctaagtgaa atatatacat attataacaa     60
taaaataagt attagtgtag gatttttaaa tagagtatct attttcagat taaattttg    120 attatttgat ttacattata taatattgag taaagtattg actagcaaaa ttttttgata   180
ctttaatttg tgaaatttct tatcaaaagt tatattttg aataattttt attgaaaaat    240

```
acaactaaaa aggattatag tataagtgtg tgtaattttg tgttaaattt aaagggagga    300
aaatgtatgg ttatgatggt aaagtattaa gaattaattt aaaagaaaga acttgcaaat    360
cagaaaattt agatttagat aaagctaaaa agtttatagg ttgtagggga ctaggtgtta    420
aaactttatt tgatgaaata gatcctaaaa tagatgcatt atcaccagaa ataaattta     480 taattgtaac aggtcctttta actggagctc cggttccaac tagtggaagg tttatggtag   540
ttactaaagc accgcttaca ggaactatag gaatttcaaa ttcgggtgga aaatggggag    600
tagacttaaa aaaagctggt tgggatatga taatagtaga ggataaggct gattcaccag    660
tttacattga aatagtagat gataaggtag aaattaaaga cgcgtcacag ctttggggaa    720
aagttacatc agaaactaca aaagagttag aaaagataac tgagaataaa tcaaaggtat    780
tatgtatagg acctgctggt gaacgattgt ctcttatggc agcagttatg aatgatgtag    840
atagaactgc agcaagaggc ggcgttggtg cagttatggg atctaaaaac ttaaaagcta    900
ttacagttaa aggaactgga aaaatagctt tagctgataa agaaaaagta aaaaaagtgt    960
ccgtagaaaa aattacaaca ttaaaaaatg atccagtagc tggtcaggga atgccaactt   1020
atggtacagc tatactggtt aatataataa atgaaaatgg agttcatcct gtaaagaatt   1080
ttcaagagtc ttatacgaat caagcagata aaataagtgg agagactctt actgctaacc   1140
aactagtaag gaaaaatcct tgttacagct gtcctatagg ttgtggaaga tgggttagac   1200
taaaagatgg cacagagtgc ggaggaccag aatatgaaac actgtggtgt tttggatctg   1260
actgtggttc atatgattta gatgctataa atgaagctaa tatgttatgt aatgaatatg   1320
gtattgatac tattacttgt ggtgcaacaa ttgctgcagc tatggaactt tatcaaagag   1380
gatatataaa agacgaagaa atagctggag ataacctatc tctcaagtgg ggtgatacgg   1440
aatctatgat tggctggata aagagaatgg tatatagtga aggctttgga gcaaagatga   1500
caaatggttc atataggctt tgtgaaggtt atggagcacc ggagtattct atgacagtta   1560
aaaagcagga aattccagca tatgatccaa ggggaataca gggacacggt attacctatg   1620
cagttaataa tagaggaggc tgtcatatta agggatacat gattaaccct gaaatattag   1680
gttatcctga aaaacttgat agatttgcat tagatggtaa agcagcttat gccaaattat   1740 ttcatgatt aactgctgta attgattctt taggattgtg catattcact acatttgggc   1800
ttggaataca ggattatgta gatatgtata atgcagtagt aggagaatct acttatgatg   1860
cagattcact attagaggca ggagatagaa tctggactct tgagaaatta tttaatcttg   1920
cagctggaat agacagcagc caggatactc taccaaagag attgttagaa gaacctattc   1980
cagatggccc atcaaaggga gaagttcata ggctagatgt tcttctgcca gaatattact   2040
cagtacgagg atggagtaaa gagggtatac ctacagaaga aacattaaag aaattaggat   2100
tagatgaata tataggtaag ttctagtttg attcggtaaa ctagaaagca gactttatgt   2160
gttaaagaag atagcttctc tctatatatg aagtctgttt ttaatagaaa gatatgaatt   2220
tgagaataga agttagatta gttgcttata tatttgcaaa agtgttaagt tctgcttgga   2280
taagttcggg agatgaaatt tagttgttat gataaacttc aatgaattc                2329
```

<210> SEQ ID NO 6
<211> LENGTH: 2155
<212> TYPE: DNA
<213> ORGANISM: Clostridium autoethanogenum

<400> SEQUENCE: 6

```
gattcttagt ataagtattc ttagtatctt tagcacttag aatacgttat cctttaggag        60
aataatccta atcagtagtt ctaataattt aatagtatac ttaaatagta tattttggag       120
gttttattat gtatggttat gatggtaaag tattaagaat taatttaaaa gaaagaactt       180
gcaaatcaga aaatttagat ttagataaag ctaaaaagtt tataggttgt aggggactag       240
gtgttaaaac tttatttgat gaaatagatc ctaaaataga tgcattatca ccagaaaata       300
aatttataat tgtaacaggt cctttaactg gagctccggt tccaactagt ggaaggttta       360
tggtagttac taaagcaccg cttacaggaa ctataggaat ttcaaattcg ggtggaaaat       420
ggggagtaga cttaaaaaaa gctggttggg atatgataat agtagaggat aaggctgatt       480
caccagttta cattgaaata gtagatgata aggtagaaat taaagacgcg tcacagcttt       540
ggggaaaagt tacatcagaa actacaaaag agttagaaaa gataactgag aataaatcaa       600
aggtattatg tataggacct gctggtgaac gattgtctct tatggcagca gttatgaatg       660
atgtagatag aactgcagca agaggcggcg ttggtgcagt tatgggatct aaaaacttaa       720
aagctattac agttaaagga actggaaaaa tagctttagc tgataaagaa aaagtaaaaa       780
aagtgtccgt agaaaaaatt acaacattaa aaaatgatcc agtagctggt cagggaatgc       840
caacttatgg tacagctata ctggttaata taataaatga aaatggagtt catcctgtaa       900
agaattttca agagtcttat acgaatcaag cagataaaat aagtggagag actcttactg       960
ctaaccaact agtaaggaaa aatccttgtt acagctgtcc tataggttgt ggaagatggg      1020
ttagactaaa agatggcaca gagtgcggag gaccagaata tgaaacactg tggtgttttg      1080
gatctgactg tggttcatat gatttagatg ctataaatga agctaatatg ttatgtaatg      1140
aatatggtat tgatactatt acttgtggtg caacaattgc tgcagctatg aactttatc       1200 aaagaggata tataaaagac gaagaaatag ctggagataa cctatctctc aagtggggtg      1260
atacggaatc tatgattggc tggataaaga gaatggtata tagtgaaggc tttggagcaa      1320
agatgacaaa tggttcatat aggctttgtg aaggttatgg agcaccggag tattctatga      1380
cagttaaaaa gcaggaaatt ccagcatatg atccaagggg aatacaggga cacggtatta      1440
cctatgcagt taataataga ggaggctgtc atattaaggg atacatgatt aaccctgaaa      1500
tattaggtta tcctgaaaaa cttgatagat ttgcattaga tggtaaagca gcttatgcca      1560
aattatttca tgatttaact gctgtaattg attcttagg attgtgcata ttcactacat       1620
ttgggcttgg aatacaggat tatgtagata tgtataatgc agtagtagga gaatctactt      1680
atgatgcaga ttcactatta gaggcaggag atagaatctg gactcttgag aaattatttta     1740 atcttgcagc tggaatagac agcagccagg atactctacc aaaagagattg ttagaagaac    1800 ctattccaga tggcccatca aagggagaag ttcataggct agatgttctt ctgccagaat     1860
attactcagt acgaggatgg agtaaagagg gtataccatc agaagaaaca ttaaagaaat     1920
taggattaga tgaatatata ggtaagttct agtttgattc ggtaaactag aaagcagact     1980
ttatgtgtta aagaagatag cttctctcta tatgaagt ctgttttta agaaagata         2040 tgaatttgag aatagaagtt agattagttg cttatatatt tgcaaaagtg ttaagttctg    2100
cttggataag ttcgggagat gaaatttagt tgttatgata aacttcaatg aattc          2155
```

<210> SEQ ID NO 7
<211> LENGTH: 1371
<212> TYPE: DNA
<213> ORGANISM: Clostridium pharus

<400> SEQUENCE: 7

```
atgaggaagg tgttttatt taaaatatta ataaattttt tggaaggggt tttaaaaatg        60 gttttaaaa attggcagga tctttataaa agtaaatttg ttagtgcaga tgaagctgta       120
tctaaggtaa actgtgggga tactatagtt ttaggtaatg cttgtggagc acctcttaca       180
cttttagatg ctttggctgc aaataaggaa aagtataaga gtgtacagat atataatctt       240
atactgaact ataaaagtga tatatatgct gaaccaggtg cagaaaagta tattcatgga       300 aatactttt ttgtaagtgg aggtactaag gaagctgtta attgtaacag aacagattat       360
accccatgct ttttttatga ataccaaaa ttaataaaac aaaaatatat acatatagat       420
gtagcattta ttcatgtaag taaacctgat aagcatggtt attgtagttt tggagtatca       480
actgattatt cacaggcaat ggtacagggt gctaaacttg taattgcaga agtaaacgat       540
caaatgccaa gagttttggg agacaatttt atacacattt ctgatattga ttacatagta       600
aagacttcac gcccaattct tgagttggca cctcctaaaa taggagaagt agaaaaaaca       660
ataggaaaat attgtgcatc tcttatagaa gatggttcta cacttcaact tggaataggc       720
gctattccag atgcagtact tttgtttttg aaagacaaaa aagatttggg aatacactca       780
gaaatgatat ctgatggtgt tgtagaatta gttgaatcag gagtaattac aaataagaaa       840
aaagctcttc atccaggaaa aataattgtt acattcttaa tgggaactaa aaaattatat       900
gattttatag atgataatcc tatggtagaa ggttatccag tagattatgt aaatgatcct       960
aaagttatta tgcaaaattc caagatggta tgtataaatt cttgtgtaga ggtagatttt      1020
acaggacagg tgtgtgctga agtatagga tttaagcaga taagcggagt aggcggacaa      1080
gttgattata tgagaggtgc tagcatgtct gatggaggaa aatcaattct tgctatacca      1140
tctactgcag ctggcggcaa aatttcaaga atagttccga tgttgactga aggagcagga      1200
gttactactt caagatatga tgttcaatat gttgttacag agtatggtat tgcacttctc      1260
aagggtaaat ccataagaga aagagctaaa gctcttataa acattgcaca tcctaaattt      1320
agagaacaat tagaaaaatc gtttgaagaa agatttagtt gtaaacttta a              1371
```

<210> SEQ ID NO 8
<211> LENGTH: 1314
<212> TYPE: DNA
<213> ORGANISM: Clostridium kluyveri

<400> SEQUENCE: 8

```
atggtttta aaaattggca ggatctttat aaaagtaaaa ttgttagtgc agacgaagct        60
gtatctaaag taagctgtgg agatagcata attttaggca atgcttgtgg agcatctctt       120
acacttttag atgccttggc tgcaaataag gaaaagtata agagtgtaaa gatacacaat       180
cttatactta attataaaaa tgatatatat actgatccgg aatcagaaaa gtatattcat       240
ggaaatactt tctttgtaag tggaggtaca aaggaagcag ttaattgtaa tagaacagat       300
tatactccat gctttttta tgaaatacca aaattattaa aacaaaagta tataaatgca       360
gatgtagctt ttattcaagt aagtaagcct gatagccatg gatactgtag ctttggagta       420
tcaaccgatt attcacaggc aatggtacag tctgcaaagc ttataattgc agaagtaaac       480
gatcagatgc caagagtttt aggagacaat tttatacaca tttctgatat ggattacata       540
gtagaaagtt cacgtccaat tctagaattg actcctccta aaataggaga agtagagaag       600
acaataggaa aatactgtgc atctcttgta gaagatggtt ctacacttca gcttggaata       660
ggagctattc cagatgcagt actttttattc ttgaaggata aaaaggattt gggtatacat       720
```

```
tcagaaatga tatccgatgg tgttgttgaa ttagttgaag caggggtaat tacaaataag    780
aaaaagtccc ttcatccagg aaaaataatt attacattct taatgggaac taagaaatta    840
tatgatttca taaatgataa tcctatggta gaaggatacc ctgtagatta tgtaaatgat    900
cctaaggtta ttatgcaaaa ttctaagatg gtatgtataa actcctgtgt agaagtggat    960
ttcacaggac aagtgtgtgc tgaaagtgta ggatttaaac aaataagcgg tgtaggtgga   1020
caagttgatt acatgagagg agctagcatg gctgatggag gaaaatcaat tcttgctata   1080
ccatctactg cagctggcgg caaaaatttca agaatagttc ctattttaac tgaaggagcg  1140
ggggttacta cttcaagata tgatgttcaa tatgttgtta cagaatatgg tattgcactt   1200
ctcaagggca aatccataag agaaagagct aaggagctta taaaaattgc acatcctaaa   1260
tttagggaag aattaacagc tcaatttgaa aaaagattca gttgtaagct ttaa         1314
```

<210> SEQ ID NO 9
<211> LENGTH: 1068
<212> TYPE: DNA
<213> ORGANISM: Clostridium carboxidivorans

<400> SEQUENCE: 9

```
atgagttata agatattagc aattaaccca ggatctactt ctacaaaaat agctttatac     60
gaagatgaaa aagaaatatt ttgcaaaacg ttagagcatc cagttgaaca aattgaaaaa    120
tatgagaatg tggcagatca atttgatatg agaaaagaag ttgttctttc atttttaaag    180
caaaatggat atgaagttaa agaattagct gcagttgttg gaagaggtgg aatggttcca    240
aaagtaaaat ctggagctta taaagttaat gaaacaatgg tagatagatt aaaaaataat    300
ccagtagtag aacatgcttc aaatttagga gctttaattg cttatgaaat agcaaattct    360
attggagtat cagcctatat atatgactct gttagagtag atgaattaga ggatatagct    420
cgtatatcag gtatgccgga tataccaaga acaagtacta gtcatgcatt aaatacaagg    480
gcaatggcaa tgaaggttgc aaaaaattat ggtaaaaagt attcagatat gaactttatt    540
gtagctcatc taggtggagg aatatcagta aatgttcata gaaaaggaca aatggtagat    600
ataatggcag atgacgaagg accattttca cctgaaagag ctggaaaagt tccttgcaat    660
gcacttatag atctttgcta ttcaggaaaa tttgataaaa aaactacgaa gaaaaaatta    720
aggggaaatg gtggattaaa agcttatctt aacactgttg atgctagaga agttgaaaga    780
atgattgaaa gtggagatga aaaagcaaag cttgtttatg aagctatggc ttatcaggtt    840
gctaagggaa taggagaact tgcaacagta gtagaaggta aggttgatgc tatcgttatt    900
acaggaggta tagcatattc tgatatgata actaactgga ttaaaaagcg tgtagagttt    960
attgcgcctg ttgagattat gcctggtgaa aatgaaatgg aatctttggc tttgggaact   1020
cttagagtgt taaagggtga agaagaagca agagaatatg ttgaataa                1068
```

<210> SEQ ID NO 10
<211> LENGTH: 1113
<212> TYPE: DNA
<213> ORGANISM: Clostridium carboxidivorans

<400> SEQUENCE: 10

```
ttgctaatta aaatatttat taagtattgc tataatcagg agggtaaaat aatgtacaaa     60
atactagcaa taaatccagg ttcaacttca actaaaatag ctatttatga tgacacagag    120
gaattattta aaaccactat agaacattct agtgaagaag tgaaaaaata tgaaaacata    180
gctgatcaat atagtatgag atatgaagct ataatgaaat ttttaaaaga agtagatttt    240
```

```
gatgtcaaag ctttatctgc agtagttgga agaggaggaa ttctgcctcc agttaaatca      300
ggagcttaca gagtaaatga ttctatggta gaaagactgg ctaaaagacc tgtagtagag      360
catgcttcaa atttaggagc tataatttca tatgcaatag caaaaccttt aaatatacca      420
gctttcatat atgattctgt agctgtagat gaatttgagg atattgcaag aatatcagga      480
cttgcagata taaaaagaga gagttttatt catgctttaa atatgagagc tgcagcaata      540
aaaacagcaa aaaactagg taaaccttat gaacaatgta atttagttgt tgctcattta      600
ggaggcggaa tatctcttac tgtacataaa ggtggaaaaa tgatagacgc tgttactgat      660
gaagaaggac cgtttttcacc agaaaggtca ggtagagtac cttgtaagcg cttaatagaa      720
atgtgttata aaaatgatga acgcacaatg aaaagaaaaa taagaggaga tggtggatta      780
atctcttatt taggaactaa tagtgcatta gatgtagaaa aaagaattga aaatggagat      840
gctgaagcca aattagttta tgaagctatg gcatatcaaa ttgcaaaagc aataggagaa      900
cttgcaactg tagtaaaggg aaaggttgat gcagtagtaa ttacagggggg aattgcctat      960 tcaaaaatga tgacaggatg gataaaagaa agagtagaat ttatagcacc tgtagagata     1020
ttgccaggag aaaatgaatt agaatctctt gctttaggta cgcttagagt tataaaggga     1080
gaagaaaaag cacacgaata tgatttagat tag                                  1113

<210> SEQ ID NO 11
<211> LENGTH: 1071
<212> TYPE: DNA
<213> ORGANISM: Clostridium carboxidivorans

<400> SEQUENCE: 11
atgtcatata aattattaat attaaatcca ggatctacat ctaccaaaat aggagtatat       60
gatggagaaa atgaaatttt agaagaaact ttaagacatt cttcagaaga aattgagaaa      120
tatgctacta tttatgatca atttgaattt agaaaagaag ttatattgaa ggttttaaaa      180
gaaaagaatt ttgatattaa tacattagac ggagtagtag gcagaggtgg attattaaaa      240
ccaattgaaa gtggaactta taagtcaat gatgctatgt tagaagacct aaaagttgga      300
gtgcaaggac agcatgcttc aaatttaggt ggaataatag ctaatgaaat aggaaaatct      360
ataaataaac cagcatttat agtagaccca gttgttgttg atgaattaga tgaagcagct      420
agaatatccg gaatgcctga aatagaaaga taagtatat tccatgcttt aaatcaaaaa      480
gcagtagcaa agagatatgc aaaagaaaac aataagaagt atgatgaatt aaatttagta      540
gtgacacaca tgggtggcgg agtaactgtt ggagctcaca aaaaaggaag agttgtagat      600
gtagccaatg gtttagatgg agatggacca ttttcaccag aaagaacagg aggacttcct      660
gtaggaggtt taataaagct ttgctatagt ggaaaatata ctttagaaga aatgaagaaa      720
aagataagtg gaaaggtgg aattgtagct tatctaaata caaatgattt tagggaagta      780 gaacaaaag cagaaagtgg agataaaaag gcaaagttag tatttgatgc tttcatatta      840
caagtaggta aagaaattgg taaatgtgct gcagttttac atggaaaagt agatgcttta      900 atttaactg gaggaataagc ttatagtaaa actgttacag ctgcaataaa agacatggta      960
gaatttattg caccagttgt agtttatcca ggagaagatg aattattagc attagcacaa     1020
ggcggactta gagtactagg tggagaagaa caagcaaaag aatataagta a              1071

<210> SEQ ID NO 12
<211> LENGTH: 1068
<212> TYPE: DNA
```

<213> ORGANISM: Clostridium difficile

<400> SEQUENCE: 12

```
atgacttaca gaatattagc cataaatcca ggttctactt ctacaaaaat agcagtatat      60
gatggagaag aacaaattct tgtgaagacg atagaccatc cggctgaaga gattgcaaaa     120
tataatacta tacaagacca gtttgaaatg cgtaaggaag cagttttgaa tattcttaaa     180
gaaaatagta tagacttaaa atctcttagt gcaatagtag gaagaggtgg agttttacca     240
ccagtaaaat caggagcata tttagtaaat gaagaaatga ttgatgtact aagacataga     300
ccagtacttg aacacgcttc caatttaggt gctgttgtgg cacatgcaat atcagaacct     360
cttggaatca actcatatat ttatgattct gttgcagtag atgagcttat agatgtagcg     420
agaatatctg actttgtgg aatggataga tcaagtgcag gcatgcatt aaatactaga       480
gcaatggctt taaaatatgc taaggataaa ggaaaagatt ataagagctt aaacttaata    540
gtagctcaca ttggtggagg agtaagtatt tatcttcatg aaaaaggaag aatggttgat    600
atgctatctg atgatgaagg accatttct ccagaaaggt caggaagagt acctgctaca    660
aaattagtgg ctgcctgtta ttcaggtcaa tattcagaaa gagaaatgac taaaaagata    720
agaggtaaag gtggtatagt ttcataccta aatactgtag atgctagaga agttgaaaaa   780
atgatagcag aaggaaatga agaagcaaaa attatttatg aagcaatggc ttatcagtta    840
gcaaaaggta ttggagagtt agcaactgta gtagatggaa aggtagatgc tataattata    900
acaggtggaa ttgcatattc tgaaatgttt acttcaatgg ttaaaagaa agttgagttt     960
atagcaccag tagaaattat ggcaggagaa atgagttgg ataatcactt gcttttggaa    1020
ctttaagagt actaaatgga gaagaagaag ctagaattta tagtgaaa               1068
```

<210> SEQ ID NO 13
<211> LENGTH: 172
<212> TYPE: DNA
<213> ORGANISM: Clostridium autoethanogenum

<400> SEQUENCE: 13

```
acttggatta tgtatttta caacatttgg tcttggtgca caggattatg ttgatatgta      60
taatgcagta gttggtggag aattacatga tgtaaattct ttaatgttag ctggagatag   120
aatatggact ttagaaaaaa tatttaactt aaaagcaggc atagatagtt ca             172
```

<210> SEQ ID NO 14
<211> LENGTH: 170
<212> TYPE: DNA
<213> ORGANISM: Clostridium autoethanogenum

<400> SEQUENCE: 14

```
aagaaagaac ttgcaaatca gaaaatttag atttagataa agctaaaaag tttataggtt      60
gtagggact aggtgttaaa actttatttg atgaaataga tcctaaaata gatgcattat    120
caccagaaaa taaatttata attgtaacag gtcctttaac tggagctccg               170
```

<210> SEQ ID NO 15
<211> LENGTH: 607
<212> TYPE: PRT
<213> ORGANISM: Clostridium ljungdahlii

<400> SEQUENCE: 15

Met Tyr Gly Tyr Lys Gly Lys Val Leu Arg Ile Asn Leu Ser Ser Lys
1               5                   10                  15

-continued

```
Thr Tyr Ile Val Glu Glu Leu Lys Ile Asp Lys Ala Lys Lys Phe Ile
             20                  25                  30
Gly Ala Arg Gly Leu Gly Val Lys Thr Leu Phe Asp Glu Val Asp Pro
         35                  40                  45
Lys Val Asp Pro Leu Ser Pro Asp Asn Lys Phe Ile Ile Ala Ala Gly
 50                  55                  60
Pro Leu Thr Gly Ala Pro Val Pro Thr Ser Gly Arg Phe Met Val Val
 65                  70                  75                  80
Thr Lys Ser Pro Leu Thr Gly Thr Ile Ala Ile Ala Asn Ser Gly Gly
                 85                  90                  95
Lys Trp Gly Ala Glu Phe Lys Ala Ala Gly Tyr Asp Met Ile Ile Val
                100                 105                 110
Glu Gly Lys Ser Asp Lys Glu Val Tyr Val Asn Ile Val Asp Asp Lys
            115                 120                 125
Val Glu Phe Arg Asp Ala Ser His Val Trp Gly Lys Leu Thr Glu Glu
            130                 135                 140
Thr Thr Lys Met Leu Gln Gln Glu Thr Asp Ser Arg Ala Lys Val Leu
145                 150                 155                 160
Cys Ile Gly Pro Ala Gly Glu Lys Leu Ser Leu Met Ala Ala Val Met
                165                 170                 175
Asn Asp Val Asp Arg Thr Ala Gly Arg Gly Gly Val Gly Ala Val Met
                180                 185                 190
Gly Ser Lys Asn Leu Lys Ala Ile Val Val Lys Gly Ser Gly Lys Val
            195                 200                 205
Lys Leu Phe Asp Glu Gln Lys Val Lys Glu Val Ala Leu Glu Lys Thr
            210                 215                 220
Asn Ile Leu Arg Lys Asp Pro Val Ala Gly Gly Leu Pro Thr Tyr
225                 230                 235                 240
Gly Thr Ala Val Leu Val Asn Ile Ile Asn Glu Asn Gly Val His Pro
                245                 250                 255
Val Lys Asn Phe Gln Lys Ser Tyr Thr Asp Gln Ala Asp Lys Ile Ser
                260                 265                 270
Gly Glu Thr Leu Thr Lys Asp Cys Leu Val Arg Lys Asn Pro Cys Tyr
            275                 280                 285
Arg Cys Pro Ile Ala Cys Gly Arg Trp Val Lys Leu Asp Asp Gly Thr
290                 295                 300
Glu Cys Gly Gly Pro Glu Tyr Glu Thr Leu Trp Ser Phe Gly Ser Asp
305                 310                 315                 320
Cys Asp Val Tyr Asp Ile Asn Ala Val Asn Thr Ala Asn Met Leu Cys
                325                 330                 335
Asn Glu Tyr Gly Leu Asp Thr Ile Thr Ala Gly Cys Thr Ile Ala Ala
            340                 345                 350
Ala Met Glu Leu Tyr Gln Arg Gly Tyr Ile Lys Asp Glu Glu Ile Ala
            355                 360                 365
Ala Asp Gly Leu Ser Leu Asn Trp Gly Asp Ala Lys Ser Met Val Glu
370                 375                 380
Trp Val Lys Lys Met Gly Leu Arg Glu Gly Phe Gly Asp Lys Met Ala
385                 390                 395                 400
Asp Gly Ser Tyr Arg Leu Cys Asp Ser Tyr Gly Val Pro Glu Tyr Ser
                405                 410                 415
Met Thr Val Lys Lys Gln Glu Leu Pro Ala Tyr Asp Pro Arg Gly Ile
            420                 425                 430
Gln Gly His Gly Ile Thr Tyr Ala Val Asn Asn Arg Gly Gly Cys His
```

```
            435                 440                 445
Ile Lys Gly Tyr Met Val Ser Pro Glu Ile Leu Gly Tyr Pro Glu Lys
            450                 455                 460

Leu Asp Arg Leu Ala Val Glu Gly Lys Ala Gly Tyr Ala Arg Val Phe
465                 470                 475                 480

His Asp Leu Thr Ala Val Ile Asp Ser Leu Gly Leu Cys Ile Phe Thr
                485                 490                 495

Thr Phe Gly Leu Gly Ala Gln Asp Tyr Val Asp Met Tyr Asn Ala Val
                500                 505                 510

Val Gly Gly Glu Leu His Asp Val Asn Ser Leu Met Leu Ala Gly Asp
                515                 520                 525

Arg Ile Trp Thr Leu Glu Lys Ile Phe Asn Leu Lys Ala Gly Ile Asp
                530                 535                 540

Ser Ser Gln Asp Thr Leu Pro Lys Arg Leu Leu Glu Glu Gln Ile Pro
545                 550                 555                 560

Glu Gly Pro Ser Lys Gly Glu Val His Lys Leu Asp Val Leu Leu Pro
                565                 570                 575

Glu Tyr Tyr Ser Val Arg Gly Trp Asp Lys Asn Gly Ile Pro Thr Glu
                580                 585                 590

Glu Thr Leu Lys Lys Leu Gly Leu Asp Glu Tyr Val Gly Lys Leu
                595                 600                 605

<210> SEQ ID NO 16
<211> LENGTH: 607
<212> TYPE: PRT
<213> ORGANISM: Clostridium ragsdalei

<400> SEQUENCE: 16

Met Tyr Gly Tyr Ser Gly Lys Val Leu Arg Ile Asn Leu Ser Asn Lys
1               5                   10                  15

Thr Tyr Lys Ala Glu Glu Leu Lys Ile Asp Glu Ala Lys Lys Phe Ile
                20                  25                  30

Gly Ala Arg Gly Leu Gly Val Lys Thr Leu Leu Asp Glu Ile Asp Pro
            35                  40                  45

Lys Ile Asp Pro Leu Ser Pro Asp Asn Lys Phe Ile Ile Ala Thr Gly
        50                  55                  60

Pro Leu Thr Gly Ala Pro Val Pro Thr Ser Gly Arg Phe Met Val Ile
65                  70                  75                  80

Thr Lys Ala Pro Leu Thr Gly Thr Ile Gly Ile Ala Asn Ser Gly Gly
                85                  90                  95

Lys Trp Gly Ala Glu Leu Lys Thr Ala Gly Tyr Asp Met Val Ile Val
                100                 105                 110

Glu Gly Lys Ser Asp Lys Pro Val Tyr Val Asn Ile Val Asp Asp Lys
            115                 120                 125

Val Glu Phe Lys Asp Ala Ser His Val Trp Gly Lys Leu Thr Glu Glu
130                 135                 140

Thr Thr Lys Met Leu Gln Asn Glu Ile Asp Ala Lys Ala Lys Val Leu
145                 150                 155                 160

Cys Ile Gly Pro Ala Gly Glu Asn Leu Ser Leu Met Ala Ala Val Met
                165                 170                 175

Asn Asp Ile Asp Arg Thr Ala Gly Arg Gly Val Gly Ala Val Met
                180                 185                 190

Gly Ser Lys Asn Leu Lys Ala Ile Val Val Lys Gly Ser Gly Lys Val
            195                 200                 205
```

Lys Leu Phe Asp Glu Glu Lys Val Lys Ala Val Ser Leu Gln Lys Ser
210                 215                 220

Asp Ile Leu Arg Lys Asp Pro Val Ala Gly Gly Leu Pro Thr Tyr
225                 230                 235                 240

Gly Thr Ala Val Leu Val Asn Ile Ile Asn Glu Asn Gly Ile Asn Pro
            245                 250                 255

Val Arg Asn Phe Gln Glu Ser Tyr Thr Asp Glu Ala Asp Lys Val Ser
                260                 265                 270

Gly Glu Thr Met Thr Gln Glu Cys Leu Val Arg Lys Asn Pro Cys Tyr
            275                 280                 285

Arg Cys Pro Ile Ala Cys Gly Arg Trp Val Arg Leu Asp Asp Gly Thr
290                 295                 300

Glu Cys Gly Gly Pro Glu Tyr Glu Thr Leu Trp Ser Phe Gly Ser Asp
305                 310                 315                 320

Cys Asp Val Tyr Asp Leu Asn Ala Val Asn Lys Ala Asn Met Leu Cys
                325                 330                 335

Asn Glu Tyr Gly Leu Asp Thr Ile Ser Ala Gly Ala Thr Ile Ala Ser
            340                 345                 350

Ala Met Glu Leu Tyr Gln Arg Gly Tyr Ile Lys Asp Glu Ile Ala
        355                 360                 365

Ala Asp Gly Leu Ser Leu Lys Trp Gly Asp Ala Lys Ser Met Val Glu
370                 375                 380

Trp Val Lys Lys Met Gly Arg Arg Glu Gly Phe Gly Lys Met Ala
385                 390                 395                 400

Asp Gly Ser Tyr Arg Leu Cys Glu Ser Tyr Gly Val Pro Gln Tyr Ser
                405                 410                 415

Met Ser Val Lys Lys Gln Glu Leu Pro Ala Tyr Asp Pro Arg Gly Ala
            420                 425                 430

Gln Gly His Gly Leu Thr Tyr Ala Val Asn Asn Arg Gly Gly Cys His
        435                 440                 445

Ile Lys Gly Tyr Met Ile Ser Pro Glu Ile Leu Gly Tyr Pro Glu Lys
450                 455                 460

Leu Asp Arg Phe Ser Ile Glu Gly Lys Pro Ala Tyr Ala Lys Val Phe
465                 470                 475                 480

His Asp Leu Thr Ala Val Ile Asp Ser Leu Gly Leu Cys Ile Phe Thr
                485                 490                 495

Thr Phe Gly Leu Gly Ala Gln Asp Tyr Val Asp Met Tyr Asn Ala Val
            500                 505                 510

Val Gly Gly Glu Leu His Asp Val Asp Ser Leu Met Leu Ala Gly Asp
        515                 520                 525

Arg Val Trp Thr Leu Glu Lys Ile Phe Asn Leu Lys Ala Gly Val Gly
530                 535                 540

Ser Ser Gln Asp Thr Leu Pro Lys Arg Leu Leu Glu Glu Val Val
545                 550                 555                 560

Glu Gly Pro Ser Lys Gly His Val His Arg Leu Asp Glu Leu Val Pro
                565                 570                 575

Glu Tyr Tyr Ser Val Arg Gly Trp Asp Lys Asn Gly Val Pro Thr Glu
            580                 585                 590

Glu Thr Leu Lys Lys Leu Gly Leu Glu Glu Tyr Ile Gly Lys Ile
        595                 600                 605

<210> SEQ ID NO 17
<211> LENGTH: 607
<212> TYPE: PRT

<213> ORGANISM: Clostridium ljungdahlii

<400> SEQUENCE: 17

```
Met Tyr Gly Tyr Asp Gly Lys Val Leu Arg Ile Asn Leu Lys Glu Arg
 1               5                  10                  15

Thr Cys Lys Ser Glu Asn Leu Asp Leu Asp Lys Ala Lys Lys Phe Ile
            20                  25                  30

Gly Cys Arg Gly Leu Gly Val Lys Thr Leu Phe Asp Glu Ile Asp Pro
        35                  40                  45

Lys Ile Asp Ala Leu Ser Pro Glu Asn Lys Phe Ile Ile Val Thr Gly
    50                  55                  60

Pro Leu Thr Gly Ala Pro Val Pro Thr Ser Gly Arg Phe Met Val Val
65                  70                  75                  80

Thr Lys Ala Pro Leu Thr Gly Thr Ile Gly Ile Ser Asn Ser Gly Gly
                85                  90                  95

Lys Trp Gly Val Asp Leu Lys Lys Ala Gly Trp Asp Met Ile Ile Val
            100                 105                 110

Glu Asp Lys Ala Asp Ser Pro Val Tyr Ile Glu Ile Asp Asp Lys
        115                 120                 125

Val Glu Ile Lys Asp Ala Ser Gln Leu Trp Gly Lys Val Thr Ser Glu
    130                 135                 140

Thr Thr Lys Glu Leu Glu Lys Ile Thr Glu Asn Lys Ser Lys Val Leu
145                 150                 155                 160

Cys Ile Gly Pro Ala Gly Glu Arg Leu Ser Leu Met Ala Ala Val Met
                165                 170                 175

Asn Asp Val Asp Arg Thr Ala Ala Arg Gly Gly Val Gly Ala Val Met
            180                 185                 190

Gly Ser Lys Asn Leu Lys Ala Ile Thr Val Lys Gly Thr Gly Lys Ile
        195                 200                 205

Ala Leu Ala Asp Lys Glu Lys Val Lys Val Ser Val Glu Lys Ile
    210                 215                 220

Thr Thr Leu Lys Asn Asp Pro Val Ala Gly Gln Gly Met Pro Thr Tyr
225                 230                 235                 240

Gly Thr Ala Ile Leu Val Asn Ile Ile Asn Glu Asn Gly Val His Pro
                245                 250                 255

Val Lys Asn Phe Gln Glu Ser Tyr Thr Asn Gln Ala Asp Lys Ile Ser
            260                 265                 270

Gly Glu Thr Leu Thr Ala Asn Gln Leu Val Arg Lys Asn Pro Cys Tyr
        275                 280                 285

Ser Cys Pro Ile Gly Cys Gly Arg Trp Val Arg Leu Lys Asp Gly Thr
    290                 295                 300

Glu Cys Gly Gly Pro Glu Tyr Glu Thr Leu Trp Cys Phe Gly Ser Asp
305                 310                 315                 320

Cys Gly Ser Tyr Asp Leu Asp Ala Ile Asn Glu Ala Asn Met Leu Cys
                325                 330                 335

Asn Glu Tyr Gly Ile Asp Thr Ile Thr Cys Gly Ala Thr Ile Ala Ala
            340                 345                 350

Ala Met Glu Leu Tyr Gln Arg Gly Tyr Ile Lys Asp Glu Glu Ile Ala
        355                 360                 365

Gly Asp Asn Leu Ser Leu Lys Trp Gly Asp Thr Glu Ser Met Ile Gly
    370                 375                 380

Trp Ile Lys Arg Met Val Tyr Ser Glu Gly Phe Gly Ala Lys Met Thr
385                 390                 395                 400
```

```
Asn Gly Ser Tyr Arg Leu Cys Glu Gly Tyr Gly Ala Pro Glu Tyr Ser
            405                 410                 415

Met Thr Val Lys Lys Gln Glu Ile Pro Ala Tyr Asp Pro Arg Gly Ile
        420                 425                 430

Gln Gly His Gly Ile Thr Tyr Ala Val Asn Asn Arg Gly Gly Cys His
        435                 440                 445

Ile Lys Gly Tyr Met Ile Asn Pro Glu Ile Leu Gly Tyr Pro Glu Lys
        450                 455                 460

Leu Asp Arg Phe Ala Leu Asp Gly Lys Ala Ala Tyr Ala Lys Leu Phe
465                 470                 475                 480

His Asp Leu Thr Ala Val Ile Asp Ser Leu Gly Leu Cys Ile Phe Thr
                485                 490                 495

Thr Phe Gly Leu Gly Ile Gln Asp Tyr Val Asp Met Tyr Asn Ala Val
            500                 505                 510

Val Gly Glu Ser Thr Tyr Asp Ala Asp Ser Leu Leu Glu Ala Gly Asp
        515                 520                 525

Arg Ile Trp Thr Leu Glu Lys Leu Phe Asn Leu Ala Ala Gly Ile Asp
530                 535                 540

Ser Ser Gln Asp Thr Leu Pro Lys Arg Leu Leu Glu Glu Pro Ile Pro
545                 550                 555                 560

Asp Gly Pro Ser Lys Gly Glu Val His Arg Leu Asp Val Leu Leu Pro
                565                 570                 575

Glu Tyr Tyr Ser Val Arg Gly Trp Ser Lys Gly Ile Pro Thr Glu
            580                 585                 590

Glu Thr Leu Lys Lys Leu Gly Leu Asp Glu Tyr Ile Gly Lys Phe
        595                 600                 605

<210> SEQ ID NO 18
<211> LENGTH: 607
<212> TYPE: PRT
<213> ORGANISM: Clostridium ragsdalei

<400> SEQUENCE: 18

Met Tyr Gly Tyr Asn Gly Lys Val Leu Arg Ile Asn Leu Lys Glu Arg
1               5                   10                  15

Thr Cys Lys Ser Glu Asn Leu Asp Leu Asp Lys Ala Lys Lys Phe Ile
            20                  25                  30

Gly Cys Arg Gly Leu Gly Val Lys Thr Leu Phe Asp Glu Ile Asp Pro
        35                  40                  45

Lys Ile Asp Ala Leu Ser Pro Glu Asn Lys Phe Ile Ile Val Thr Gly
    50                  55                  60

Pro Leu Thr Gly Ala Pro Val Pro Thr Ser Gly Arg Phe Met Val Val
65                  70                  75                  80

Thr Lys Ala Pro Leu Thr Gly Thr Ile Gly Ile Ser Asn Ser Gly Gly
                85                  90                  95

Lys Trp Gly Val Asp Leu Lys Lys Ala Gly Trp Asp Met Ile Ile Val
            100                 105                 110

Glu Asp Lys Ala Asp Ser Pro Val Tyr Ile Glu Ile Val Asp Asp Lys
        115                 120                 125

Val Glu Ile Lys Asp Ala Ser Gln Leu Trp Gly Lys Val Thr Ser Glu
    130                 135                 140

Thr Thr Lys Glu Leu Glu Lys Ile Thr Glu Asn Arg Ser Lys Val Leu
145                 150                 155                 160

Cys Ile Gly Pro Ala Gly Glu Arg Leu Ser Leu Met Ala Ala Val Met
                165                 170                 175
```

-continued

```
Asn Asp Val Asp Arg Thr Ala Ala Arg Gly Val Gly Ala Val Met
            180                 185                 190

Gly Ser Lys Asn Leu Lys Ala Ile Thr Val Lys Gly Thr Gly Lys Ile
        195                 200                 205

Ala Leu Ala Asp Lys Glu Lys Val Lys Val Ser Val Glu Lys Ile
    210                 215                 220

Thr Thr Leu Lys Asn Asp Pro Val Ala Gly Gln Gly Met Pro Thr Tyr
225                 230                 235                 240

Gly Thr Ala Ile Leu Val Asn Ile Ile Asn Glu Asn Gly Val His Pro
                245                 250                 255

Val Asn Asn Phe Gln Glu Ser Tyr Thr Asp Gln Ala Asp Lys Ile Ser
        260                 265                 270

Gly Glu Thr Leu Thr Ala Asn Gln Leu Val Arg Lys Asn Pro Cys Tyr
        275                 280                 285

Ser Cys Pro Ile Gly Cys Gly Arg Trp Val Arg Leu Lys Asp Gly Thr
        290                 295                 300

Glu Cys Gly Gly Pro Glu Tyr Glu Thr Leu Trp Cys Phe Gly Ser Asp
305                 310                 315                 320

Cys Gly Ser Tyr Asp Leu Asp Ala Ile Asn Glu Ala Asn Met Leu Cys
                325                 330                 335

Asn Glu Tyr Gly Ile Asp Thr Ile Thr Cys Gly Ala Thr Ile Ala Ala
                340                 345                 350

Ala Met Glu Leu Tyr Gln Arg Gly Tyr Val Lys Asp Glu Glu Ile Ala
        355                 360                 365

Gly Asp Asn Leu Ser Leu Lys Trp Gly Asp Thr Glu Ser Met Ile Gly
        370                 375                 380

Trp Ile Lys Lys Met Val Tyr Ser Glu Gly Phe Gly Ala Lys Met Thr
385                 390                 395                 400

Asn Gly Ser Tyr Arg Leu Cys Glu Gly Tyr Gly Val Pro Glu Tyr Ser
                405                 410                 415

Met Thr Val Lys Lys Gln Glu Ile Pro Ala Tyr Asp Pro Arg Gly Ile
                420                 425                 430

Gln Gly His Gly Ile Thr Tyr Ala Val Asn Asn Arg Gly Gly Cys His
        435                 440                 445

Ile Lys Gly Tyr Met Ile Asn Pro Glu Ile Leu Gly Tyr Pro Glu Lys
    450                 455                 460

Leu Asp Arg Phe Ala Leu Asp Gly Lys Ala Ala Tyr Ala Lys Met Met
465                 470                 475                 480

His Asp Leu Thr Ala Val Ile Asp Ser Leu Gly Leu Cys Ile Phe Thr
                485                 490                 495

Thr Phe Gly Leu Gly Ile Gln Asp Tyr Val Asp Met Tyr Asn Ala Val
                500                 505                 510

Val Gly Glu Ser Thr Cys Asp Ser Asp Ser Leu Leu Glu Ala Gly Asp
        515                 520                 525

Arg Val Trp Thr Leu Glu Lys Leu Phe Asn Leu Ala Ala Gly Ile Asp
    530                 535                 540

Ser Ser Gln Asp Thr Leu Pro Lys Arg Leu Leu Glu Glu Pro Ile Pro
545                 550                 555                 560

Asp Gly Pro Ser Lys Gly His Val His Arg Leu Asp Val Leu Leu Pro
                565                 570                 575

Glu Tyr Tyr Ser Val Arg Gly Trp Ser Lys Glu Gly Ile Pro Thr Glu
                580                 585                 590
```

```
Glu Thr Leu Lys Lys Leu Gly Leu Asp Glu Tyr Ile Gly Lys Phe
    595                 600                 605
```

<210> SEQ ID NO 19
<211> LENGTH: 22
<212> TYPE: DNA
<213> ORGANISM: Artificial Sequence
<220> FEATURE:
<223> OTHER INFORMATION: AOR1-A-forward primer

<400> SEQUENCE: 19
acttggatta tgtattttta ca                                           22

<210> SEQ ID NO 20
<211> LENGTH: 22
<212> TYPE: DNA
<213> ORGANISM: Artificial Sequence
<220> FEATURE:
<223> OTHER INFORMATION: AOR1-A-reverse primer

<400> SEQUENCE: 20
tgaactatct atgcctgctt tt                                           22

<210> SEQ ID NO 21
<211> LENGTH: 20
<212> TYPE: DNA
<213> ORGANISM: Artificial Sequence
<220> FEATURE:
<223> OTHER INFORMATION: AOR2-A-forward primer

<400> SEQUENCE: 21
aagaaagaac ttgcaaatca                                              20

<210> SEQ ID NO 22
<211> LENGTH: 19
<212> TYPE: DNA
<213> ORGANISM: Artificial Sequence
<220> FEATURE:
<223> OTHER INFORMATION: AOR2-A reverse primer

<400> SEQUENCE: 22
cggagctcca gttaaagga                                               19

<210> SEQ ID NO 23
<211> LENGTH: 24
<212> TYPE: DNA
<213> ORGANISM: Artificial Sequence
<220> FEATURE:
<223> OTHER INFORMATION: BCoAAT forward primer

<400> SEQUENCE: 23
agccatgcta gctcctctca tgta                                         24

<210> SEQ ID NO 24
<211> LENGTH: 24
<212> TYPE: DNA
<213> ORGANISM: Artificial Sequence
<220> FEATURE:
<223> OTHER INFORMATION: BCoAAT reverse primer

<400> SEQUENCE: 24
ggagtatcaa ccgattattc acag                                         24

<210> SEQ ID NO 25
<211> LENGTH: 24
<212> TYPE: DNA

```
<213> ORGANISM: Artificial Sequence
<220> FEATURE:
<223> OTHER INFORMATION: Buk forward primer

<400> SEQUENCE: 25
gatatcattt ctgaatgtat accc                                            24

<210> SEQ ID NO 26
<211> LENGTH: 24
<212> TYPE: DNA
<213> ORGANISM: Artificial Sequence
<220> FEATURE:
<223> OTHER INFORMATION: Buk reverse primer

<400> SEQUENCE: 26
gatatcattt ctgaatgtat accc                                            24

<210> SEQ ID NO 27
<211> LENGTH: 22
<212> TYPE: DNA
<213> ORGANISM: Artificial Sequence
<220> FEATURE:
<223> OTHER INFORMATION: Iron-only hydrogenase-forward primer

<400> SEQUENCE: 27
tgtgaacgtc ctgaaatgaa ag                                              22

<210> SEQ ID NO 28
<211> LENGTH: 22
<212> TYPE: DNA
<213> ORGANISM: Artificial Sequence
<220> FEATURE:
<223> OTHER INFORMATION: Iron-only hydrogenase reverse primer

<400> SEQUENCE: 28
agtgcctgca ccagaataag tt                                              22

<210> SEQ ID NO 29
<211> LENGTH: 20
<212> TYPE: DNA
<213> ORGANISM: Artificial Sequence
<220> FEATURE:
<223> OTHER INFORMATION: Hyg-1 forward primer

<400> SEQUENCE: 29
gcccgatata aatcctcttt                                                 20

<210> SEQ ID NO 30
<211> LENGTH: 20
<212> TYPE: DNA
<213> ORGANISM: Artificial Sequence
<220> FEATURE:
<223> OTHER INFORMATION: Hyg-1 reverse primer

<400> SEQUENCE: 30
ccaacaaaaa ttccatgatt                                                 20

<210> SEQ ID NO 31
<211> LENGTH: 20
<212> TYPE: DNA
<213> ORGANISM: Artificial Sequence
<220> FEATURE:
<223> OTHER INFORMATION: Hyg-2 forward primer

<400> SEQUENCE: 31
ctacaatttt aaacgctgca                                                 20
```

```
<210> SEQ ID NO 32
<211> LENGTH: 21
<212> TYPE: DNA
<213> ORGANISM: Artificial Sequence
<220> FEATURE:
<223> OTHER INFORMATION: Hyg-2 reverse primer

<400> SEQUENCE: 32
gctctggcac tgtttgttct a                                              21

<210> SEQ ID NO 33
<211> LENGTH: 20
<212> TYPE: DNA
<213> ORGANISM: Artificial Sequence
<220> FEATURE:
<223> OTHER INFORMATION: Hyg-3 forward primer

<400> SEQUENCE: 33
tgatacaaac tttggtgcag                                                20

<210> SEQ ID NO 34
<211> LENGTH: 20
<212> TYPE: DNA
<213> ORGANISM: Artificial Sequence
<220> FEATURE:
<223> OTHER INFORMATION: Hyg-3 reverse primer

<400> SEQUENCE: 34
atatagctcc agccatctga                                                20
```

US 9,790,522 B2

COMPOSITIONS AND METHODS FOR THE CONVERSION OF SHORT-CHAINED CARBOXYLIC ACIDS TO ALCOHOLS USING CLOSTRIDIAL ENZYMES

FIELD OF THE INVENTION

The invention relates to the fields of bacterial metabolism and the utilization or consumption of short-chain carboxylic acids to reduced products. Specifically, it relates to syngas fermentations using monocultures of syngas-utilizing homoacetogenic bacteria for the production of alcohols using native alcohol dehydrogenase. This invention also relates to co-cultures of microorganisms or consortia of microorganisms that comprise a syngas-utilizing homoacetogen and a butyrogenic organism that when grown together produce short-chain carboxylic acids from $C_2$-$C_6$ in length and syntrophically convert them efficiently to the commercially useful $C_2$-$C_6$ alcohols.

BACKGROUND OF THE INVENTION

Butanol is an important industrial chemical with a wide range of applications. It can be used as a motor fuel particularly in combination with gasoline to which it can be added in all proportions. Isobutanol can also be used as a precursor to Methyl Tertiary Butyl Ether (MTBE). Currently the world production of n-Butanol is 3.5 million tons/yr. (7.7 billion lb/yr). Furthermore, conversion of alcohols to long-chain linear hydrocarbons that would be suitable for jet fuel use are being developed and demonstrated, which could further increase the demand for n-butanol (The Naval Air Warfare Center-Weapons Division, (2012) Cobalt and Abermarle). Fermentation of carbohydrates to acetone, butanol and ethanol (ABE) is well known and was commercially practiced worldwide from around 1915 to 1955 (Beesch, S. C. (1953). A Microbiological Process Report—Applied Microbiology, 1, 85-95). With the advent of petrochemical processes and low-cost petrochemical feedstocks the carbohydrate-based processes became unattractive and were discontinued.

Attempts have been made to improve the alcohol yield of bacteria that ferment a variety of sugars to acetate and butyrate. The art has sought to employ recombinant techniques to transform bacterium such as *C. acetobutylicum* (Green et al., 1996 Genetic manipulation of acid formation pathways *Microbiology*, 142, 2079-2086) and *C. tyrobutyricum* (X. Liu et al., 2006 Construction and Characterization of an ack Deleted Mutant of *Clostridium tyrobutyricum*, *Biotechnology Progress*, 22, 1265-1275). However, such techniques have only resulted in transformation occurring at low frequencies.

Anaerobic acetogenic microorganisms offer a viable route to convert waste gases, such as syngas, to useful products, such as ethanol, via a fermentation process. Such bacteria catalyze the conversion of $H_2$ and $CO_2$ and/or CO to acids and/or alcohols with higher specificity, higher yields and lower energy costs than can be attained by traditional production processes. While many of the anaerobic microorganisms utilized in the fermentation of ethanol also produce butanol as a secondary product, to date, no single anaerobic microorganism has been described that can utilize the syngas fermentation process to produce high yields of butanol.

Thus, there remains a need in the art to produce a biocatalyst bacterium or co-culture of bacteria that produces useful commercial products such as $C_2$-$C_6$ alcohols (including ethanol, propanol, butanol, pentanol and hexanol and any of their isomers).

SUMMARY OF THE INVENTION

Provided herein are methods for the production of an alcohol, comprising: culturing a recombinant C1-fixing homoacetogen microorganism in a culture medium in the presence of syngas, wherein the C1-fixing homoacetogen microorganism comprises a recombinant gene encoding an aldehyde ferredoxin oxidoreductase polypeptide modulated by a promoter, wherein the recombinant C1-fixing microorganism produces an alcohol.

In particular embodiments the aldehyde ferredoxin oxidoreductase gene encodes a *Clostridium* aldehyde ferredoxin oxidoreductase polypeptide. In particular embodiments the aldehyde oxidoreductase gene is at least 95% identical to SEQ ID NO: 1 or SEQ ID NO: 3.

In particular embodiments the promoter is an inducible promoter or a constitutive promoter.

In particular embodiments the methods provided herein produce ethanol. In other particular embodiments, the C1-fixing homoacetogen microorganism is *C. ljungdahlii*, *C. ragsdalei*, *C. autoethanogenum* or *C. coskatii*.

In other aspects, provided herein are methods for the production of butanol, comprising: culturing a co-culture comprising a recombinant C1-fixing homoacetogen microorganism and a C4-producing butyrate microorganism in a culture medium in the presence of syngas, wherein the C1-fixing homoacetogen microorganism comprises a recombinant gene encoding a aldehyde ferredoxin oxidoreductase polypeptide modulated by a promoter.

In particular embodiments the C4-producing butyrate microorganism comprises a gene encoding a Butyryl-CoA acetate transferase polypeptide or a Butyrate kinase polypeptide. In other particular embodiments, the aldehyde ferredoxin oxidoreductase gene encodes a *Clostridium* aldehyde ferredoxin oxidoreductase polypeptide. In yet other embodiments, the aldehyde ferredoxin oxidoreductase gene is at least 95% identical to SEQ ID NO: 1 or SEQ ID NO: 3.

In particular embodiments the promoter is an inducible promoter or a constitutive promoter. In other particular embodiments the C1-fixing homoacetogen microorganism is *C. ljungdahlii*, *C. ragsdalei*, *C. autoethanogenum* or *C. coskatii*. In other particular embodiments the C4-producing butyrate microorganism is *Clostridium kluyveri*, *Clostridium carboxidivorans*, *Butyribacterium methylotrophicum*, or *Clostridium pharus*.

In other aspects provided herein are microorganism co-cultures for the conversion of syngas to butanol comprising: a recombinant C1-fixing homoacetogen microorganism comprising a recombinant gene encoding a aldehyde ferredoxin oxidoreductase polypeptide modulated by a promoter and a C4-producing butyrate microorganism.

In particular embodiments the C4-producing butyrate microorganism comprises a gene encoding a Butyryl-CoA acetate transferase polypeptide or a Butyrate kinase polypeptide. In other particular embodiments, the aldehyde ferredoxin oxidoreductase gene encodes a *Clostridium* aldehyde ferredoxin oxidoreductase polypeptide. In yet other embodiments, the aldehyde ferredoxin oxidoreductase gene is at least 95% identical to SEQ ID NO: 1 or SEQ ID NO: 3.

In particular embodiments, the promoter is an inducible promoter or a constitutive promoter. In yet other embodiments, the C1-fixing homoacetogen microorganism is *C. ljungdahlii*, *C. ragsdalei*, *C. autoethanogenum* or *C.*

*coskatii*. In yet other embodiments, the C4-producing butyrate microorganism is *Clostridium kluyveri, Clostridium carboxidivorans, Butyribacterium methylotrophicum,* or *Clostridium pharus*.

BRIEF DESCRIPTION OF THE DRAWINGS

FIGS. 2A and 2B. Physical maps of AOR expression vectors containing one of the cloned aldehyde ferredoxin oxidoreductase genes identified in *C. autoethanogenum*. 2(A) Expression vector pCKAR192, containing one of the Clostridial aldehyde ferredoxin oxidoreductase genes expressed from a constitutive Clostridial promoter Pcoos. This promoter has been shown to be highly expressed in *E. coli* DH10B cells. 2(B) *E. coli-Clostridium* shuttle vector pCKAR192T2, the same as pCKAR192 but containing a clostridial replicon and a chloramphenicol resistance gene known to express in homacetogenic Clostridia.

FIGS. 3A and 3B. Physical maps of AOR expression vectors containing cloned aldehyde ferredoxin oxidoreductase genes. 3(A) Expression vector pCKAR214, containing one of the Clostridial aldehyde ferredoxin oxidoreductase genes expressed from a constitutive Clostridial promoter Ppta-ack. This promoter has been shown to be highly expressed in *E. coli* DH10B cells. 3(B) *E. coli-Clostridium* shuttle vector pCKAR214T2, the same as pCKAR214 but containing a clostridial replicon and a chloramphenicol resistance gene known to express in homoacetogenic Clostridia.

FIGS. 4A and 4B. DNA and amino acid sequence alignments of the two native AORs identified in *C. autoethanogenum*. 4(A) alignment of the two AOR gene sequences AOR1 and AOR2 and 4(B) amino acid alignment of AOR1 and AOR2.

FIGS. 5A and 5B. Amino acid alignment of the two native AORs identified in *C. autoethanogenum* aligned with the best homology matches of the AOR amino acid sequences identified in *C. ljungdahlii* PETC (AOR1: SEQ ID NO: 15; AOR2: SEQ ID NO:17) and *C. ragsdalei* ATCC BAA-624 (AOR1: SEQ ID NO: 16; AOR2: SEQ ID NO:18). 5(A) alignment of AOR1 amino acid sequences and 5(B) alignment of AOR2 amino acid sequences.

FIGS. 8A-8D. Agarose gel showing PCR products produced with AOR-specific primers. FIGS. 8A and 8B show electrophoresis gels of amplicons using primers AOR1A (FIG. 8A) and BCoAAT (FIG. 8B) designed to target *C. autoethanogenum* AOR1 and butyrogen butyryl-CoA acetate transferase, respectively; FIGS. 8C and 8D show electrophoresis gels of amplicons using primers AOR2A (FIG. 8C) and Buk (FIG. 8D) designed to target *C. autoethanogenum* AOR2 and butyrogen butyrate kinase.

FIGS. 12A and 12B. Diagrams of *E. coli-Clostridium* shuttle vectors pCK32 (FIG. 12A) and pCK32AOR1 (FIG. 12B). *E. coli-Clostridium* shuttle vectors used for transforming *Clostridium* biocatalyst strains. pCK32AOR1 differs from pCK232 only in that it contains the AOR1 gene expressed from the *Clostridium* promoter Ppta.

FIGS. 14A and 14B. Graph illustrating the specific productivity (grams/OD) of ethanol and acetate for the wild-type and TF18 strains at 1, 2, and 5 days post-inoculation.

DETAILED DESCRIPTION OF THE INVENTION

Figure 1:
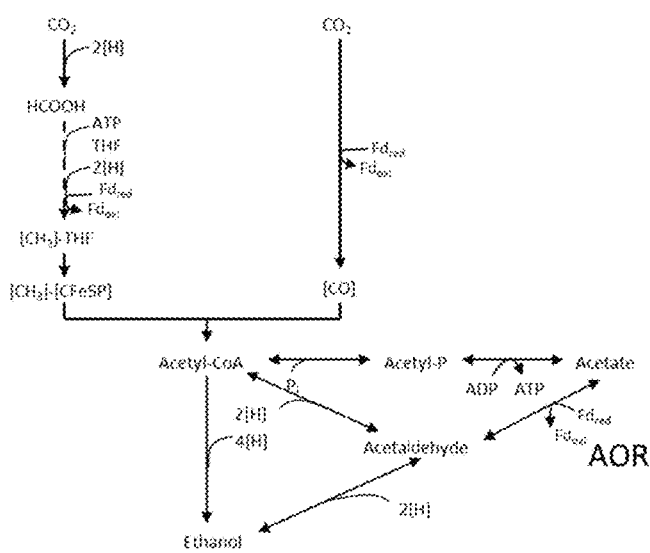
FIG. 1. Schematic illustration of the Wood-Ljungdahl ($C_1$) and $C_2$ biosynthesis pathways from syngas showing among others the enzymatic reactions catalyzed by native homoacetogen aldehyde ferredoxin oxidoreductase (AOR).

All publications, patents and patent applications cited herein are hereby expressly incorporated by reference for all purposes.

Methods well known to those skilled in the art can be used to construct genetic expression constructs and recombinant microorganisms according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and *PCR Protocols: A Guide to Methods and Applications* (Innis et al., 1990, Academic Press, San Diego, Calif.).

As used herein, the terms "polynucleotide", "nucleotide", "oligonucleotide", and "nucleic acid" can be used interchangeably to refer to nucleic acid comprising DNA, RNA, derivatives thereof, or combinations thereof Provided herein are methods for increased production of an alcohol, comprising: culturing a recombinant C1-fixing homoacetogen microorganism in a culture medium in the presence of syngas, wherein the C1-fixing homoacetogen microorganism comprises a recombinant gene encoding a aldehyde ferredoxin oxidoreductase (AOR) polypeptide modulated by a promoter, wherein the recombinant C1-fixing microorganism produces an increased amount of alcohol compared to a wild-type C1-fixing homoacetogen microorganism.

AOR proteins are involved in the conversion of short-chain carboxylic acids such as acetate and butyrate to their corresponding aldehydes via a native activity in syngas-utilizing homoacetogens. The reduction of carboxylic acids to aldehydes by the AOR proteins is thermodynamically uphill, but the net reaction sequence to alcohols is favorable and easily generates enough free energy to drive it. Additionally, the reaction is driven by a low-redox ferredoxin which interacts with tungsten in the catalysis (White et al. (1989), *Eur. J. Biochem*, 184: 89-96). This reaction has been documented to occur in several purified enzyme preparations from Clostridia and importantly unlike aerobic carboxylic acid reductase converts the acids to alcohols via a non-activated intermediate (White et al. (1991), *Biol. Chem. Hoppe-Seyler* 372:999-1005). In a C2 fermentation, conversion of acetate to aldehyde is important for keeping the free acid concentration from accumulating to detrimental or toxic levels. The reverse reaction (back to Acetyl-CoA) would require using an ATP to rephosphorylate acetate, which would not be energetically favorable, thus making the AOR activity very important in controlling acid levels and cell stress. Recombinant *Clostridium* microorganisms containing constitutively expressed AOR activity allows for expression to continue unabated even when the down regulation signals would decrease native AOR expression.

The C1-fixing microorganisms suitable for use in the methods disclosed herein are also known as homoacetogens. Homoacetogens have the ability, under anaerobic conditions, to produce acetic acid and ethanol from the substrates, $CO+H_2O$, or $H_2+CO_2$ or $CO+H_2+CO_2$. The CO and $CO_2$ provide the carbon source and the $H_2$ and CO provide the electron source for the reactions producing acetic acid and ethanol.

C1-fixing microorganisms suitable for use in the inventive methods include, without limitation, homoacetogens such as *Clostridium ljungdahlii*, *Clostridium autoethanogenum*, *Clostridium ragsdalei*, and *Clostridium coskatii*. Additional C1 fixing microorganisms that are suitable for use in the disclosed methods include *Alkalibaculum bacchi*, *Clostridium thermoaceticum*, and *Clostridium aceticum*.

As used herein, synthesis gas (syngas) is a gas containing carbon monoxide, carbon dioxide and frequently hydrogen. "Syngas" includes streams that contain carbon dioxide in combination with hydrogen and that may include little or no carbon monoxide. "Syngas" may also include carbon monoxide gas streams that may have little or no hydrogen.

In particular embodiments, plasmid vectors comprising highly active Clostridial promoters operably linked to a nucleotide sequence encoding an AOR1 and AOR2 polynucleotide are employed in the methods disclosed herein.

In particular embodiments the recombinant aldehyde ferredoxin oxidoreductase gene encodes a *Clostridium* aldehyde ferredoxin oxidoreductase polypeptide.

Functional homologs of the polypeptides described above are also suitable for use in the disclosed methods. A functional homolog is a polypeptide that has sequence similarity to a reference polypeptide, and that carries out one or more of the biochemical or physiological function(s) of the reference polypeptide. A functional homolog and the reference polypeptide can be natural occurring polypeptides, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional AOR polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of polypeptides described herein. Sequence analysis can involve BLAST, Reciprocal BLAST, or PSI-BLAST analysis of non-redundant databases using the amino acid sequence of interest as the reference sequence. Amino acid sequence is, in some instances, deduced from the nucleotide sequence. Those polypeptides in the database that have greater than 40% sequence identity are candidates for further evaluation. Amino acid sequence similarity allows for conservative amino acid substitutions, such as substitution of one hydrophobic residue for another or substitution of one polar residue for another. When desired, manual inspection of such candidates can be carried out in order to narrow the number of candidates to be further evaluated. Manual inspection can be performed by selecting those candidates that appear to have conserved functional domains.

Conserved regions can be identified by locating a region within the primary amino acid sequence of a polypeptide described herein that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species can be adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

In particular aspects, the AOR gene exhibits at least 60%, 70%, 80%, 92%, 94%, 96%, 98%, or 99% sequence identity to SEQ ID NO: 1 or SEQ ID NO: 3.

Further provided herein are methods for the production of butanol, comprising: culturing a co-culture comprising a recombinant C1-fixing homoacetogen microorganism and a C4-producing butyrate microorganism in a culture medium in the presence of syngas, wherein the C1-fixing homoacetogen microorganism comprises a recombinant gene encoding a aldehyde ferredoxin oxidoreductase polypeptide modulated by a promoter.

In particular embodiments the co-culture of microorganisms contains at least one microorganism having at least one nucleotide sequence that encodes a gene to produce a tungsten-dependent aldehyde ferredoxin oxidoreductase (AOR) and at least one additional microorganism that encodes a gene for producing a Butyryl-CoA acetate transferase (BuCoAAT) or a Butyrate kinase (Buk). The co-culture is exposed to gaseous substrates selected from the group consisting of carbon monoxide, carbon dioxide and hydrogen gas or combinations thereof so that a C1-fixing microorganism containing an AOR gene or genes and a C4-producing microorganism containing at least one of the BuCoAAT or Buk gene under conditions effective for the co-culture to convert the gaseous substrate into butanol or/and into butyric acid so that the microorganism composition can produce butanol.

As used herein, the term "syntrophic" refers to the association of two or more different types (e.g. organisms, populations, strains, species, genera, families, etc.) of anaerobic microorganisms which form a tightly associated metabolic relationship.

As used herein, the term "co-culture" of microorganisms refers to joint incubation or incubation together, of the microorganisms. The co-culture does not require cellular population growth during the joint incubation of the microorganisms.

Figure 6:
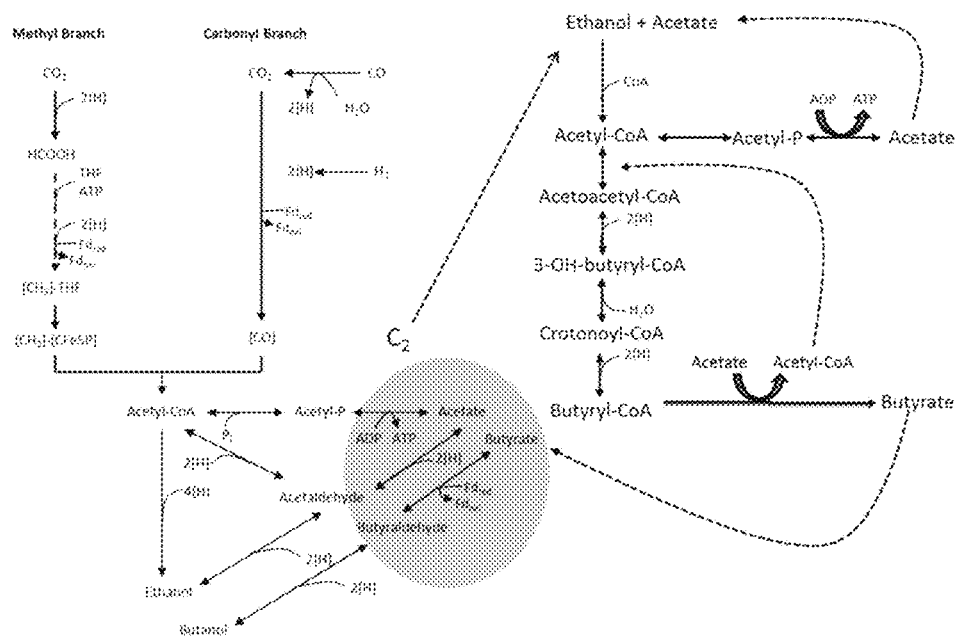
FIG. 6. Schematic pathways showing co-culture metabolism and butanol production. Homoacetogen reactions generate ethanol and acetate and butanol, from butyrate, the butyrogen product.
Figure 7:
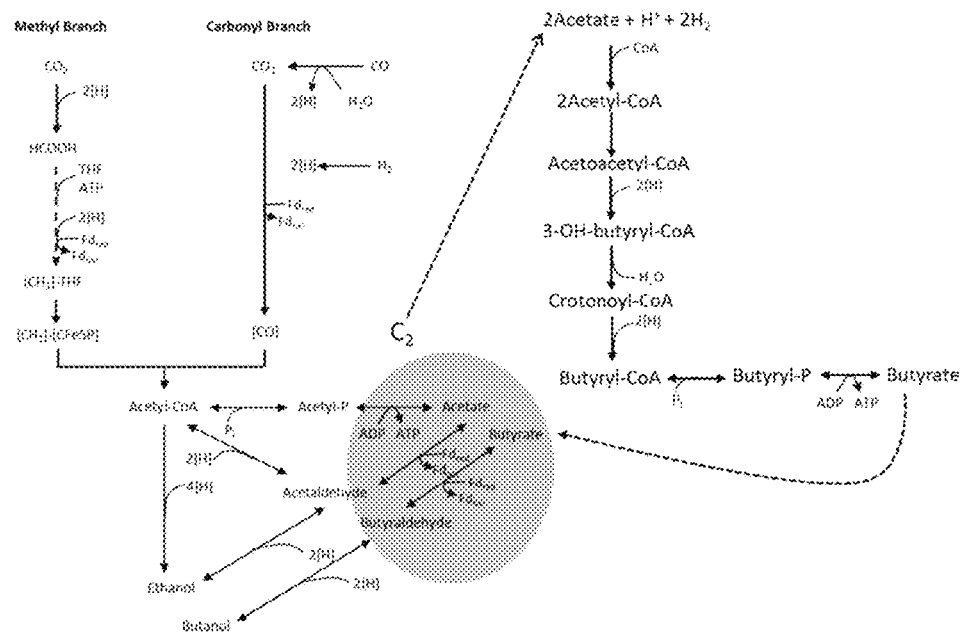
FIG. 7. Schematic pathways showing acetate production by homoacetogens coupled with its consumption (along with hydrogen gas) by the butyrogen to generate butyrate. This is followed by conversion of the butyrate to butanol by the homoacetogen organism. Butyrate is generated by native phosphotransbutyrylase and butyrate kinase activities.

In one embodiment, illustrated in FIG. 6 and FIG. 7, two types of anaerobic microorganism are utilized to create the co-cultures for production of butyrate and butanol. The first type of microorganism in the co-culture is a primary C1-fixing homoacetogenic microorganism (illustrated metabolically in FIGS. 6 and 7), which utilizes syngas as the sole carbon and electron source and produces C2 compounds such as ethanol and acetate as the dissimilatory metabolite products. The second type of microorganism in the co-culture is capable of growing on the dissimilatory metabolites of the C1-fixing homoacetogenic microorganism (ethanol and acetate) as its sole carbon and energy source to produce a C4-carbon molecule, such as butanol or butyric acid, as its primary product or together with syngas (as additional carbon and/or electron source) convert the metabolites of the C1-carbon fixing microorganism to C4-carbon molecules. This second microorganism is also referred to herein as the C4-producing butyrate microorganism (illustrated metabolically in FIGS. 6 and 7). Advantageously, the C1-fixing homoacetogenic microorganism may also be capable of converting the butyrate produced by the C4-producing microorganism into butanol and more often n-butanol (FIGS. 6 and 7). The term "butanol" refers to all four isomers of C4 alcohol (e.g. 2-butanol, isobutanol, 1-butanol and tert-butanol) and the term "n-butanol" refers to 1-butanol.

The homoacetogenic organism typically has the primary Wood-Ljungdahl pathway to convert the CO and H2/CO$_2$ from the syngas feed to ethanol and acetate which are then utilized by the butyrogens to produce butyrate. The homoacetogens can uptake the butyrate and very efficiently convert it to n-butanol because of favored thermodynamics. Such symbiosis is preferably developed to form a very close association between the $C_1$-fixing and the $C_4$-producing microorganisms so that interspecies proton and electron transfer occur very efficiently across very short distances (approximately 1 micron). This combination of microorganism co-culture and substrates vastly improves the n-butanol production over that produced by single culture (mono-) fermentations. This discovery enables high-yield production of butanol directly from syngas and leads to economical and efficient production processes for butanol from a wide range of feedstocks.

In particular embodiments the C4-producing microorganisms are butyrogens capable of growing on ethanol and/or acetate as their primary carbon source. Butyrogens refers to any microorganism capable of converting syngas intermediates, such as ethanol and acetate, and some hydrogen to primarily n-butyrate. Butyrogens of the invention utilize at least one of two distinct pathways for butyrate production—the Butyryl-CoA Acetate Transferase pathway (shown in FIG. 6) and the Butyryl Kinase (Buk) pathway (shown in FIG. 7). As can be seen from FIG. 6, the Butyryl CoA Acetyl Transferase (BuCoAAT) pathway converts ethanol and acetate to butyrate:

As shown in FIG. 7, the BuK pathway converts acetate and hydrogen to Butyrate.

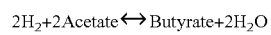

In particular embodiments a recombinant homoacetogen containing unregulated AOR activity is brought into close contact with a butyrogen to further increase the production of butanol. The co-culture of microorganisms includes a unique set of nucleotide sequences that can produce butanol from the syngas components of CO or $CO_2$ and $H_2$ at much higher concentrations than previous methods for anaerobically producing butanol with microorganisms. In other particular embodiments the homoacetogenic microorganism is cultured in a fermenter until it produces a concentration of ethanol of at least 1 g/L and the butyrogenic microorganism is added to the fermenter to produce the microorganism co-culture.

In other particular embodiments the homoacetogenic microorganism is cultured in a fermenter until it produces a concentration of ethanol of at least 1 g/L or at least 10 g/L and the butyrogenic microorganism is added to the fermenter to produce the microorganism co-culture.

In particular embodiments, *C. pharus* and *C. kluyveri* are employed. In other embodiments the co-culture includes one or more homoacetogenic microorganisms selected from the group consisting of *C. ljungdahlii, C. ragsdalei, C. autoethanongenum* and *C. coskatii*. In yet other embodiments the co-culture comprises a mixture of homoacetogenic microorganisms and a butyrogenic microorganism.

During the co-culture fermentation, the syngas-utilizing homoacetogenic organisms produce ethanol and acetate by the Wood-Ljungdahl pathway and downstream dehydrogenase reactions (FIG. 1). The butyrogenic cells consume the ethanol (by oxidation to acetyl-CoA) and the exogenous acetate produced and convert them in a condensation reaction to acetoacetyl-CoA. This reaction is carried out by thiolase, a selenium-dependent enzyme. The butyrogen converts the acetoacetyl-CoA to 3-hydroxybutyryl-CoA (3-HB-CoA) by a 3-hydroxybutyryl-CoA dehydrogenase (hbd)

using NADH(PH) as cofactor. The 3-HBCoA is dehydrated by crotonase to form crotonyl-CoA. The dehydration reaction is followed by a reduction reaction catalyzed by butyryl-CoA dehydrogenase (bcd) and NADH(PH) as cofactor and converts the crotonyl-CoA to butyryl-CoA. This reaction also involves ferredoxin and flavin adenine dinucleotide to generate the cell's PMF. The butyryl-CoA is then converted to butyrate via two possible routes, (i) by butyryl-CoA acetate transferase (BCoAAT) that transfers a CoA to acetate from butyryl-CoA (FIG. 6) or (ii) by the phosphotransbutyrylase-butyrate kinase (ptb-Buk) route (FIG. 7). Both routes are possible and results of molecular probing (data not shown) using specific primers to amplify the genes encoding butyrate production have shown that both are present in the co-cultures of consortia and only the BCoAAT is present in the two organism co-culture of *C. autoethanogenum* and the butyrogen *C. pharus*.

The butyrate produced can diffuse out of the butyrogen cells and be taken up by the homoacetogen cells. Upon butyrate uptake the homoacetogen cells can convert it to butanol by either acyl-CoA transferase activity involving NADH(PH) as cofactor, CoA synthetase activity or by direct reduction of the non-activated carboxylic acid by AOR activity. The former reactions are possible but genes encoding acyl-CoA transferase and CoA synthetase activities have not been identified in our homoacetogen genomes. Two AOR genes encoding tungsten-dependent aldehyde ferredoxin oxidoreductase activity have been identified in the *C. autoethanogenum* et al. genomes (FIGS. 4-5). Purified AOR activity has been demonstrated in several clostridial and non-clostridial (aerobic) organisms (White (1991), *Biol. Chem. Hoppe-Seyler* 372:999-1005.). A genome analysis of the two AOR genes (FIGS. 4-5) showed good conservation with the two well-characterized AOR enzymes at both the DNA and amino acid sequence levels, suggesting that these enzymes perform similar functions in vivo.

In the BCoAAT pathway ethanol and acetate are converted to butyrate through a Butyryl-CoA intermediate. Similarly, acetate plus reducing equivalents through $H_2$ oxidation are converted to butyrate through a butyryl-CoA intermediate. The pathways differ in their conversion steps from butyryl-CoA to butyrate. The BuCoAAT pathway converts butyryl-CoA to butyrate through the BCoAAT enzyme while transferring the CoA moiety to acetate to form acetyl-CoA, which can later be used to form more butyrate. At the same time the Buk pathway converts butyryl-CoA through a phosphotransbutyrylase and Buk enzyme. The tungsten-dependent aldehyde ferredoxin oxidoreductase converts butyrate directly into butyraldehyde in a two electron transfer reaction using reduced ferredoxin and tungsten. The butyraldehyde is then converted to butanol using native homoacetogen butanol dehydrogenase enzymes. Suitable butyrogens for this invention include any microorganism that contains either or both of the BuCoAAT pathway and Buk pathway and can grow on acetate and ethanol or on acetate and hydrogen as typically found in syngas. While many microorganism are known to produce butyrate from various carbohydrate sources (*C. butyricum, C. acetobutylicum, C. tyrobutyricum, C. beijerinckii, C. pasteurianum, C. barkeri, C. thermobutyricum, C. thermopalmarium, Butyrvibrio, Sarcina, Eubacterium, Fusobacterium*, and *Megasphera*), only a few are known to grow exclusively on ethanol, acetate or syngas such as *Clostridium kluyveri, Clostridium carboxidivorans, Butyribacterium methylotrophicum*, and *Clostridium pharus*.

Provided herein is a combination of the genes for tungsten-dependent aldehyde ferredoxin oxidoreductase and for the genes of a Butyryl-CoA acetate transferase and/or a Butyrate kinase such that this unique gene combination can make butanol from one or more syngas components. Tungsten-dependent aldehyde ferredoxin oxidoreductase does not occur in the butyrogenic organisms nor do the Butyryl-CoA Acetate transferase or Butyrate kinase occur in the homocetogenic organism. The genetic novelty of these gene combinations was established by identifying key genes in the butyrate production pathway using targeted gene probes. The novelty of the butyryl-CoA transferase genes in the butanologenic consortia appears to be a highly specific transferase reaction and the reduction of carboxylic acids also appears to be highly specific under the culture conditions. Hence, unique combinations of genes exist in these co-cultures that do not occur in other organisms that have been used to produce butanol. Additionally and significantly, provided herein is a recombinant homoacetogen strain with improved aldehyde ferredoxin oxidoreductase qualities and activities. During periods of AOR down-regulation, where the conversion of carboxylic acids is reduced or inhibited altogether since transcript is reduced or limited, the recombinant strain would provide unregulated gene expression and protein activity to continue the conversion of carboxylic acids to aldehydes, and thereby circumventing cell stress due to acid accumulation in the culture.

A successful syntrophic relationship between the different microorganisms require that the homoacetogens and the butyrogens are brought into close physical association with each other. In particular embodiments the C1-converting homoacetogens with the Wood-Ljundahl pathway and the tungsten-dependent aldehyde ferredoxin oxidoreductase genes AOR1 and AOR2 are brought together in an intimately mixed co-culture with the butyrogens having the BuCoAAT or the BuK genes or both sets of genes. In another embodiment of the invention the C1-converting homoacetogens will have tungsten-dependent aldehyde ferredoxin oxidoreductase genes to further increase the production of butanol in the homoacetogens. In one method of the invention, the co-culture is formed by first growing the homoacetogen species on a syngas feed. Growth of the homoacetogens continues until they produce ethanol and acetate, normally at a concentration of at least 1 g/L and more typically in a moderate concentration range of 8 to 15 g/L and preferably at a concentration of 10 g/L and a cell concentration producing an optical density (O.D.) of about 2.0. Once the homoacetogens have produced a desired concentration of ethanol and acetate and the fermenter has reached a desired O.D., the homoacetogens are inoculated with one or more selected butyrogen species that are enriched from growth on acetate, ethanol and syngas. By maintaining growth and operating conditions such as pH, dilution rate, key nutrients etc., a stable co-culture is developed that forms very close associations between the different microorganisms.

Those skilled in the art will be aware of other methods to initiate and grow the co-culture. Such methods may include the use of different substrates to first grow the butyrogen and then inoculate the fermentation medium containing the butyrogen with the homoacetogen. Another method for establishing a syntrophic association capable of converting syngas to butanol involves the growing of two or more defined cultures and establishing the pairing of these separate cultures.

Another method of pairing involves first growing the C4-producing butyrogen(s) in a fermenter using ethanol and acetate as substrates until maximum productivity targets of butyric acid has been reached. Once the maximum productivity target has been reached a seed culture of the C1-fixing homoacetogen is added directly to the fermenter containing the butyrogen culture. Syngas mass transfer to the fermentation vessel is gradually increased to balance the gas consumption of the C1-fixing homoacetogen. The ethanol or acetate used to grow the butyrogen is gradually decreased to zero as the C1-fixing homoacetogen begins to provide this substrate.

A modification of this last method of establishing a syntrophic culture involves first growing the C4-producing butyrogen culture in a fermenter with a biofilm support material that is either stationary or floating within the reactor. An example of such material is the Mutag Biochips. This method allows the butyrogen microorganism to first establish a biofilm on the carrier material thereby increasing the cell retention time versus the HRT of the fermenter. Again, target butyrogen productivity is reached before seeding the fermenter with the C1-fixing homoacetogen.

Another method to establish a syntrophic culture capable of producing butanol from syngas involves the initial mixing together of two or more cultures, one of which is a C1-fixing homoacetogen capable of growing on syngas and producing ethanol and acetate. The other culture(s) is a C4-producing butyrogen capable of converting ethanol or acetate to butyrate. The Ethanol and acetate feed can gradually be decreased to zero as the production of these substrates by the C1-fixing homoacetogens increases to balance the substrate needs of the butyrogen production.

Suitable pairings of microorganisms for the co-culture composition of this invention are identified by the presence of key genes in the pathways for the homoacetogenic and butyrogenic microorganisms. These pathways are typically identified by using targeted gene probes. The probes are targeted toward identifying the presence of genes in the consortium that encode for two tungsten-dependent aldehyde ferredoxin oxidoreductase genes, at least one BuCoAAT gene or one Buk gene. The presence or absence of these genes can be further determined using genomic DNA and suitable probes. Further description of the gene sequences are provided in the Examples.

The methods disclosed herein can be performed in any of several types of fermentation apparatus that are known to those of skill in the art, with or without additional modifications, or in other styles of fermentation equipment that are currently under development. Examples include but are not limited to conventional stirred-tank fermenters (CSTR), bubble column bioreactors (BCBR), membrane supported bioreactors (MSBR), two-stage bioreactors, trickle-bed reactors, membrane reactors, packed-bed reactors containing immobilized cells, etc. Bioreactors may also include a column fermentor with immobilized or suspended cells, a continuous flow-type reactor, a high-pressure reactor, or a suspended cell reactor with cell recycle. Furthermore, reactors may be arranged in a series and/or parallel reactor system which contains any of the above-mentioned reactors. For example, multiple reactors can be useful for growing cells under one set of conditions and generating n-butanol (or other products) with minimal growth under another set of conditions.

Establishing the necessary close association of the co-culture may be influenced by the type of bioreactor employed for practice of the invention. For example, in the case of planktonic type bioreactors the co-culture may continue in a growth phase and be passaged up to larger fermentation vessels. In the case of an MSBR, an established co-culture from a planktonic fermenter may be used to inoculate the membranes. However, an MSBR may also be inoculated by a series of inoculations that alternate between addition of the homoacetogen and addition of the butyrogen.

These apparatuses will be used to develop and maintain the C1-fixing homoacetogen and butyrogen cultures used to establish the metabolic association. The chief requirements of such an apparatus include:
 a. Axenicity;
 b. Anaerobic conditions;
 c. Suitable conditions for maintenance of temperature, pressure, and pH;
 d. Sufficient quantities of substrates supplied to the culture;
 e. Optimum mass transfer performance to supply the gases to the fermentation medium; and
 f. The end products of the fermentation can be readily recovered from the bacterial broth.

Suitable gas sources of carbon and electrons are preferably added during the inoculation. In addition to those already described these gaseous sources come from a wide range of materials and include "waste" gases such as syngas, oil refinery waste gases, steel manufacturing waste gases, gases produced by steam, autothermal or combined reforming of natural gas or naphtha, biogas and products of biomass, coal or refinery residues gasification or mixtures of the latter. Sources also include gases (containing some $H_2$) which are produced by yeast, clostridial fermentations, and gasified cellulosic materials. Such gaseous substrates may be produced as byproducts of other processes or may be produced specifically for use in the methods disclosed herein. Those of skill in the art will recognize that any source of substrate gas may be used in the practice of the methods disclosed herein, so long as it is possible to provide the microorganisms of the co-culture with sufficient quantities of the substrate gases under conditions suitable for the bacterium to carry out the fermentation reactions.

In one embodiment of the invention, the source of CO, $CO_2$ and $H_2$ is syngas. Syngas for use as a substrate may be obtained, for example, as a gaseous product of coal or refinery residues gasification.

In addition to those sources as described, syngas can be produced by gasification of readily available low-cost agricultural raw materials expressly for the purpose of bacterial fermentation, thereby providing a route for indirect fermentation of biomass to alcohol. There are numerous examples of raw materials which can be converted to syngas, as most types of vegetation could be used for this purpose. Suitable raw materials include, but are not limited to, perennial grasses such as switchgrass, crop residues such as corn stover, processing wastes such as sawdust, byproducts from sugar cane harvesting (bagasse) or palm oil production, etc. Those of skill in the art are familiar with the generation of syngas from such starting materials. In general, syngas is generated in a gasifier from dried biomass primarily by pyrolysis, partial oxidation, and steam reforming, the primary products being CO, $H_2$ and $CO_2$. The terms "gasification" and "pyrolysis" refer to similar processes; both processes limit the amount of oxygen to which the biomass is exposed. The term "gasification" is sometimes used to include both gasification and pyrolysis.

Combinations of sources for substrate gases fed into the fermentation process may also be utilized to alter the concentration of components in the feed stream to the bioreactor. For example, the primary source of CO, $CO_2$ and $H_2$ may be syngas, which typically exhibits a concentration ratio of 37% CO, 35% $H_2$, and 18% $CO_2$, but the syngas may be supplemented with gas from other sources to enrich the level of CO (i.e., steel mill waste gas is enriched in CO) or $H_2$.

The co-cultures disclosed herein are cultured and used under anaerobic conditions. As used herein, "anaerobic conditions" means the level of oxygen ($O_2$) is below 0.5 parts per million in the gas phase of the environment to which the microorganisms are exposed. One of skill in the art will be familiar with the standard anaerobic techniques for culturing these microorganisms (Balch and Wolfe (1976) *Appl. Environ. Microbiol.* 32:781-791; Balch et al., 1979, *Microbiol. Rev.* 43:260-296), which are incorporated herein by reference. Other operating conditions for the established co-culture will usually include a pH in a range of 5 to 7.

A suitable medium composition used to grow and maintain co-cultures or separately grown cultures used for sequential fermentations, includes a defined media formulation. The standard growth medium is made from stock solutions which result in the following final composition per liter of medium. The amounts given are in grams unless stated otherwise. Minerals: NaCl, 2; $NH_4Cl$, 25; KCl, 2.5; $KH_2PO_4$, 2.5; $MgSO_4.7H_2O$, 0.5; $CaCl_2.2H_2O$, 0.1. Trace metals: $MnSO_4.H_2O$, 0.01; $Fe(NH_4)_2(SO_4)_2.6H_2O$, 0.008; $CoCl_2.6H_2O$, 0.002; $ZnSO_4.7H_2O$, 0.01; $NiCl_2.6H_2O$, 0.002; $Na_2MoO_4.2H_2O$, 0.0002; $Na_2SeO_4$, 0.001; $Na_2WO_4$, 0.002. Vitamins (in mg): Pyridoxine-HCl, 0.10; thiamine-HCl, 0.05; riboflavin, 0.05; calcium pantothenate, 0.05; thioctic acid, 0.05; p-aminobenzoic acid, 0.05; nicotinic acid, 0.05; vitamin $B_{12}$, 0.05; mercaptoethane sulfonic acid, 0.05; biotin, 0.02; folic acid, 0.02. A reducing agent mixture is added to the medium at a final concentration of 0.1 g/L of cysteine (free base); and 0.1 $Na_2S.2H_2O$. Medium compositions can also be provided by yeast extract or corn steep liquor or supplemented with such liquids.

In general, fermentation of the co-culture will be allowed to proceed until a desired level of butanol is produced in the culture media. Preferably, the level of butanol produced is in the range of 2 g/L to 7.5 g/L and most preferably in the range of 6 g/L to 15 g/L. Alternatively, production may be halted when a certain rate of production is achieved, e.g. when the rate of production of a desired product has declined due to, for example, build-up of bacterial waste products, reduction in substrate availability, feedback inhibition of by-products, reduction in the number of viable bacteria, or for any of several other reasons known to those of skill in the art. In addition, continuous culture techniques exist which allow the continual replenishment of fresh culture medium with concurrent removal of used medium, including any liquid products therein (i.e. the chemostat mode). Also, techniques of cell recycle may be employed to control the cell density and hence the volumetric productivity of the fermenter.

The products that are produced by the microorganisms of this invention can be removed from the culture and purified by any of several methods that are known to those of skill in the art. For example, butanol can be removed by distillation at atmospheric pressure or under vacuum, by adsorption or by other membrane based separations processes such as pervaporation, vapor permeation and the like.

This invention is more particularly described below in the Examples set forth herein and are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The terms used in the specification generally have their ordinary meanings in the art, within the context of the invention, and in the specific context where each term is used. Some terms have been more specifically defined to provide additional guidance to the practitioner regarding the description of the invention.

EXAMPLES

Genome Sequence Analysis

Analysis of the *C. autoethanogenum*, *C. ragsdalei*, *C. ljungdahlii*, *C. coskatii* and *C. carboxidivorans* genome sequences was performed using the ERGO bioinformatics suite (Integrated Genomics, Arlington Heights, Ill.) and BLASTX. The genome analysis revealed two genes annotated as having tungsten-dependent, aldehyde ferredoxin oxidoreductase activity (Ec 1.2.7.5).

Strains

*Clostridium autoethanogenum* strain DSM 10061 (Abrini J, Naveau H, Nyns E-J, *Arch. Microbiol.* 1994, 4:345-351), *C. ragsdalei* P11 (ATCC BAA-622) (WO 2008/028055), *C. coskatii* PS-02 (ATCC-PTA10522) (US 2011/0229947), *C. carboxidivorans* strain "P7" (ATCC-BAA-624) (US 2007/0275447), *C. ljungdahlii* was obtained from ATCC (strain ATCC 55383/DSM 13528/PETC; Tanner R S et al. *Int J Syst Bacteriol.* (1993) 43(2):232-236).

*E. coli* JW5272-1 Δ(araD-araB)567, ΔlacZ4787(::rmB-3), λ⁻, ΔydhV748::Kan, rph-1, Δ(rhaD-rhaB)568, hsdR514. Baba et al (2006) Mol. Syst. Biol. 2:1-11 (The Keio Collection). The *E. coli* AOR mutant was obtained from the Yale Culture Stock Collection (New Haven Conn.). *E. coli* DH10B (Life Technologies, Carlsbad, Calif.; dam⁺, dcm⁺, mcrABmrr⁻) and *E. coli* BL21 (Life Technologies, Carlsbad, Calif.; dcm⁻, dam⁺, mcrAB mrr⁺) were routinely used for propagating replicating plasmids.

Vectors

Suitable vectors are described in Table 1 with some general features. The vectors were used to express Clostridial (e.g. *C. autoethanogenum*) aldehyde ferredoxin oxidoreductase genes in an *E. coli* ydhV mutant to demonstrate butyrate conversion to butanol function in vivo. High-copy expression vector pCKAR192 contained AOR2 expressed from the strong Clostridial promoter PcooS. *E. coli-Clostridium* conjugative vector pCKAR192T2 contained the same expression construct as pCKAR192 but also expressed the basis of mobilization derived from RP4 (Parke 1990, *Gene* 93:135-137). High-copy expression vector pCKAR214 contained AOR1 expressed from the strong Clostridial promoter Ppta-ack. *E. coli-Clostridium* conjugative vector pCKAR214T1 contained the same expression construct as pCKAR214 but also expressed the basis of mobilization derived from RP4 (Parke 1990, *Gene* 93:135-137). *E. coli-clostridium* shuttle vector pCK232AOR1, contained the same elements as pCKAR214 but additionally contained the rep1 origin of replication and the Ppta-AOR1 expression cassette from *C. autoethanogenum*. pCK232 lacks the Ppta-AOR1 expression cassette.

TABLE 1

Plasmids used and their key gene elements.

| Plasmids | Key genetic elements | Antibiotic resistance |
| --- | --- | --- |
| pCKAR192 | pMB1, Pcoos-AOR | Ampicillin |
| pCKAR192T2 | pMB1, RP4 oriT, Pcoos-AOR | chloramphenicol, Ampicillin |
| pCKAR214 | pMB1, Ppta-AOR | Ampicillin |
| pCKAR214T1 | pMB1, RP4 oriT, Ppta-AOR | chloramphenicol, Ampicillin |

TABLE 1-continued

Plasmids used and their key gene elements.

| Plasmids | Key genetic elements | Antibiotic resistance |
|---|---|---|
| pCK232 | pMB1, rep1, RP4 oriT | Kanamycin, Ampicillin |
| pCK232AOR1 | pMB1, rep1, RP4 oriT, Ppta-AOR | Kanamycin, Ampicillin |

Media

*E. coli* was grown in LB medium which was composed of 10 g/L tryptone, 5 g/L yeast extract and 10 g/L NaCl.

LB ampicillin and LB chloramphenicol medium was composed of LB medium containing filter sterilized 100 μg ampicillin sulfate and 50 μg water soluble chloramphenicol per ml, respectively.

*E. coli* was grown on 2×YT agar which was composed of 16 g per liter tryptone, 10 g per liter yeast extract and 5.0 g per liter NaCl.

*E. coli* minimal medium (M9) contained the following per liter: 200 ml 5×M9 salts; 2 ml 1 M $MgSO_4$; 20 ml of a sterile 20% glucose solution; 100 ul of 1 M $CaCL_2$. The 5×M9 salts contained the following (per liter): $Na_2HPO_4 \cdot 7H_2O$, 64 g; $KH_2PO_4$, 15 g; NaCl, 2.5 g; $NH_4CL$, 5 g.

For M9 medium containing ampicillin or chloramphenicol, 50 ml M9 medium was prepared as above and was supplemented with ampicillin sulfate or water soluble chloramphenicol at 50 μg per liter medium.

2×YT ampicillin (Ap) and chloramphenicol (Cm) were composed of 2×YT agar (1.5%) containing 100 μg (Ap) and 50 μg (Cm) respectively, per ml of agar.

*Clostridium* fermentation medium was made anaerobically from concentrated vitamin, mineral and metals stocks with the compositions shown in Tables 2 and 3a-d.

*Clostridium* plating medium was composed of fermentation medium containing 5 g/L fructose (filter-sterilized and added post autoclaving), 10 g/L yeast extract and 15-20 g/L agar.

TABLE 2

Fermentation Medium Compositions

| Components | Amount per liter |
|---|---|
| Mineral solution, See Table 2(a) | 25 ml |
| Trace metal solution, See Table 2(b) | 10 ml |
| Vitamins solution, See Table 2(c) | 10 ml |
| Yeast Extract | 0.5 g |
| Adjust pH with NaOH | 5.8 |
| Reducing agent, See Table 2(d) | 2.5 ml |

TABLE 3(a)

Mineral Solution

| Components | Concentration (g/L) |
|---|---|
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

TABLE 3(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 3(c)

Vitamin Solution

| Components | Concentration (mg/L) |
|---|---|
| Pyridoxine•HCl | 10 |
| Thiamine•HCl | 5 |
| Riboflavin | 5 |
| Calcium Pantothenate | 5 |
| Thioctic acid | 5 |
| p-Aminobenzoic acid | 5 |
| Nicotinic acid | 5 |
| Vitamin $B_{12}$ | 5 |
| Mercaptoethanesulfonic acid | 5 |
| Biotin | 2 |
| Folic acid | 2 |

TABLE 3(d)

Reducing Agent

| Components | Concentration (g/L) |
|---|---|
| Cysteine (free base) | 40 |
| $Na_2S \cdot 9H_2O$ | 40 |

Example 1

Acetate assimilation pathways in syngas-utilizing *Clostridia*

Metabolic reconstruction of the Wood-Ljungdahl pathway from genome sequences of syngas-utilizing *Clostridia* (including *C. autoethanogenum*) identified three possible routes to carboxylic acids and alcohols (FIG. 1). The product of the Wood-Ljungdahl pathway is acetyl-CoA which results from the three-component reaction of CoA, methyl-corrinoid iron sulfur protein and CO of the carbon monoxide dehydrogenase acetyl-CoA synthase. Acetyl-CoA can be directly converted to ethanol by the acetyl-CoA reductase (U.S. Pat. No. 8,039,239), a bifunctional enzyme requiring NADPH and zinc in a four-electron reduction reaction. It can alternatively be converted to the aldehyde by an acetylating aldehyde dehydrogenase. The aldehyde can subsequently be converted to ethanol by variety of alcohol dehydrogenases. An alternate route for acetate assimilation involves the conversion of acetyl-CoA to acetyl-phosphate by phosphotransacetylase which in turn generates acetate by acetate kinase. The latter reaction generates an ATP which potentially acts as an important valve for energy balance by substrate-level phosphorylation when cells are growing on dissolved gases. While generation of an ATP is beneficial to the cell, by balancing the ATP used in the generation of formyl-tetrahydrofolate of the methyl branch of the pathway, acetate accumulation is detrimental to cells particularly when the free acid concentration reaches a threshold level, typically at about 5 g/L when fermentations are run at or near the pKa of the acids (~4.75). Another route to acetate assimilation can occur by conversion to the aldehyde using aldehyde ferredoxin oxidoreductase. Two genes annotated as tungsten-dependent, aldehyde ferredoxin oxidoreductase (1.2.7.5) were identified in the *C. autoethanogenum* et al. genomes and their DNA and amino acid sequences are shown in FIGS. 3 and 4, respectively. These genes encode a somewhat unusual function by performing the conversion of a non-activated carboxylic acid (e.g. acetate and butyrate) directly to an aldehyde, thus potentially extending the metabolic versatility of *C. autoethanogenum* et al. to generate alcohols. While this reaction is thermodynamically uphill, the coupling of the downstream dehydrogenation reaction makes it very favorable. The aldehydes formed in turn get converted to alcohol using nicotinamide cofactors (NADH (PH) by the wide variety of alcohol dehydrogenases identified in the *C. autoethanogenum* et al. genomes. While the conversion of an acid to an aldehyde is endergonic and likely requiring high energy electrons to be transferred to ferredoxin, this strategy would also reduce acid stress and the consequent dissipation of the chemiosmotic potential, which is known to be the major source of energy for these organisms. Moreover, the assumed in vivo ratio of acid to aldehyde is predicted to be very high and thus would also favor the conversion of the acid to alcohol by the aldehyde ferredoxin oxidoreductase. The energetics of the reaction requiring ferredoxin suggest that a high energy electron carrier is required for these reactions to take place but recent experimental data suggest that these anaerobes have ways of altering the redox requirements to achieve highly desirable endergonic reactions by redox coupling and bifurcation (Wang et al. *J. Bacteriol.* 195 (19): 4373-4386).

Example 2

Construction of AOR2 Expression Plasmid pCKAR192

To confirm functional activity of the open-reading frames (ORF) of the AOR2 gene a novel construct was generated whereby the AOR2 ORF was operably linked to a constitutively expressed, strong heterologous Clostridial promoter, Pcoos (derived from the carbon-monoxide-electron transfer protein region U.S. Pat. No. 8,039,239). The 2.307 kb Pcoos-AOR2 expression cassette was synthesized with SphI, HindIII and KpnI engineered at the 5' and 3' ends and ligated to a modified pMB1-based high-copy number vector for replication in *E. coli*. Ampicillin was used as the selection agent at 100 ppm (FIG. 2A). This expression vector was designated pCKAR192 (Table 1).

Example 3

Construction of *E. coli-Clostridium* Shuttle Vector pCK192T2

For generation of an *E. coli-Clostridium* shuttle vector, pCKAR149 was used as the cloning vehicle. pCKAR149 contains dual replicons for replication in *E. coli* and *C. autoethanogenum* et al. and dual antibiotic resistances. The resistance gene for *Clostridium* selection, chloramphenicol, was expressed from a strong, constitutively-expressed native promoter and can be used as primary selection in *C. autoethanogenum*. The 2.307 kb Pcoos-AOR2 cassette was released from pCKAR192 with SphI and ligated into SphI-digested pCKAR149. Putative recombinant plasmids were screened and confirmed by restriction digestion using SphI and PCR using primers that amplified the cassette (FIG. 2A). The cassette was also subjected to double-strand gene sequencing to confirm authenticity of the Pcoos-AOR2 DNA. The final construct was designated pCKAR192T2 (Table 1).

Example 4

Construction of Ppta-AOR1 Expression Plasmid pCKAR214

For AOR1 expression a novel construct was generated using the strong clostridial promoter Ppta (derived from the phosphotransacetylase/acetate kinase region) operably linked to the AOR1 ORF. The 2.298 kb Ppta-AOR1 expression cassette was synthesized and ligated to a modified pMB1-based high-copy number vector for replication in *E. coli*. Ampicillin was used as the selection agent at 100 ppm. The restriction enzyme site EcoRI was engineered at the 5' ends for downstream sub-cloning into suitable *E. coli-Clostridium* shuttle vectors. The final construct expressing the AOR1 gene was designated pCKAR214 (FIG. 3, left; Table 1).

Example 5

Construction of Ppta-AOR1 *E. coli-Clostridium* Shuttle Vector, pCKAR214T1

For generation of an *E. coli-Clostridium* shuttle vector containing Ppta-AOR1, pCKAR149 was used as the cloning vehicle as described in Example 3. It contains dual replicons for replication in *E. coli* and *C. autoethanogenum* and dual antibiotic resistances as well as the basis of mobilization for DNA transfer via conjugation but can also be electroporated into recipient cells. The 2.307 kb Ppta-AOR1 cassette was released from pCKAR214 with EcoRI and ligated to EcoRI-digested pCKAR149. Putative recombinant plasmids were selected on chloramphenicol, screened and confirmed by restriction digestion using EcoRI and PCR using primers that amplified the cassette. The cassette was also subjected to double-strand gene sequencing to confirm authenticity of the Ppta-AOR1 DNA. The final construct was designated pCKAR214T1 (FIG. 3B; Table 1).

Example 6

Butyrate Production Using the Butyryl-CoA Acetate Transferase Pathway

The butyrogens in co-culture with *C. autoethanogenum* have two pathways for the generation of butyrate. Ethanol-oxidizing butyrogens such as *C. kluyveri* will consume six moles ethanol and 4 moles acetate to form 5 moles acetoacetyl-CoA via thiolase (2.3.1.16). The acetoacetyl-CoA is then reduced to 3-hydroxybutyryl-CoA in a reaction catalyzed by 3-hydroxybutyryl-CoA dehydrogenase (1.1.1.157). 3-hydroxybutyryl-CoA is dehydrated by crotonase (4.2.1.17) to form crotonyl-CoA. The conversion of crotonyl-CoA involves electron bifurcation and a complex of ferredoxin, NADH, and FAD to generate the chemiosmotic potential essential for cell viability (Wang et al., *J.*

Bacteriol. 192:5115-5123, 2010). This reaction is carried out by butyryl-CoA dehydrogenase (1.3.8.1 or formerly 1.3.99.2) and the EtfAB proteins. The final step to butyrate production is shown in FIG. 6. and involves a transferase reaction that converts free acetate to acetyl-CoA with the release of butyrate. One of the butyrogen (*C. pharus*) genomes has been sequenced and the gene encoding a butyryl-CoA acetate transferase activity (2.8.3.8) has been identified (Seq. ID No. 7).

Example 7

Butyrate Production Using the Phosphotransbutyrylase-Butyrate Kinase Pathway

A second pathway butyrogens use for butyrate production involves phosphotransbutyrylase and butyrate kinase (FIG. 7). Some organisms contain both butyryl-CoA acetate transferase and butyrate kinase genes such as identified in the *Clostridium carboxidivorans* genome sequence (A. Reeves unpublished). Other butyrogenic organisms have one or the other system. The steps in the formation of butyryl-CoA are more or less identical in the two systems and vary only in the final steps of butyrate production (FIGS. 6-7). Butyryl-CoA is converted to butyryl-phosphate catalyzed by phosphotransbutyrylase (2.3.1.19). Butyrate kinase (2.7.2.7) converts butyryl-P to butyrate while generating ATP, similar to the acetate kinase reaction. In our butanol-producing co-cultures the genes encoding phosphotransbutyrylase and butyrate kinase activity have been detected using gene-specific primers.

Example 8

AOR1, AOR2, BCoAAT, and Buk Gene Amplification with Co-Culture DNA

PCR primers were designed from the genome sequences of AOR1 (SEQ ID NO: 1), AOR2 (SEQ ID No: 3), BCoAAT (SEQ ID NOS: 7-8), and Buk (SEQ ID NOS. 9-11) to confirm the presence or absence of these genes in mono and co-culture fermentations. The primer sequences were: AOR1-A-forward (SEQ ID NO: 19): 5'-ACTTGGATTAT-GTATTTTTACA-3'; AOR1-A-reverse (SEQ ID NO: 20): 5'-TGAACTATCTATGCCTGCTTTT-3'; AOR2-A-forward (SEQ ID NO: 21): 5'-AAGAAAGAACTTGCAAATCA-3'; AOR2-A reverse (SEQ ID NO: 22): 5'-CGGAGCTCCAGT-TAAAGGA-3'; BCoAAT forward (SEQ ID NO: 23): 5'-AGCCATGCTAGC TCCTCTCATGTA-3';BCoAAT reverse (SEQ ID NO: 24): 5'-GGAGTATCAACCGAT TAT-TCACAG-3'; Buk forward (SEQ ID NO: 25): 5'-GATGGT-TCTACACTT CAGCTT-3'; and Buk reverse (SEQ ID NO: 26): 5'-GAT ATC ATT TCT GAA TGT ATA CCC-3'. Primers were targeted to unique regions within each AOR gene where little or no overlap occurred so that amplicons would yield unique products. For the butyryl-CoA acetate transferase and butyrate kinase genes primers were designed from multiple sequences with degeneracies to allow amplification of the broadest variety of butyrate-producing organisms in the consortium. The cycling reactions tested a gradient of temperatures from 45° C. to 61° C. For all primer sets tested, the temperature range of 53° C.-56° C. gave strong amplicons with no observable background products seen on agarose gels or using melting curve analysis in qPCR. The cycling conditions were: 1 cycle at 94° C. for 3 minutes followed by 30 cycles at 94° C. for 1 minute to denature gDNA, 30 seconds annealing at a gradient of 45° C.-61° C. and an extension at 72° C. for 30 seconds. The final extension step was at 72° C. for 7 minutes. The results of PCR using the four best primer sets and consortia gDNA are shown in FIG. 8. For AOR1, using primer set AOR1-A the amplicon was the expected size of 198 bp (FIG. 8, top, left) and for AOR2, primer set AOR2-A gave a unique amplicon of the expected size of 201 bp (FIG. 8, bottom, left). The butyrogen primer sets BCoAAT and Buk were also tested with DNA extracted from the co-culture fermentation. The BCoAAT primer set gave the expected size amplicon of 715 bp (FIG. 8, top, right) while the Buk primer set gave the expected amplicon of 168 bp (FIG. 8, bottom, right).

Example 9

Monoculture Fermentation Conditions for Testing AOR1 and AOR2 Gene Expression

Figure 9:
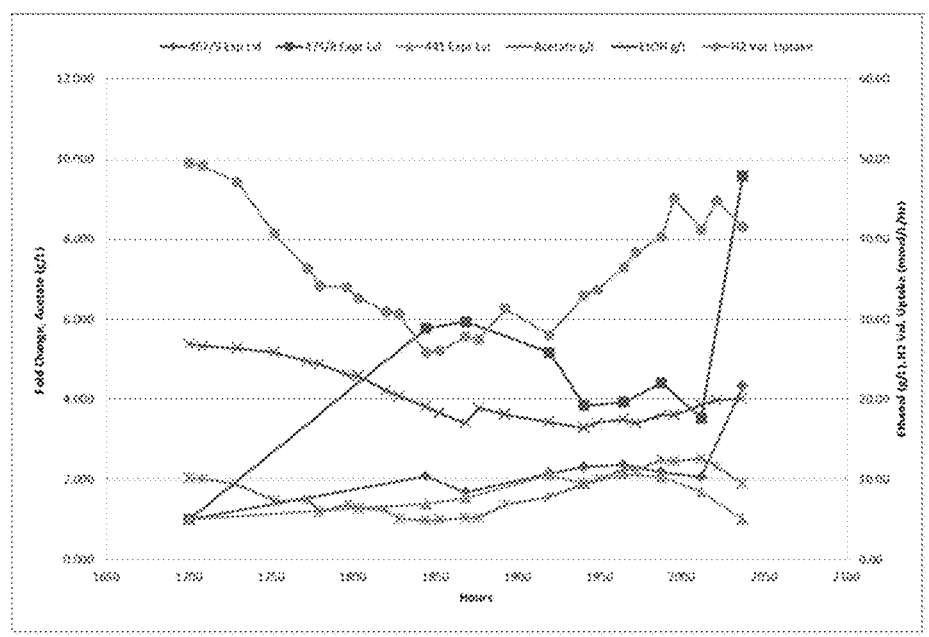
FIG. 9. Graph illustrating AOR1 and AOR2 gene expression and ethanol and acetate production in *C. autoethanogenum* during syngas co-fermentation. For gene expression analysis, using RT-qPCR (presented as fold-change), primer set 467/9 targeted AOR2-A (SEQ ID NO:14), primer set 474/478 targeted AOR1-A (SEQ ID NO: 14), and primer set 441 a targeted *C. autoethanogenum* hydrogenase.

A 10-liter syngas fermentation was run containing *C. autoethanogenum* DSM 10061 for more than 2000 hours (FIG. 9). The *C. autoethanogenum* culture reached an optical density of 2.2 after several hundred hours growing on minimal medium containing syngas with a composition of $H_2$-64.7%, CO-16.2%, $CO_2$-11.7%, and $CH_4$-6.04% (mol %), a gas flow rate of 300-500 mL/min with agitation between 500-600 rpm, and a HRT of 2.5 days during the time period for which samples for gene expression were collected. The ethanol concentrations fluctuated between 20 and 30 g/L and the acetate concentrations fluctuated between 5 and 10 g/L over the course of the fermentation. Samples for AOR1 and AOR2 gene expression were taken at nine different time points between 1700 and 2050 hours into the fermentation when the volumetric $H_2$ gas uptake started to fluctuate considerably (FIG. 9). The primers sets and sequences used for gene expression analysis (presented as fold change) shown in the figure are: 467/469, AOR2-forward (SEQ ID NO: 21): 5'-AAGAAAGAACTTG-CAAATCA-3'; AOR2-reverse (SEQ ID NO: 22): 5'-CG-GAGCTCCAGTTAAAGGA-3'; 474/478, AOR1-forward (SEQ ID NO: 19): 5'-ACTTGGATTATGTATTTTTACA-3'; AOR1-reverse (SEQ ID NO: 20): 5'-TGAACTATCTATGC-CTGCTTTT-3'; 441, iron-only hydrogenase-forward (SEQ ID NO: 27): 5'-TGT GAA CGT CCT GAA ATG AAA G-3'; iron-only hydrogenase reverse (SEQ ID NO: 28): 5'-AGT GCC TGC ACC AGA ATA AGT T-3'.

Example 10

AOR1 and AOR2 Gene Expression in a *C. autoethanogenum* Monoculture Fermentation During most of the 10-L syngas fermentation using a monoculture of *C. autoethanogenum* the volumetric productivity rate remained high (>0.4 g/L/h). Samples were taken between 1700 and 2050 hours for RT-PCR analysis using primers AOR1-A and AOR2-A. Additionally, four *C. autoethanogenum* hydrogenase genes were tested for gene expression during the time course fermentation to see how they trended with AOR gene expression (FIG. 9). Cells were quickly pelleted and re-suspended in RNA protect solution for 5 minutes and quick frozen in liquid nitrogen. Frozen cells were kept at −80° C. until needed. Total RNA was extracted using the RNA easy kit (Qiagen, Valencia, Calif.). A DNAse treatment step was included to ensure that all genomic DNA was degraded before cDNA was generated. A total cDNA reaction was performed on 50 ηg of RNA and purified using column chromatography. Fifty ηg of purified cDNA from nine sample points were used in RT-PCR (in triplicate reactions) using an Eppendorf Realplex with built-in statistical software (Eppendorf NA, Happauge, N.Y.) and primer sets AOR1-A (primer set 474/478), AOR2-A (primer set 467/469), Hyg-1 (primer set 431), Hyg-2 (primer set 435), Hyg-3 (primer set 437) and Hyg-4 (primer set 441). The 16s rDNA and recA genes were used as reference and internal standards, respectively (data not shown). Primer sequences 474/478, 467/469, and 441 see Example 9. Primer sequences for the three additional hydrogenases are: Hyg-1 (431-forward) (SEQ ID NO: 29): 5'-GCCCGATATAAATC-CTCTTT-3'; (431-reverse; (SEQ ID NO: 30): 5'-CCAACAAAAATTCCATGATT-3'; Hyg-2 (435-forward; (SEQ ID NO: 31): 5'-CTACAATTTTAAACGCT-GCA-3'; (435-reverse; (SEQ ID NO: 32)): 5'-GCTCTG-GCACTGTTTGTTCTA-3'; Hyg-3 (437-forward; (SEQ ID NO: 33): 5'-TGA TAC AAA CTT TGG TGC AG-3'; and (437-reverse; (SEQ ID NO: 34): 5'-ATA TAG CTC CAG CCA TCT GA-3'.

During the 350-hour sampling period, the transcript levels were normalized using 16s RNA as a reference gene allowing only fold changes to be determined. Relative expression levels were discernible and trends determined indicating the level of expression during the course of the sampling period. During the first 150 hours of sampling both AOR genes are expressed at a higher level (2-6-fold) than the preceding period. During this time the $H_2$ gas uptake was declining rapidly. The increase in AOR gene expression is followed by a 150-hour period of a discernible decrease in expression of AOR2 gene and a slight change in AOR1 gene expression. $H_2$ gas uptake stabilized during most of this period before increasing significantly. Preceding the AOR2 decline was a dramatic $H_2$ gas uptake decline. At 2000 hours both AORs are dramatically upregulated along with the $H_2$ gas uptake before the fermentation ceased. The cell density did not change significantly during this fermentation period whereas gas uptake fluctuated indicating a regulated response of the AOR genes to process parameters and metabolite production (FIG. 9).

Example 11

Co-Culture Fermentation Conditions for Testing AOR Gene Expression

A 100-liter fermentation experiment was run in order to establish a syntrophic pairing of a type strain homoacetogen, *C. autoethanogenum*, and a mixed culture of butyrogens. The fermentation was seeded with 8.5 L of a previously combined co-culture of the homoacetogen, *C. autoethanogenum*, and butyrogen that had already been running under stable conditions. The fermentation was maintained on minimal medium (Table 2) and fed syngas with a composition of $H_2$-64.2%, CO-16%, $CO_2$-12.4%, and $CH_4$-5.9% (mol %), a gas flow rate of 2400-2900 mL/min with an agitation of between 360 and 500 rpm. Cell recycle was used on this fermentation with a hydraulic retention time of 1.6 days and a mean cell retention time of 2.5 days. The ethanol and acetate concentrations during the 280 hr sampling period were between 2-3.5 g/L and 2.5-4 g/L, respectively, prior to the decline in $H_2$ gas uptake. Butanol and butyrate concentrations of 5-7.4 g/L and 2.1-4 g/L, respectively, were achieved during this same period prior to $H_2$ gas uptake decline. On average more than 70% of the syngas electrons consumed were converted to butanol and butyrate over the sampling period. For RT-PCR experiments, six samples were taken during the co-culture fermentation from 144-1008 hours (FIG. 10).

Example 12

AOR2 Gene Expression in a Butanol Co-Culture Fermentation

Figure 10:
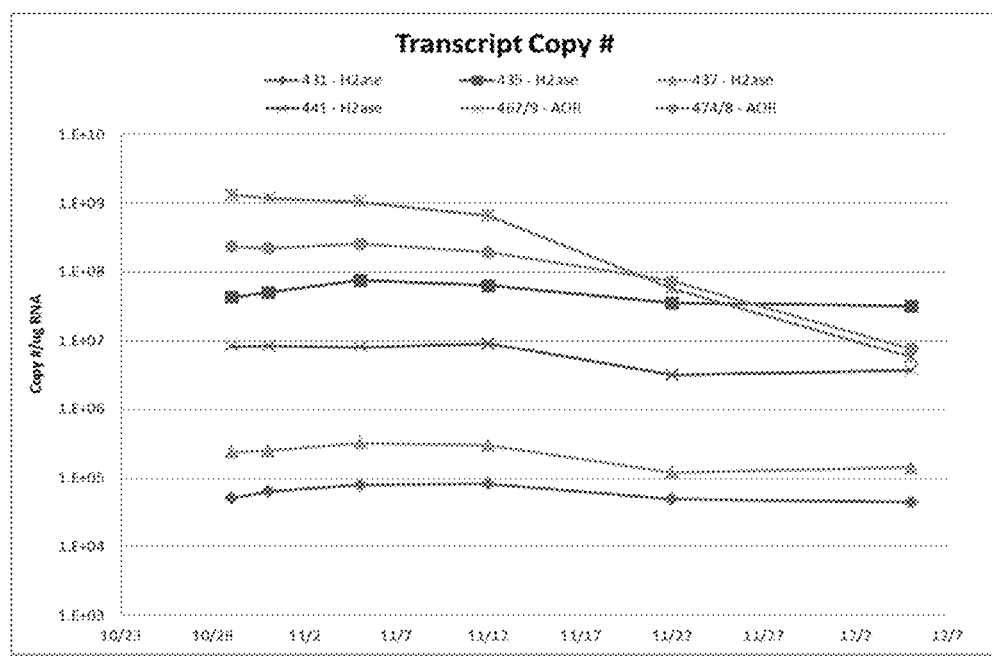
FIG. 10. Graph illustrating quantitative gene expression of *C. autoethanogenum* AOR and hydrogenase genes during a butanol co-fermentation run over the course of >900 hours. Transcript copy number at six different time points is shown. For gene expression analysis using RT-qPCR the following primer sets were used to calculate copy number/µg RNA throughout the fermentation: 467/9 targeted AOR2; 474/8 targeted AOR1; 431 targeted a NiFe hydrogenase; 435 targeted an iron-only hydrogenase; 437 targeted a second iron-only hydrogenase; and 441 targeted a third iron-only hydrogenase found in the *C. autoethanogenum* chromosome.

The *C. autoethanogenum* AOR2 gene was highly expressed (~1×10$^9$ copies/µg RNA) throughout the 860 hours of the sampling period until the end of the fermentation but was noticeably down-regulated from 480 hours into the fermentation until the end of the fermentation (FIG. 10; primer set 467/469). The volumetric gas uptake and most other measured parameters were in decline including ethanol, butanol and butyrate production during this period. The acetate concentration increased significantly (>10 g/L) which could be explained by the lowered AOR expression (i.e. poor carboxylic acid conversion). Gene expression analysis was also performed on the six identified *C. autoethanogenum* hydrogenase genes (primer sets 431, 433, 435, 437, 440, 441). All six hydrogenases showed the same general expression pattern (data only shown for 431, 435, 437, 441). During the first 150 hours of sampling (from 144-294 hours into the fermentation) the $H_2$ expression increased slightly as gas consumption increased. From 480-720 hours into the fermentation expression of hydrogenase expression noticeably decreased. The hydrogenase expression levels remained flat from 720 hours to the end of the fermentation while the AOR expression levels continued to decrease (FIG. 10).

Example 13

*E. coli* Growth Conditions for Testing Heterologous AOR Activity

*E. coli* JW5272-1 is an aldehyde ferredoxin oxidoreductase mutant containing an inserted Kn-resistance gene in the ydhV gene. ydhV is part of a seven-gene operon (ydhY-ydhT) encoding a heptameric oxidoreductase that is responsive to FNR, the anaerobic metabolism regulator. It is not known what the substrate(s) are involved in the redox reactions but there is an apparent defect in the anaerobic metabolism of five sulfur sources (Partridge J, et al., 2008, *Microbiology*, 154:608-618). While annotated as such, the phenotype does not appear to be involved in the conversion of short-chained carboxylic acids to aldehydes. Nonetheless, pCKAR192 was transformed into *E. coli* JW5272-1 to remove the possibility of any putative background aldehyde ferredoxin oxidoreductase activity. M9 minimal medium was used throughout to grow the *E. coli* strain containing pCKAR192 but the medium was supplemented with the following nutrients to take into account the likely anaerobic requirements for highly expressed AOR activity: 1× trace metals mix as described in Table 3b, 1× vitamin mix as described in Table 3c, $Na_2WO_4$ at a final concentration of 20 µM, $NaNO_3$ at a final concentration of 100 µM, and $Na_2S$ at a final concentration of 1 mM. For testing the conversion of acetate and butyrate to alcohols both were added as the sodium salt at a final concentration of 22 mM and 27 mM, respectively. Cells were first grown to mid-log phase (OD ~0.8) anaerobically using glucose as the sole carbon and energy source in M9 minimal medium without supplementation before transfer into the same medium containing the supplements described above. Either acetate or butyrate was added to the *E. coli* cultures containing plasmids pCKAR162 and pCKAR192. Cultures contained ampicillin sulfate at 20 ppm for plasmid maintenance. Cells were grown under strictly anaerobic conditions without shaking with added sodium sulfide (up to 2 mM throughout the testing period) to remove any traces of oxygen.

Example 14

Heterologous Expression of Ppta-AOR2 in *E. coli*

*E. coli* strains pCKAR162 and pCKAR192 grew well under the anaerobic conditions described in Example 13.

Figure 11:
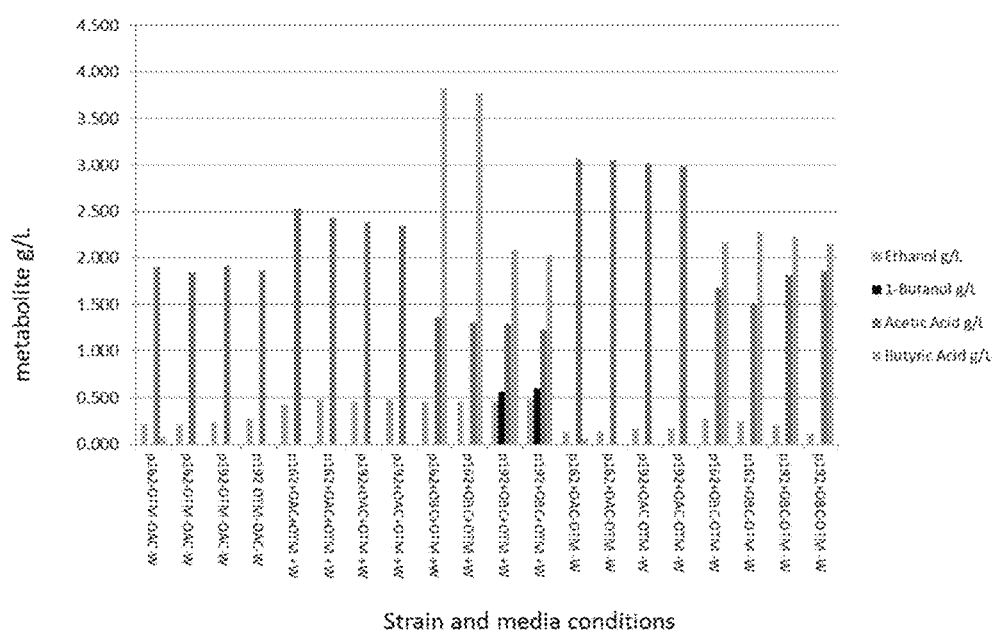
FIG. 11. Graph illustrating heterologous AOR1 expression in *E. coli*. Bioconversion of butyrate to butanol in *E. coli* expressing AOR1 on pCKAR192. No butanol production is observed in *E. coli* containing only pCKAR162.

Cells reached a maximum $OD_{600}$ after about 30 hours. Results of GC analysis of culture metabolites are shown in FIG. 11 for duplicate strains grown either in the presence or absence of acetate and butyrate. When *E. coli* strain pCKAR162 was grown only with glucose as sole carbon and energy source it made about 0.25 g/l ethanol and about 1.75 g/l acetate after 24 hours. The strain containing the Ppta-AOR gene (*E. coli* strain pCKAR192) made the same amount of ethanol and acetate. When trace metals were added along with sodium acetate the production of ethanol increased. The same results were observed with *E. coli* strain pCKAR192 when trace metals and sodium acetate were added to the medium. When 27 mM sodium butyrate was added (~3 g/l) to *E. coli* pCKAR162 none of the butyrate was converted to the alcohol. Some acetate and ethanol were observed as expected since *E. coli* produces these metabolites through known metabolic pathways. In *E. coli* pCKAR192 supplemented with 27 mM of sodium butyrate and tungsten some of the butyrate was converted to 1-butanol at a final concentration of about 0.5 g/L. The butanol production was plasmid dependent and also metal dependent, since no butanol was observed with *E. coli* strain pCKAR192 containing plasmid but no trace metals (FIG. 11). These results confirm the functional activity of the Ppta-AOR expression cassette through the conversion of a non-activated $C_4$ acid requiring strictly anaerobic conditions and very low redox. The fact that *E. coli* strain pCKAR162 did not make any butanol under any of the growth conditions, while having a native CoA synthetase gene, indicates that AOR gene function was solely responsible for converting the supplemented acid to the aldehyde using a non-activated substrate.

Example 15

Vectors for the Generation of a Recombinant Clostridial Biocatalyst Containing Constitutively Expressed Aldehyde Ferredoxin Oxidoreductase The AOR genes have been shown to be regulated at the transcriptional level and can vary with the growth stage (FIGS. 9, 10 and Coskata, unpublished results). Efficient conversion of carboxylic acid to aldehyde in mono- and co-culture by the AOR enzymes has been observed in 100-L fermentations over more than 1000 hours and is predicted to be closely correlated to maintenance of low free acid concentrations. In this regard, down-regulation of AOR expression could be correlated to an increase in the culture free acid concentration (FIG. 9) by an as yet unknown mechanism. Both AOR genes appear to be regulated similarly (although at different absolute transcript levels). A vector construction strategy was developed that involved autonomously replicating plasmids containing the Ppta-ack operon promoter expressing AOR genes. This vector would express one or both of the AOR genes and be fully operative at the enzymatic level when the native genes are down-regulated, thereby potentially reducing free acid accumulation, which can be deleterious to cells and fermenter productivity.

*E. coli-Clostridium* shuttle vectors were constructed by first using a mobilizable plasmid, pARO190 (Parke, 1990), as the backbone. pARO190 contains the basis of mobilization region from pSUP2020 and the origin of transfer from RP4 (Parke, 1990). A kanamycin-resistance gene expressed from a moderately strong *Clostridium* promoter, Psadh, was cloned into the PstI-SphI sites of pARO190. This generated a vector designated pCKAR28, which is expressed in high copy number in *E. coli*. The pMB1 origin contained on pCKAR28 is not functional in *Clostridium* and thus a suitable replicon able to autonomously replicate in *Clostridium* was required. Scanning the closed genome sequence of *C. autoethanogenum* (Coskata, unpublished results) identified two contigs, one of which was the chromosome of >4.3 Mb and the other a 5.456 kb autonomously replicating plasmid. ORF analysis revealed an origin of replication related to the rep 1 superfamily involved in a rolling-circle replication mechanism. A 1.5 kb PstI region containing the ~800 by rep1-homologous region and 700 bp of surrounding DNA was cloned into the unique PstI site contained on pCKAR28. This *E. coli-Clostridium* shuttle vector was designated pCK231 (counterclockwise orientation with respect to the kanamycin resistance gene) and pCK232 (clockwise orientation; FIG. 12, left).

To clone the constitutively expressed AOR1 gene, plasmid pCKAR214, which contains a synthesized Ppta-AOR gene cassette (FIG. 3), was used as template for PCR. PCR primers containing engineered BamHI sites at each 5' end were used to amplify a 2.385 kb fragment containing the promoter, Ppta-ack, the AOR1 gene and downstream sequences including its transcriptional terminator. After amplification, gel purification, and isolation the 2.385 kb product was digested with BamHI and ligated to dephosphorylated pCK232 which was previously digested with BamHI. Putative *E. coli* transformants containing recombinant plasmids were screened by BamHI restriction digestion for the presence of the 2.385 kb insert. Three such recombinant plasmids containing the 2.385 kb insert in the pCK232 backbone were isolated, purified, and the cloned Ppta-AOR cassette additionally confirmed using PCR, additional restriction enzyme analysis and sequencing. This shuttle vector was designated pCK232AOR1 (FIG. 12, right) and was used to transform *C. autoethanogenum* DSM 11061.

Example 16

DNA Transformation

Shuttle vectors pCK232 and pCK232AOR1 were transferred into *C. autoethanogenum* DSM 11061 by electroporation using essentially (with minor modifications) the method reported by Liu et al., (2006) for *C. tyrobutyricum* with scale-down adaptations implemented by Leang et al. (Applied and Environmental *Microbiology*, 79:1102-1109, 2013) for *C. ljungdahlii*. *C. autoethanogenum* DSM 11061 cells were grown in the fermentation medium described in Table 2, containing 5 g/L yeast extract without added DL-threonine and containing fructose as main carbon source (0.5%). Cells were harvested at mid-log phase (OD 600 nm 0.3-0.4) and all subsequent steps including resuspensions and electrotransformation were carried out under strict anoxic conditions in an anaerobic chamber (Coy Products, MI). Washed cells were resuspended in SMP buffer pH 5.8 and aliquoted for individual electrotransformation (25 µl) into a 0.1 µm cuvette or stored frozen for near-term use at −80° C. in 10% DMSO and SMP buffer, pH 5.8. The electroporation parameters used were 625 V, 100Ω and 25 µF. Putative transformants were selected on fermentation medium agar (2%) containing 100 µg/ml kanamycin sulfate. Agar plates were incubated anaerobically in an anaerobic jar at 37° C. under a $N_2$—$CO_2$ headspace.

Example 17

Recombinant AOR Expression Analysis by RT-qPCR

DNA transformation of pCK232AOR1 in *C. autoethanogenum* was confirmed by plasmid rescue into *E. coli* followed by restriction analysis and PCR amplification of a unique junction region of total DNA isolated from biocatalyst strain TF18 (data not shown). In vivo AOR1 expression from pCK232AOR1 in strain TF18 was shown in RT-qPCR tests using AOR1-specific primers and RNA isolated from cultures growing on syngas and fructose as sole carbon and energy sources. Wild-type and TF18 strains were grown in serum bottles (158 ml) in 20 ml of fermentation medium containing 5 g/l yeast extract and either syngas (65% $H_2$, 16% CO, and 15% $CO_2$) or 5 g/l fructose. One milliliter of cells was harvested at different optical densities corresponding to different growth phases, rapidly pelleted and flash frozen in an RNA protection solution. Frozen cells were stored at −80° C. until needed. Total RNA was isolated using the RNA easy kit (Qiagen, Carlsbad, Calif.). Typically 3-5 µg of RNA was extracted/ml cell mass using this procedure. Complementary DNA was generated using reverse transcriptase as described by the manufacturer (ReverseScript, Ambion, Grand Island, N.Y.). For the RT-qPCR, 50 ηg RNA was used for each reaction. A standard curve was set up using plasmid DNA that contained the cloned AOR1 gene target to quantitate transcript levels in the samples. Cycling conditions were: 95° C. for 2 minutes (1 cycle, hot start activation); 40 cycles of 95° C. (denaturation) for 15 sec. and 60° C. (annealing and extension) for 60 sec. A final melting curve (dissociation) cycle of 55-95° C. was performed to confirm specificity.

Figure 13A:
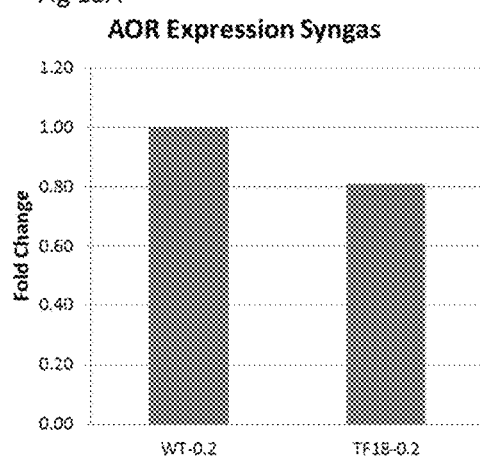
FIGS. 13A and 13B. Graph illustrating aldehyde ferredoxin oxidoreductase expression in wild-type and TF18 strains. RT-qPCR fold change analysis for wild-type and TF18 *C. autoethanogenum* cells grown on syngas (FIG. 13A) and fructose (FIG. 13B). Expression patterns of the AOR1 gene were compared during early-log (on syngas) and mid-log (on fructose).
Figure 13B:
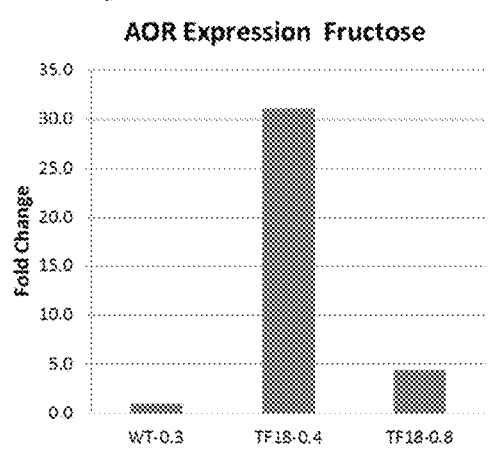

On fructose medium, both TF18 and wild type cells grew to a final OD of about 0.8 after 48-60 hours. Kanamycin at 10 ppm was used for plasmid maintenance in liquid growth for TF18. On syngas medium, the wild-type strain grew normally to a final OD of 0.7 but TF18 only reached an OD of 0.2 over two days and reached its maximum of 0.25 at 60 hours. Transcript levels and specific productivity rates were compared over the course of five days incubation (FIGS. 13, 14). RT-qPCR analysis of the wild-type strain showed that the AOR1 gene is essentially not expressed when cells are grown on fructose but that recombinant strain TF18 expressed AOR1 abundantly (contained on pCK232AOR1) from the constitutive Ppta promoter when growing on fructose (FIG. 13). There was a greater than 30-fold difference between the wild-type and TF18 AOR1 transcript levels when cells were compared in mid-log phase (OD 0.4). In older, stationary phase TP18 cells (OD 0.8) AOR1 transcript declined significantly, although the gene expression levels were still about 4-fold higher than the wild-type strain. In both strains grown on syngas the Wood-Ljungdahl pathway is expected to be operative and the native AOR genes are expressed (FIG. 13), although minor differences between the wild-type and TF18 strains were likely due to differences in growth rates and cell yields under the conditions used.

Example 18

Productivity of *C. autoethanogenum* Strain TF18 Grown on Syngas

Gas chromatography was performed on samples taken after 1, 2, and 5 days for the wild-type and TF18 (expressing recombinant Ppta-AOR) strains grown in syngas. The results showed that the TF18 strain had a more than 2-fold higher specific ethanol productivity rate (grams/OD) throughout the 5-day fermentation period than the wild-type strain (FIG. 14, left). The acetate productivity rate (grams/OD) was lower in the TF18 strain than the wild-type after 1 day of incubation, indicating a more rapid conversion of acid (FIG. 14, right).

Example 19

Scale Up Fermentation Testing of Recombinant Strain TF18

Figure 15:
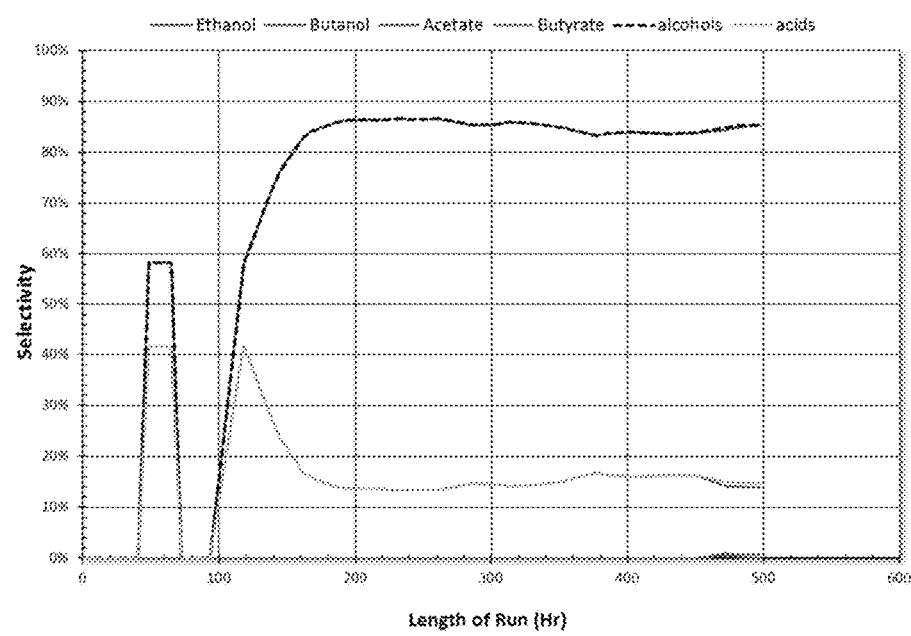
FIG. 15. Selectivity of 5-L fermentation using strain TF18. In the monoculture of strain TF 18 only ethanol and acetate were produced and the percentage of products is shown (total $C_2$ products equals 100%).

The recombinant *C. autoethenogenum* strain TF18 was tested in a 5-L tank growing in fermentation medium at pH 5.2 (Table 2) with kanamycin sulfate added at a final concentration of 25 µg/ml. Frozen stocks of TF18 were grown in 20 ml of fermentation medium in serum bottles containing 0.2% fructose to regenerate the strain. After reaching an OD of 0.8 (about 30 hours) cultures were transferred to 100 ml fermentation medium containing kanamycin sulfate (100 µg/ml) in a syngas headspace (65% $H_2$, 20% CO, and 8% $CO_2$). The 100 ml culture was transferred to 1900 ml fermentation medium in a 5-L reactor. When the culture optical density (600 nm) reached 0.5 an additional 3000 ml medium was added for a final volume of 5 liters. Agitation was ramped up from 225 rpm to 525 rpm over the course of 7 days. Gas flow rate was 100 ml/min early in the fermentation and increased to 141 ml/min during steady state. Product selectivity of *C. autoethanogenum* strain TF18 is shown during a 400 hour period (FIG. 15). Only ethanol and acetate were produced, as expected for this culture. The selectivity in steady state ranged from 83.25% to 86.47% on a molar basis for ethanol and 16.75% to 13.53% for acetate. During the first 100 hours the ratio of ethanol to acetate (molar basis) was better than that seen for the parent strain which would contain only the two native AORs. The more rapid shift to solventogenesis is viewed as a strain and process improvement imparted by the additional AOR gene expression. The improvement in selectivity during this period was between 10-15% when compared to the average of many previous fermentations run solely with the parent strain. Improved selectivity would be one of the expected strain improvements of increased AOR expression, since the amount of total AOR protein would be expected to increase rapidly during growth phase and eventually settle into about $1 \times 10^9$ copies/ µg RNA in the parent strain (FIG. 10). Additional copies of AOR expressed off an autonomously replicating plasmid would likely increase the RNA levels further possibly into the $1 \times 10^{10}$ copies/ µg RNA. Increased transcript likely leads to increased levels of protein which would drive additional acetate to aldehyde conversion. This would in turn have the overall cellular effect of lessening the possibility of acetate accumulation (increased free acid) and cell stress by diminution of the cell's membrane potential, which is primarily where *C. autoethanogenum* obtains its energy. Volumetric gas uptake was similar to that observed for the parental strain and depending on the gas flow ranged from 45 mM/l/h to over 52 mM/l/h. Once the culture was fully acclimated to the fermenter conditions, the growth rate of strain TF18 in the presence of 25 mg/L of kanamycin was easily maintained with a 2-day hydraulic retention time.

*C. autoethanogenum* AOR1 DNA sequence including native promoter.

Seq ID No. 1

```
TCTGAAATGGAACAAAATTGCACCAAGATGGAACAGTTTGCTTGGCGCAATACCCTC
AAAACACAATATTTTATTATTGGCATGGTTTATGCTATATATATAATTGTTTGAATAA
TCAATTTTTTAGGAGGGTTTTTATGTACGGATATAAGGGTAAGGTATTAAGAATTA
ATCTAAGTAGTAAAACTTATATAGTGGAAGAATTGAAAATTGACAAAGCTAAAAAA
TTTATAGGTGCAAGAGGGTTAGGCGTAAAAACCTTATTTGACGAAGTAGATCCAAA
GGTAGATCCATTATCACCTGATAACAAATTTATTATAGCAGCGGGACCACTTACAGG
TGCACCTGTTCCAACAAGCGGAAGATTCATGGTAGTTACTAAATCACCTTTAACAGG
AACTATTGCTATTGCAAATTCAGGTGGAAAATGGGGAGCAGAATTCAAAGCAGCTG
GATACGATATGATAATCGTTGAAGGTAAATCTGATAAAGAAGTTTATGTAAATATAG
TAGATGATAAAGTAGAATTTAGGGATGCTTCTCATGTTTGGGGAAAACTAACAGAA
GAAACTACAAAAATGCTTCAACAGGAAACAGATTCGAGAGCTAAGGTTTTATGCAT
AGGACCAGCTGGGGAAAAGTTATCACTTATGGCAGCAGTTATGAATGATGTTGATA
GAACAGCAGGACGTGGTGGTGTTGGAGCTGTTATGGGTTCAAAGAACTTAAAAGCT
ATTGTAGTTAAAGGAAGCGGAAAAGTAAAATTATTTGATGAACAAAAAGTGAAGGA
AGTAGCACTTGAGAAAACAAATATTTTAAGAAAAGATCCAGTAGCTGGTGGAGGAC
TTCCAACATACGGAACAGCTGTACTTGTTAATATTATAAATGAAAATGGTGTACATC
CAGTAAAGAATTTTCAAAAATCTTATACAGATCAAGCAGATAAGATCAGTGGAGAA
ACTTTAACTAAAGATTGCTTAGTTAGAAAAAATCCTTGCTATAGGTGTCCAATTGCC
TGTGGAAGATGGGTAAAACTTGATGATGGAACTGAATGTGGAGGACCAGAATATGA
AACATTATGGTCATTTGGATCTGATTGTGATGTATACGATATAAATGCTGTAAATAC
AGCAAATATGTTGTGTAATGAATATGGACTAGATACCATTACAGCAGGATGTACTAT
TGCAGCAGCTATGGAACTTTATCAAAGAGGTTATATTAAGGATGAAGAAATAGCAG
CAGATGGATTGTCACTTAATTGGGGAGATGCTAAGTCCATGGTTGAATGGGTAAAG
AAAATGGGACTTAGAGAAGGATTTGGAGACAAGATGGCAGATGGTTCATACAGACT
TTGTGACTCATACGGTGTACCTGAGTATTCAATGACTGTAAAAAAACAGGAACTTCC
AGCATATGACCCAAGAGGAATACAGGGACATGGCATTACTTATGCTGTTAACAATA
GGGGAGGATGTCACATTAAGGGATATATGGTAAGTCCTGAAATACTTGGCTATCCA
GAAAAACTTGATAGACTTGCAGTGGAAGGAAAAGCAGGATATGCTAGAGTATTCCA
TGATTTAACAGCTGTTATAGATTCACTTGGATTATGTATTTTTACAACATTTGGTCTT
GGTGCACAGGATTATGTTGATATGTATAATGCAGTAGTTGGTGGAGAATTACATGAT
GTAAATTCTTTAATGTTAGCTGGAGATAGAATATGGACTTTAGAAAAAATATTTAAC
TTAAAAGCAGGCATAGATAGTTCACAGGATACTCTTCCAAAGAGATTGCTTGAAGA
ACAAATTCCAGAAGGACCATCAAAAGGAGAAGTTCATAAGTTAGATGTACTACTAC
CTGAATATTATTCAGTACGTGGATGGGATAAAAATGGTATTCCTACAGAGGAAACGT
TAAAGAAATTAGGATTAGATGAATACGTAGGTAAGCTTTAG
```

C. autoethanogenum amino acid sequence of AOR1.
Seq. ID No. 2

```
MYGYKGKVLRINLSSKTYIVEELKIDKAKKFIGA
RGLGVKTLFDEVDPKVDPLSPDNKFIIAAGPLTG
APVPTSGRFMVVTKSPLTGTIAIANSGGKWGAEF
KAAGYDMIIVEGKSDKEVYVNIVDDKVEFRDAS
HVWGKLTEETTKMLQQETDSRAKVLCIGPAGEK
LSLMAAVMNDVDRTAGRGGVGAVMGSKNLKAI
VVKGSGKVKLFDEQKVKEVALEKTNILRKDPVA
GGGLPTYGTAVLVNIINENGVHPVKNFQKSYTDQ
ADKISGETLTKDCLVRKNPCYRCPIACGRWVKLD
DGTECGGPEYETLWSFGSDCDVYDINAVNTANM
LCNEYGLDTITAGCTIAAAMELYQRGYIKDEEIA
ADGLSLNWGDAKSMVEWVKKMGLREGFGDKMA
DGSYRLCDSYGVPEYSMTVKKQELPAYDPRGIQ
GHGITYAVNNRGGCHIKGYMVSPEILGYPEKLDR
LAVEGKAGYARVFHDLTAVIDSLGLCIFTTFGLG
AQDYVDMYNAVVGGELHDVNSLMLAGDRIWTLE
KIFNLKAGIDSSQDTLPKRLLEEQIPEGPSKGEVH
KLDVLLPEYYSVRGWDKNGIPTEETLKKLGLDEY
VGKL
```

DNA sequence of C. autoethanogenum AOR2 including native promoter.
Seq. ID No. 3

```
AAATAGTATTGTACGTTATTTGATCACTTTTTTAAAAATAAAATGATAATATTGTATT
TTTTTTGAGCATTTTGGCAATACAAAGAACTGTATTGTTTATTATTTAAGCATTTTAT
TATAAAACAAAAAAACGTTATTAAATTATTTGCTATGAATTCACTTGATAATCAATG
CATTGCATGTGATGTTGATTATTGAGTGTTTTTTTTGTAACCATATTTGGCACAATTT
ATGCTCTATAATATTTCTGAAATAAATACATTTATATGAGGAGGAATTTCAATGTAT
GGTTATGATGGTAAAGTATTAAGAATTAATTTAAAAGAAAGAACTTGCAAATCAGA
AAATTTAGATTTAGATAAAGCTAAAAAGTTTATAGGTTGTAGGGGACTAGGTGTTAA
AACTTTATTTGATGAAATAGATCCTAAAATAGATGCATTATCACCAGAAAATAAATT
TATAATTGTAACAGGTCCTTTAACTGGAGCTCCGGTTCCAACTAGTGGAAGGTTTAT
GGTAGTTACTAAAGCACCGCTTACAGGAACTATAGGAATTTCAAATTCGGGTGGAA
AATGGGGAGTAGACTTAAAAAAAGCTGGTTGGGATATGATAATAGTAGAGGATAAG
GCTGATTCACCAGTTTACATTGAAATAGTAGATGATAAGGTAGAAATTAAAGACGC
GTCACAGCTTTGGGGAAAAGTTACATCAGAAACTACAAAAGAGTTAGAAAAGATAA
CTGAGAATAAATCAAAGGTATTATGTATAGGACCTGCTGGTGAACGATTGTCTCTTA
TGGCAGCAGTTATGAATGATGTAGATAGAACTGCAGCAAGAGGCGGCGTTGGTGCA
GTTATGGGATCTAAAAACTTAAAAGCTATTACAGTTAAAGGAACTGGAAAAATAGC
TTTAGCTGATAAAGAAAAGTAAAAAAAGTGTCCGTAGAAAAAATTACAACATTAA
AAAATGATCCAGTAGCTGGTCAGGGAATGCCAACTTATGGTACAGCTATACTGGTTA
ATATAATAAATGAAAATGGAGTTCATCCTGTAAAGAATTTTCAAGAGTCTTATACGA
ATCAAGCAGATAAAATAAGTGGAGAGACTCTTACTGCTAACCAACTAGTAAGGAAA
```

-continued

```
AATCCTTGTTACAGCTGTCCTATAGGTTGTGGAAGATGGGTTAGACTAAAAGATGGC

ACAGAGTGCGGAGGACCAGAATATGAAACACTGTGGTGTTTTGGATCTGACTGTGG

TTCATATGATTTAGATGCTATAAATGAAGCTAATATGTTATGTAATGAATATGGTAT

TGATACTATTACTTGTGGTGCAACAATTGCTGCAGCTATGGAACTTTATCAAAGAGG

ATATATAAAAGACGAAGAAATAGCTGGAGATAACCTATCTCTCAAGTGGGGTGATA

CGGAATCTATGATTGGCTGGATAAAGAGAATGGTATATAGTGAAGGCTTTGGAGCA

AAGATGACAAATGGTTCATATAGGCTTTGTGAAGGTTATGGAGCACCGGAGTATTCT

ATGACAGTTAAAAAGCAGGAAATTCCAGCATATGATCCAAGGGGAATACAGGGACA

CGGTATTACCTATGCAGTTAATAATAGAGGAGGCTGTCATATTAAGGGATACATGAT

TAACCCTGAAATATTAGGTTATCCTGAAAAACTTGATAGATTTGCATTAGATGGTAA

AGCAGCTTATGCCAAATTATTTCATGATTTAACTGCTGTAATTGATTCTTTAGGATTG

TGCATATTCACTACATTTGGGCTTGGAATACAGGATTATGTAGATATGTATAATGCA

GTAGTAGGAGAATCTACTTATGATGCAGATTCACTATTAGAGGCAGGAGATAGAAT

CTGGACTCTTGAGAAATTATTTAATCTTGCAGCTGGAATAGACAGCAGCCAGGATAC

TCTACCAAAGAGATTGTTAGAAGAACCTATTCCAGATGGCCCATCAAAGGGAGAAG

TTCATAGGCTAGATGTTCTTCTGCCAGAATATTACTCAGTACGAGGATGGAGTAAAG

AGGGTATACCTACAGAAGAAACATTAAAGAAATTAGGATTAGATGAATATATAGGT

AAGTTCTAG
```

Amino acid sequence of *C. autoethanogenum* AOR2.

Seq ID No. 4

```
MYGYDGKVLRINLKERTCKSENLDLDKAKKFIG

CRGLGVKTLFDEIDPKIDALSPENKFIIVTGPLTG

APVPTSGRFMVVTKAPLTGTIGISNSGGKWGVDL

KKAGWDMIIVEDKADSPVYIEIVDDKVEIKDASQ

LWGKVTSETTKELEKITENKSKVLCIGPAGERLS

LMAAVMNDVDRTAARGGVGAVMGSKNLKAITV

KGTGKIALADKEKVKKVSVEKITTLKNDPVAGQ

GMPTYGTAILVNIINENGVHPVKNFQESYTNQAD

KISGETLTANQLVRKNPCYSCPIGCGRWVRLKDG

TECGGPEYETLWCFGSDCGSYDLDAINEANMLC

NEYGIDTITCGATIAAAMELYQRGYIKDEEIAGD

NLSLKWGDTESMIGWIKRMVYSEGFGAKMTNGS

YRLCEGYGAPEYSMTVKKQEIPAYDPRGIQGHGI

TYAVNNRGGCHIKGYMINPEILGYPEKLDRFALD

GKAAYAKLFHDLTAVIDSLGLCIFTTFGLGIQDY

VDMYNAVVGESTYDADSLLEAGDRIWTLEKLFN

LAAGIDSSQDTLPKRLLEEPIPDGPSKGEVHRLD

VLLPEYYSVRGWSKEGIPTEETLKKLGLDEYIGK

F
```

-continued

DNA sequence of AOR2 including Pptaack and terminator region
Seq ID No. 5

```
GAATTCTGATTGATTATTTATTTTAAAATGCCTAAGTGAAATATATACATATTATAAC
AATAAAATAAGTATTAGTGTAGGATTTTTAAATAGAGTATCTATTTTCAGATTAAAT
TTTTGATTATTTGATTTACATTATATAATATTGAGTAAAGTATTGACTAGCAAAATTT
TTTGATACTTTAATTTGTGAAATTTCTTATCAAAAGTTATATTTTTGAATAATTTTTAT
TGAAAAATACAACTAAAAAGGATTATAGTATAAGTGTGTGTAATTTTGTGTTAAATT
TAAAGGGAGGAAAATGTATGGTTATGATGGTAAAGTATTAAGAATTAATTTAAAAG
AAAGAACTTGCAAATCAGAAAATTTAGATTTAGATAAAGCTAAAAAGTTTATAGGT
TGTAGGGGACTAGGTGTTAAAACTTTATTTGATGAAATAGATCCTAAAATAGATGCA
TTATCACCAGAAAATAAATTTATAATTGTAACAGGTCCTTTAACTGGAGCTCCGGTT
CCAACTAGTGGAAGGTTTATGGTAGTTACTAAAGCACCGCTTACAGGAACTATAGG
AATTTCAAATTCGGGTGGAAAATGGGGAGTAGACTTAAAAAAAGCTGGTTGGGATA
TGATAATAGTAGAGGATAAGGCTGATTCACCAGTTTACATTGAAATAGTAGATGATA
AGGTAGAAATTAAAGACGCGTCACAGCTTTGGGGAAAAGTTACATCAGAAACTACA
AAAGAGTTAGAAAAGATAACTGAGAATAAATCAAAGGTATTATGTATAGGACCTGC
TGGTGAACGATTGTCTCTTATGGCAGCAGTTATGAATGATGTAGATAGAACTGCAGC
AAGAGGCGGCGTTGGTGCAGTTATGGGATCTAAAAACTTAAAAGCTATTACAGTTA
AAGGAACTGGAAAAATAGCTTTAGCTGATAAAGAAAAAGTAAAAAAAGTGTCCGTA
GAAAAAATTACAACATTAAAAAATGATCCAGTAGCTGGTCAGGGAATGCCAACTTA
TGGTACAGCTATACTGGTTAATATAATAAATGAAAATGGAGTTCATCCTGTAAAGAA
TTTTCAAGAGTCTTATACGAATCAAGCAGATAAAATAAGTGGAGAGACTCTTACTGC
TAACCAACTAGTAAGGAAAAATCCTTGTTACAGCTGTCCTATAGGTTGTGGAAGATG
GGTTAGACTAAAAGATGGCACAGAGTGCGGAGGACCAGAATATGAAACACTGTGGT
GTTTTGGATCTGACTGTGGTTCATATGATTTAGATGCTATAAATGAAGCTAATATGTT
ATGTAATGAATATGGTATTGATACTATTACTTGTGGTGCAACAATTGCTGCAGCTAT
GGAACTTTATCAAAGAGGATATATAAAAGACGAAGAAATAGCTGGAGATAACCTAT
CTCTCAAGTGGGGTGATACGGAATCTATGATTGGCTGGATAAAGAGAATGGTATAT
AGTGAAGGCTTTGGAGCAAAGATGACAAATGGTTCATATAGGCTTTGTGAAGGTTAT
GGAGCACCGGAGTATTCTATGACAGTTAAAAAGCAGGAAATTCCAGCATATGATCC
AAGGGGAATACAGGGACACGGTATTACCTATGCAGTTAATAATAGAGGAGGCTGTC
ATATTAAGGGATACATGATTAACCCTGAAATATTAGGTTATCCTGAAAAACTTGATA
GATTTGCATTAGATGGTAAAGCAGCTTATGCCAAATTATTTCATGATTTAACTGCTGT
AATTGATTCTTTAGGATTGTGCATATTCACTACATTTGGGCTTGGAATACAGGATTAT
GTAGATATGTATAATGCAGTAGTAGGAGAATCTACTTATGATGCAGATTCACTATTA
GAGGCAGGAGATAGAATCTGGACTCTTGAGAAATTATTTAATCTTGCAGCTGGAATA
GACAGCAGCCAGGATACTCTACCAAAGAGATTGTTAGAAGAACCTATTCCAGATGG
CCCATCAAAGGGAGAAGTTCATAGGCTAGATGTTCTTCTGCCAGAATATTACTCAGT
ACGAGGATGGAGTAAAGAGGGTATACCTACAGAAGAAACATTAAAGAAATTAGGA
TTAGATGAATATATAGGTAAGTTCTAGTTTGATTCGGTAAACTAGAAAGCAGACTTT
```

```
ATGTGTTAAAGAAGATAGCTTCTCTCTATATATGAAGTCTGTTTTTAATAGAAAGAT

ATGAATTTGAGAATAGAAGTTAGATTAGTTGCTTATATATTTGCAAAAGTGTTAAGT

TCTGCTTGGATAAGTTCGGGAGATGAAATTTAGTTGTTATGATAAACTTCAATGAAT

TC
```

DNA sequence of AOR2 including Pcoos with terminator region.

Seq ID No. 6.

```
GATTCTTAGTATAAGTATTCTTAGTATCTTTAGCACTTAGAATACGTTATCCTTTAGG

AGAATAATCCTAATCAGTAGTTCTAATAATTTAATAGTATACTTAAATAGTATATTTT

GGAGGTTTTATTATGTATGGTTATGATGGTAAAGTATTAAGAATTAATTTAAAAGAA

AGAACTTGCAAATCAGAAAATTTAGATTTAGATAAAGCTAAAAAGTTTATAGGTTGT

AGGGGACTAGGTGTTAAAACTTTATTTGATGAAATAGATCCTAAAATAGATGCATTA

TCACCAGAAAATAAATTTATAATTGTAACAGGTCCTTTAACTGGAGCTCCGGTTCCA

ACTAGTGGAAGGTTTATGGTAGTTACTAAAGCACCGCTTACAGGAACTATAGGAATT

TCAAATTCGGGTGGAAAATGGGGAGTAGACTTAAAAAAAGCTGGTTGGGATATGAT

AATAGTAGAGGATAAGGCTGATTCACCAGTTTACATTGAAATAGTAGATGATAAGG

TAGAAATTAAAGACGCGTCACAGCTTTGGGGAAAAGTTACATCAGAAACTACAAAA

GAGTTAGAAAAGATAACTGAGAATAAATCAAAGGTATTATGTATAGGACCTGCTGG

TGAACGATTGTCTCTTATGGCAGCAGTTATGAATGATGTAGATAGAACTGCAGCAAG

AGGCGGCGTTGGTGCAGTTATGGGATCTAAAAACTTAAAAGCTATTACAGTTAAAG

GAACTGGAAAAATAGCTTTAGCTGATAAAGAAAAAGTAAAAAAAGTGTCCGTAGAA

AAAATTACAACATTAAAAAATGATCCAGTAGCTGGTCAGGGAATGCCAACTTATGG

TACAGCTATACTGGTTAATATAATAAATGAAAATGGAGTTCATCCTGTAAAGAATTT

TCAAGAGTCTTATACGAATCAAGCAGATAAAATAAGTGGAGAGACTCTTACTGCTA

ACCAACTAGTAAGGAAAAATCCTTGTTACAGCTGTCCTATAGGTTGTGGAAGATGGG

TTAGACTAAAAGATGGCACAGAGTGCGGAGGACCAGAATATGAAACACTGTGGTGT

TTTGGATCTGACTGTGGTTCATATGATTTAGATGCTATAAATGAAGCTAATATGTTAT

GTAATGAATATGGTATTGATACTATTACTTGTGGTGCAACAATTGCTGCAGCTATGG

AACTTTATCAAAGAGGATATATAAAAGACGAAGAAATAGCTGGAGATAACCTATCT

CTCAAGTGGGGTGATACGGAATCTATGATTGGCTGGATAAAGAGAATGGTATATAG

TGAAGGCTTTGGAGCAAAGATGACAAATGGTTCATATAGGCTTTGTGAAGGTTATGG

AGCACCGGAGTATTCTATGACAGTTAAAAAGCAGGAAATTCCAGCATATGATCCAA

GGGGAATACAGGGACACGGTATTACCTATGCAGTTAATAATAGAGGAGGCTGTCAT

ATTAAGGGATACATGATTAACCCTGAAATATTAGGTTATCCTGAAAAACTTGATAGA

TTTGCATTAGATGGTAAAGCAGCTTATGCCAAATTATTTCATGATTTAACTGCTGTAA

TTGATTCTTTAGGATTGTGCATATTCACTACATTTGGGCTTGGAATACAGGATTATGT

AGATATGTATAATGCAGTAGTAGGAGAATCTACTTATGATGCAGATTCACTATTAGA

GGCAGGAGATAGAATCTGGACTCTTGAGAAATTATTTAATCTTGCAGCTGGAATAGA

CAGCAGCCAGGATACTCTACCAAAGAGATTGTTAGAAGAACCTATTCCAGATGGCC

CATCAAAGGGAGAAGTTCATAGGCTAGATGTTCTTCTGCCAGAATATTACTCAGTAC

GAGGATGGAGTAAAGAGGGTATACCTACAGAAGAAACATTAAAGAAATTAGGATTA

GATGAATATATAGGTAAGTTCTAGTTTGATTCGGTAAACTAGAAAGCAGACTTTATG

TGTTAAAGAAGATAGCTTCTCTCTATATATGAAGTCTGTTTTTAATAGAAAGATATG
```

```
AATTTGAGAATAGAAGTTAGATTAGTTGCTTATATATTTGCAAAAGTGTTAAGTTCT
GCTTGGATAAGTTCGGGAGATGAAATTTAGTTGTTATGATAAACTTCAATGAATTC
```

*C. pharus* Butyryl-CoA acetate transferase    Seq. ID No. 7

```
ATGAGGAAGGTGTTTTATTTAAAATATTAATAAATTTTTTGGAAGGGGTTTTAAAA
ATGGTTTTTAAAAATTGGCAGGATCTTTATAAAAGTAAATTTGTTAGTGCAGATGAA
GCTGTATCTAAGGTAAACTGTGGGGATACTATAGTTTTAGGTAATGCTTGTGGAGCA
CCTCTTACACTTTTAGATGCTTTGGCTGCAAATAAGGAAAAGTATAAGAGTGTACAG
ATATATAATCTTATACTGAACTATAAAAGTGATATATATGCTGAACCAGGTGCAGAA
AAGTATATTCATGGAAATACTTTTTTTGTAAGTGGAGGTACTAAGGAAGCTGTTAAT
TGTAACAGAACAGATTATACCCCATGCTTTTTTTATGAAATACCAAAATTAATAAAA
CAAAATATATACATATAGATGTAGCATTTATTCATGTAAGTAAACCTGATAAGCAT
GGTTATTGTAGTTTTGGAGTATCAACTGATTATTCACAGGCAATGGTACAGGGTGCT
AAACTTGTAATTGCAGAAGTAAACGATCAAATGCCAAGAGTTTTTGGAGACAATTTT
ATACACATTTCTGATATTGATTACATAGTAAAGACTTCACGCCCAATTCTTGAGTTG
GCACCTCCTAAAATAGGAGAAGTAGAAAAAACAATAGGAAAATATTGTGCATCTCT
TATAGAAGATGGTTCTACACTTCAACTTGGAATAGGCGCTATTCCAGATGCAGTACT
TTTGTTTTTGAAAGACAAAAAAGATTTGGGAATACACTCAGAAATGATATCTGATGG
TGTTGTAGAATTAGTTGAATCAGGAGTAATTACAAATAAGAAAAAAGCTCTTCATCC
AGGAAAAATAATTGTTACATTCTTAATGGGAACTAAAAAATTATATGATTTTATAGA
TGATAATCCTATGGTAGAAGGTTATCCAGTAGATTATGTAAATGATCCTAAAGTTAT
TATGCAAAATTCCAAGATGGTATGTATAAATTCTTGTGTAGAGGTAGATTTTACAGG
ACAGGTGTGTGCTGAAAGTATAGGATTTAAGCAGATAAGCGGAGTAGGCGGACAAG
TTGATTATATGAGAGGTGCTAGCATGTCTGATGGAGGAAAATCAATTCTTGCTATAC
CATCTACTGCAGCTGGCGGCAAAATTTCAAGAATAGTTCCGATGTTGACTGAAGGAG
CAGGAGTTACTACTTCAAGATATGATGTTCAATATGTTGTTACAGAGTATGGTATTG
CACTTCTCAAGGGTAAATCCATAAGAGAAAGAGCTAAAGCTCTTATAAACATTGCA
CATCCTAAATTTAGAGAACAATTAGAAAAATCGTTTGAAGAAAGATTTAGTTGTAAA
CTTTAA
```

*C. kluyveri* Butyryl-CoA acetate transferase-1    Seq. ID No. 8

```
ATGGTTTTTAAAAATTGGCAGGATCTTTATAAAAGTAAAATTGTTAGTGCAGACGAA
GCTGTATCTAAAGTAAGCTGTGGAGATAGCATAATTTTAGGCAATGCTTGTGGAGCA
TCTCTTACACTTTTAGATGCCTTGGCTGCAAATAAGGAAAAGTATAAGAGTGTAAAG
ATACACAATCTTATACTTAATTATAAAAATGATATATATACTGATCCGGAATCAGAA
AAGTATATTCATGGAAATACTTTCTTTGTAAGTGGAGGTACAAAGGAAGCAGTTAAT
TGTAATAGAACAGATTATACTCCATGCTTTTTTTATGAAATACCAAAATTATTAAAA
CAAAAGTATATAAATGCAGATGTAGCTTTTATTCAAGTAAGTAAGCCTGATAGCCAT
GGATACTGTAGCTTTGGAGTATCAACCGATTATTCACAGGCAATGGTACAGTCTGCA
AAGCTTATAATTGCAGAAGTAAACGATCAGATGCCAAGAGTTTTAGGAGACAATTTT
ATACACATTTCTGATATGGATTACATAGTAGAAAGTTCACGTCCAATTCTAGAATTG
ACTCCTCCTAAAATAGGAGAAGTAGAGAAGACAATAGGAAAATACTGTGCATCTCT
```

-continued

TGTAGAAGATGGTTCTACACTTCAGCTTGGAATAGGAGCTATTCCAGATGCAGTACT

TTTATTCTTGAAGGATAAAAAGGATTTGGGTATACATTCAGAAATGATATCCGATGG

TGTTGTTGAATTAGTTGAAGCAGGGGTAATTACAAATAAGAAAAAGTCCCTTCATCC

AGGAAAAATAATTATTACATTCTTAATGGGAACTAAGAAATTATATGATTTCATAAA

TGATAATCCTATGGTAGAAGGATACCCTGTAGATTATGTAAATGATCCTAAGGTTAT

TATGCAAAATTCTAAGATGGTATGTATAAACTCCTGTGTAGAAGTGGATTTCACAGG

ACAAGTGTGTGCTGAAAGTGTAGGATTTAAACAAATAAGCGGTGTAGGTGGACAAG

TTGATTACATGAGAGGAGCTAGCATGGCTGATGGAGGAAAATCAATTCTTGCTATAC

CATCTACTGCAGCTGGCGGCAAAATTTCAAGAATAGTTCCTATTTTAACTGAAGGAG

CGGGGGTTACTACTTCAAGATATGATGTTCAATATGTTGTTACAGAATATGGTATTG

CACTTCTCAAGGGCAAATCCATAAGAGAAAGAGCTAAGGAGCTTATAAAAATTGCA

CATCCTAAATTTAGGGAAGAATTAACAGCTCAATTTGAAAAAGATTCAGTTGTAAG

CTTTAA

*C. carboxidivorans* Butyrate kinase-1

Seq. ID No. 9

ATGAGTTATAAGATATTAGCAATTAACCCAGGATCTACTTCTACAAAAATAGCTTTA

TACGAAGATGAAAAAGAAATATTTTGCAAAACGTTAGAGCATCCAGTTGAACAAAT

TGAAAAATATGAGAATGTGGCAGATCAATTTGATATGAGAAAAGAAGTTGTTCTTTC

ATTTTTAAAGCAAAATGGATATGAAGTTAAAGAATTAGCTGCAGTTGTTGGAAGAG

GTGGAATGGTTCCAAAAGTAAAATCTGGAGCTTATAAAGTTAATGAAACAATGGTA

GATAGATTAAAAAATAATCCAGTAGTAGAACATGCTTCAAATTTAGGAGCTTTAATT

GCTTATGAAATAGCAAATTCTATTGGAGTATCAGCCTATATATATGACTCTGTTAGA

GTAGATGAATTAGAGGATATAGCTCGTATATCAGGTATGCCGGATATACCAAGAAC

AAGTACTAGTCATGCATTAAATACAAGGGCAATGGCAATGAAGGTTGCAAAAAATT

ATGGTAAAAAGTATTCAGATATGAACTTTATTGTAGCTCATCTAGGTGGAGGAATAT

CAGTAAATGTTCATAGAAAAGGACAAATGGTAGATATAATGGCAGATGACGAAGGA

CCATTTTCACCTGAAAGAGCTGGAAAAGTTCCTTGCAATGCACTTATAGATCTTTGC

TATTCAGGAAAATTTGATAAAAAAACTACGAAGAAAAAATTAAGGGGAAATGGTGG

ATTAAAAGCTTATCTTAACACTGTTGATGCTAGAGAAGTTGAAAGAATGATTGAAAG

TGGAGATGAAAAAGCAAAGCTTGTTTATGAAGCTATGGCTTATCAGGTTGCTAAGG

GAATAGGAGAACTTGCAACAGTAGTAGAAGGTAAGGTTGATGCTATCGTTATTACA

GGAGGTATAGCATATTCTGATATGATAACTAACTGGATTAAAAAGCGTGTAGAGTTT

ATTGCGCCTGTTGAGATTATGCCTGGTGAAAATGAAATGGAATCTTTGGCTTTGGGA

ACTCTTAGAGTGTTAAAGGGTGAAGAAGAAGCAAGAGAATATGTTGAATAA

*C. carboxidivorans* butyrate kinase-2

Sequence ID No. 10

TTGCTAATTAAAATATTTATTAAGTATTGCTATAATCAGGAGGGTAAAATAATGTAC

AAAATACTAGCAATAAATCCAGGTTCAACTTCAACTAAAATAGCTATTTATGATGAC

ACAGAGGAATTATTTAAAACCACTATAGAACATTCTAGTGAAGAAGTGAAAAAATA

TGAAAACATAGCTGATCAATATAGTATGAGATATGAAGCTATAATGAAATTTTTAAA

AGAAGTAGATTTTGATGTCAAAGCTTTATCTGCAGTAGTTGGAAGAGGAGGAATTCT

GCCTCCAGTTAAATCAGGAGCTTACAGAGTAAATGATTCTATGGTAGAAAGACTGG

CTAAAAGACCTGTAGTAGAGCATGCTTCAAATTTAGGAGCTATAATTTCATATGCAA

-continued

```
TAGCAAAACCTTTAAATATACCAGCTTTCATATATGATTCTGTAGCTGTAGATGAAT

TTGAGGATATTGCAAGAATATCAGGACTTGCAGATATAAAAAGAGAGAGTTTTATTC

ATGCTTTAAATATGAGAGCTGCAGCAATAAAAACAGCAAAAAAACTAGGTAAACCT

TATGAACAATGTAATTTAGTTGTTGCTCATTTAGGAGGCGGAATATCTCTTACTGTAC

ATAAAGGTGGAAAAATGATAGACGCTGTTACTGATGAAGAAGGACCGTTTTCACCA

GAAAGGTCAGGTAGAGTACCTTGTAAGCGCTTAATAGAAATGTGTTATAAAAATGA

TGAACGCACAATGAAAAGAAAATAAGAGGAGATGGTGGATTAATCTCTTATTTAG

GAACTAATAGTGCATTAGATGTAGAAAAAAGAATTGAAAATGGAGATGCTGAAGCC

AAATTAGTTTATGAAGCTATGGCATATCAAATTGCAAAAGCAATAGGAGAACTTGC

AACTGTAGTAAAGGGAAAGGTTGATGCAGTAGTAATTACAGGGGGAATTGCCTATT

CAAAAATGATGACAGGATGGATAAAAGAAAGAGTAGAATTTATAGCACCTGTAGAG

ATATTGCCAGGAGAAATGAATTAGAATCTCTTGCTTTAGGTACGCTTAGAGTTATA

AAGGGAGAAGAAAAAGCACACGAATATGATTTAGATTAG
```

*C. carboxidivorans* Butyrate Kinase-3.
Sequence ID No. 11
```
ATGTCATATAAATTATTAATATTAAATCCAGGATCTACATCTACCAAAATAGGAGTA

TATGATGGAGAAAATGAAATTTTAGAAGAAACTTTAAGACATTCTTCAGAAGAAAT

TGAGAAATATGCTACTATTTATGATCAATTTGAATTTAGAAAAGAAGTTATATTGAA

GGTTTTAAAAGAAAAGAATTTTGATATTAATACATTAGACGGAGTAGTAGGCAGAG

GTGGATTATTAAAACCAATTGAAAGTGGAACTTATAAAGTCAATGATGCTATGTTAG

AAGACCTAAAAGTTGGAGTGCAAGGACAGCATGCTTCAAATTTAGGTGGAATAATA

GCTAATGAAATAGGAAAATCTATAAATAAACCAGCATTTATAGTAGACCCAGTTGTT

GTTGATGAATTAGATGAAGCAGCTAGAATATCCGGAATGCCTGAAATAGAAAGAAT

AAGTATATTCCATGCTTTAAATCAAAAAGCAGTAGCAAAGAGATATGCAAAAGAAA

ACAATAAGAAGTATGATGAATTAAATTTAGTAGTGACACACATGGGTGGCGGAGTA

ACTGTTGGAGCTCACAAAAAAGGAAGAGTTGTAGATGTAGCCAATGGTTTAGATGG

AGATGGACCATTTTCACCAGAAAGAACAGGAGGACTTCCTGTAGGAGGTTTAATAA

AGCTTTGCTATAGTGGAAAATATACTTTAGAAGAAATGAAGAAAAAGATAAGTGGA

AAAGGTGGAATTGTAGCTTATCTAAATACAAATGATTTTAGGGAAGTAGAACAAAA

AGCAGAAAGTGGAGATAAAAAGGCAAAGTTAGTATTTGATGCTTTCATATTACAAG

TAGGTAAAGAAATTGGTAAATGTGCTGCAGTTTTACATGGAAAAGTAGATGCTTTAA

TTTTAACTGGAGGAATAGCTTATAGTAAAACTGTTACAGCTGCAATAAAAGACATGG

TAGAATTTATTGCACCAGTTGTAGTTTATCCAGGAGAAGATGAATTATTAGCATTAG

CACAAGGCGGACTTAGAGTACTAGGTGGAGAAGAACAAGCAAAAGAATATAAGTA

A
```

*C. difficile* butyrate kinase
Sequence ID No. 12
```
ATGACTTACAGAATATTAGCCATAAATCCAGGTTCTACTTCTACAAAAATAGCAGTA

TATGATGGAGAAGAACAAATTCTTGTGAAGACGATAGACCATCCGGCTGAAGAGAT

TGCAAAATATAATACTATACAAGACCAGTTTGAAATGCGTAAGGAAGCAGTTTTGA

ATATTCTTAAAGAAAATAGTATAGACTTAAAATCTCTTAGTGCAATAGTAGGAAGAG

GTGGAGTTTTACCACCAGTAAAAATCAGGAGCATATTTAGTAAATGAAGAAATGATT
```

-continued

GATGTACTAAGACATAGACCAGTACTTGAACACGCTTCCAATTTAGGTGCTGTTGTG

GCACATGCAATATCAGAACCTCTTGGAATCAACTCATATATTTATGATTCTGTTGCA

GTAGATGAGCTTATAGATGTAGCGAGAATATCTGGACTTTGTGGAATGGATAGATCA

AGTGCAGGGCATGCATTAAATACTAGAGCAATGGCTTTAAAATATGCTAAGGATAA

AGGAAAAGATTATAAGAGCTTAAACTTAATAGTAGCTCACATTGGTGGAGGAGTAA

GTATTTATCTTCATGAAAAAGGAAGAATGGTTGATATGCTATCTGATGATGAAGGAC

CATTTTCTCCAGAAAGGTCAGGAAGAGTACCTGCTACAAAATTAGTGGCTGCCTGTT

ATTCAGGTCAATATTCAGAAAGAGAAATGACTAAAAAGATAAGAGGTAAAGGTGGT

ATAGTTTCATACCTAAATACTGTAGATGCTAGAGAAGTTGAAAAAATGATAGCAGA

AGGAAATGAAGAAGCAAAAATTATTTATGAAGCAATGGCTTATCAGTTAGCAAAAG

GTATTGGAGAGTTAGCAACTGTAGTAGATGGAAAGGTAGATGCTATAATTATAACA

GGTGGAATTGCATATTCTGAAATGTTTACTTCAATGGTTAAAAAGAAAGTTGAGTTT

ATAGCACCAGTAGAAATTATGGCAGGAGAAATGAGTTGGATAATCACTTGCTTTTG

GAACTTTAAGAGTACTAAATGGAGAAGAAGAAGCTAGAATTTATAGTGAAA 171 bp region in tungsten-dependent aldehyde
ferredoxin oxidoreductase -1 (AOR1) covered by the probes
found in Seq. ID No. 1

Seq ID No. 13

5'-

ACTTGGATTATGTATTTTTACAACATTTGGTCTTGGTGCACAGGATTATGTTGATATG

TATAATGCAGTAGTTGGTGGAGAATTA

CATGATGTAAATTCTTTAATGTTAGCTGGAGATAGAATATGGACTTTAGAAAAAATA

TTTAACTTAAAAGCAGGCATAGATAGTTCA-3'

169 bp region in tungsten-dependent aldehyde ferredoxin
oxidoreductase #2 (AOR2) covered by the probes found in Seq. ID NO: 3.

Seq ID No. 14

5'-

AAGAAAGAACTTGCAAATCAGAAAATTTAGATTTAGATAAAGCTAAAAAGTTTATA

GGTTGTAGGGGACTAGGT

GTTAAAACTTTATTTGATGAAATAGATCCTAAAATAGATGCATTATCACCAGAAAAT

AAATTTATAATTGTAACAGGTCCTTTAACTGGAGCTCCG-3'

*C. ljungdahlii* AOR1

Seq ID No. 15

MYGYKGKVLRINLSSKTYIVEELKIDKAKKFIGARGLGVKTLFDEVDPKVDPLSPDNKFI

IAAGPLTGAPVPTSGRFMVVTKSPLTGTIAIANSGGKWGAEFKAAGYDMIIVEGKSDKE

VYVNIVDDKVEFRDASHVWGKLTEETKMLQQETDSRAKVLCIGPAGEKLSLMAAVM

NDVDRTAGRGGVGAVMGSKNLKAIVVKGSGKVKLFDEQKVKEVALEKTNILRKDPVA

GGGLPTYGTAVLVNIINENGVHPVKNFQKSYTDQADKISGETLTKDCLVRKNPCYRCPI

ACGRWVKLDDGTECGGPEYETLWSFGSDCDVYDINAVNTANMLCNEYGLDTITAGCTI

AAAMELYQRGYIKDEEIAADGLSLNWGDAKSMVEWVKKMGLREGFGDKMADGSYRL

CDSYGVPEYSMTVKKQELPAYDPRGIQGHGITYAVNNRGGCHIKGYMVSPEILGYPEKL

DRLAVEGKAGYARVFHDLTAVIDSLGLCIFTTFGLGAQDYVDMYNAVVGGELHDVNSL

MLAGDRIWTLEKIFNLKAGIDSSQDTLPKRLLEEQIPEGPSKGEVHKLDVLLPEYYSVRG

WDKNGIPTEETLKKLGLDEYVGKL

*C. ragsdalei* AOR1

Seq ID No. 16

MYGYSGKVLRINLSNKTYKAEELKIDEAKKFIGARGLGVKTLLDEIDPKIDPLSPDNKFII
ATGPLTGAPVPTSGRFMVITKAPLTGTIGIANSGGKWGAELKTAGYDMVIVEGKSDKPV
YVNIVDDKVEFKDASHVWGKLTEETTKMLQNEIDAKAKVLCIGPAGENLSLMAAVMN
DIDRTAGRGGVGAVMGSKNLKAIVVKGSGKVKLFDEEKVKAVSLQKSDILRKDPVAGG
GLPTYGTAVLVNIINENGINPVRNFQESYTDEADKVSGETMTQECLVRKNPCYRCPIACG
RWVRLDDGTECGGPEYETLWSFGSDCDVYDLNAVNKANMLCNEYGLDTISAGATIASA
MELYQRGYIKDEEIAADGL SLKWGDAKSMVEWVKKMGRREGFGGKMADGSYRLCES
YGVPQYSMSVKKQELPAYDPRGAQGHGLTYAVNNRGGCHIKGYMISPEILGYPEKLDR
FSIEGKPAYAKVFHDLTAVIDSLGLCIFTTFGLGAQDYVDMYNAVVGGELHDVDSLML
AGDRVWTLEKIFNLKAGVGSSQDTLPKRLLEEEVVEGPSKGHVHRLDELVPEYYSVRG
WDKNGVPTEETLKKLGLEEYIGKI

*C. ljungdahlii* AOR2

Seq ID No. 17

MYGYDGKVLRINLKERTCKSENLDLDKAKKFIGCRGLGVKTLFDEIDPKIDALSPENKFII
VTGPLTGAPVPTSGRFMVVTKAPLTGTIGISNSGGKWGVDLKKAGWDMIIVEDKADSPV
YIEIVDDKVEIKDASQLWGKVTSETTKELEKITENKSKVLCIGPAGERLSLMAAVMNDV
DRTAARGGVGAVMGSKNLKAITVKGTGKIALADKEKVKKVSVEKITTLKNDPVAGQG
MPTYGTAILVNIINENGVHPVKNFQESYTNQADKISGETLTANQLVRKNPCYSCPIGCGR
WVRLKDGTECGGPEYETLWCFGSDCGSYDLDAINEANMLCNEYGIDTITCGATIAAAM
ELYQRGYIKDEEIAGDNLSLKWGDTESMIGWIKRMVYSEGFGAKMTNGSYRLCEGYGA
PEYSMTVKKQEIPAYDPRGIQGHGITYAVNNRGGCHIKGYMINPEILGYPEKLDRFALDG
KAAYAKLFHDLTAVIDSLGLCIFTTFGLGIQDYVDMYNAVVGESTYDADSLLEAGDRIW
TLEKLFNLAAGIDSSQDTLPKRLLEEPIPDGPSKGEVHRLDVLLPEYYSVRGWSKEGIPTE
ETLKKLGLDEYIGKF

*C. ragsdalei* AOR2

Seq ID No. 18

MYGYNGKVLRINLKERTCKSENLDLDKAKKFIGCRGLGVKTLFDEIDPKIDALSPENKFII
VTGPLTGAPVPTSGRFMVVTKAPLTGTIGISNSGGKWGVDLKKAGWDMIIVEDKADSPV
YIEIVDDKVEIKDASQLWGKVTSETTKELEKITENRSKVLCIGPAGERLSLMAAVMNDV
DRTAARGGVGAVMGSKNLKAITVKGTGKIALADKEKVKKVSVEKITTLKNDPVAGQG
MPTYGTAILVNIINENGVHPVNNFQESYTDQADKISGETLTANQLVRKNPCYSCPIGCGR
WVRLKDGTECGGPEYETLWCFGSDCGSYDLDAINEANMLCNEYGIDTITCGATIAAAM
ELYQRGYVKDEEIAGDNLSLKWGDTESMIGWIKKMVYSEGFGAKMTNGSYRLCEGYG
VPEYSMTVKKQEIPAYDPRGIQGHGITYAVNNRGGCHIKGYMINPEILGYPEKLDRFALD
GKAAYAKMMHDLTAVIDSLGLCIFTTFGLGIQDYVDMYNAVVGESTCDSDSLLEAGDR
VWTLEKLFNLAAGIDSSQDTLPKRLLEEPIPDGPSKGHVHRLDVLLPEYYSVRGWSKEGI
PTEETLKKLGLDEYIGKF

AOR1-A-forward primer

Seq ID No. 19

5'-ACTTGGATTATGTATTTTTACA-3'

AOR1-A-reverse primer

Seq ID No. 20

5'-TGAACTATCTATGCCTGCTTTT-3'

-continued

AOR2-A-forward primer

Seq ID No. 21

5'-AAGAAAGAACTTGCAAATCA-3'

AOR2-A reverse primer

Seq ID No. 22

5'-CGGAGCTCCAGTTAAAGGA-3'

BCoAAT forward primer

Seq ID No. 23

5'-AGCCATGCTAGC TCCTCTCATGTA-3'

BCoAAT reverse primer

Seq ID No. 24

5'-GGAGTATCAACCGAT TATTCACAG-3'

Buk forward primer

Seq ID No. 25

5'-GATGGTTCTACACTT CAGCTT-3'

Buk reverse primer

Seq ID No. 26

5'-GAT ATC ATT TCT GAA TGT ATA CCC-3' iron-only hydrogenase-forward primer

Seq ID No. 27

5'-TGT GAA CGT CCT GAA ATG AAA G-3' iron-only hydrogenase reverse primer

Seq ID No. 28

5'-AGT GCC TGC ACC AGA ATA AGT T-3'

Hyg-1 forward primer

Seq ID No. 29

5'-GCCCGATATAAATCCTCTTT-3'

Hyg-1 reverse primer

Seq ID No. 30

5'-CCAACAAAAATTCCATGATT-3'

Hyg-2 forward primer

Seq ID No. 31

5'-CTACAATTTTAAACGCTGCA-3'

Hyg-2 reverse primer

Seq ID No. 32

5'-GCTCTGGCACTGTTTGTTCTA-3'

Hyg-3 forward primer

Seq ID No. 33

5'-TGA TAC AAA CTT TGG TGC AG-3'

Hyg-3 reverse primer

Seq ID No. 34

5'-ATA TAG CTC CAG CCA TCT GA-3'

---

The invention claimed is:

1. A microorganism co-culture for butanol production by the conversion of syngas to butanol comprising: (i) a recombinant C1-fixing homoacetogen microorganism grown on a medium containing syngas as the sole carbon source under anaerobic condition wherein said C1-fixing homoacetogen microorganism is capable to convert the syngas to butanol and comprises a heterologous gene encoding an aldehyde ferredoxin oxidoreductase polypeptide modulated by a promoter, (ii) and a C4-producing butyrate microorganism, wherein the nucleotide sequence of aldehyde ferredoxin oxidoreductase gene has greater than 97% sequence identity to SEQ ID NO: 1 or SEQ ID NO: 3.

2. The co-culture of claim 1 wherein the promoter is an inducible promoter or a constitutive promoter.

3. The co-culture of claim 1 wherein the C1-fixing homoacetogen microorganism is *C. ljungdahlii, C. ragsdalei, C. autoethanogenum* or *C. coskatii*.

4. The co-culture of claim 1 wherein the C4-producing butyrate microorganism is *Clostridium kluyveri, Clostridium carboxidivorans*, or *Butyribacterium methylotrophicum*.

* * * * *